US011021535B2

(12) United States Patent
Seder et al.

(10) Patent No.: US 11,021,535 B2
(45) Date of Patent: Jun. 1, 2021

(54) NEUTRALIZING ANTIBODIES TO PLASMODIUM FALCIPARUM CIRCUMSPOROZOITE PROTEIN AND THEIR USE

(71) Applicants: THE UNITED STATES OF AMERICA, AS REPRESENTED BY THE SECRETARY, DEPARTMENT OF HEALTH AND HUMAN SERVICES, Bethesda, MD (US); SANARIA INC, Rockville, MD (US)

(72) Inventors: Robert Seder, Chevy Chase, MD (US); Neville Kisalu, Bethesda, MD (US); Azza Idris, Bethesda, MD (US); Barbara Flynn, Bethesda, MD (US); Stephen Hoffman, Rockville, MD (US)

(73) Assignees: The United States of America as represented by the Secretary, Department of Health and Human Services, Bethesda, MD (US); Sanaria Inc., Rockville, MD (US)

( * ) Notice: Subject to any disclaimer, the term of this patent is extended or adjusted under 35 U.S.C. 154(b) by 0 days.

(21) Appl. No.: 16/485,354

(22) PCT Filed: Feb. 12, 2018

(86) PCT No.: PCT/US2018/017826
§ 371 (c)(1),
(2) Date: Aug. 12, 2019

(87) PCT Pub. No.: WO2018/148660
PCT Pub. Date: Aug. 16, 2018

(65) Prior Publication Data
US 2019/0375831 A1 Dec. 12, 2019

Related U.S. Application Data

(60) Provisional application No. 62/457,720, filed on Feb. 10, 2017.

(51) Int. Cl.
*C07K 16/20* (2006.01)
(52) U.S. Cl.
CPC ........ *C07K 16/205* (2013.01); *C07K 2317/21* (2013.01); *C07K 2317/34* (2013.01); *C07K 2317/76* (2013.01); *C07K 2317/92* (2013.01)
(58) Field of Classification Search
None
See application file for complete search history.

(56) References Cited

U.S. PATENT DOCUMENTS 9,321,834 B2 4/2016 Gutierrez et al.

FOREIGN PATENT DOCUMENTS

WO WO 2015/085140 A1 6/2015

OTHER PUBLICATIONS

Skolnick et al. (Trends in Biotechnology 18: 34-39, 2000).*
Greenspan et al. (Nature Biotechnology 7: 936-937, 1999).*
Giusti et al. (Proc. Natl. Acad. Sci. USA. May 1987; 84 (9): 2926-2930).*
Winkleretal (J. Imm., 265:4505-4514, 2000).*
Chien et al. (Proc. Natl. Acad. Sci. USA. Jul. 1989; 86 (14): 5532-5536).*
Caldas et al. (Mol. Immunol. May 2003; 39 (15): 941-952).*
Casadevall et al. (PNAS vol. 109 No. 31, p. 12272-12273).*
Barry et al., "Strategies for designing and monitoring malaria vaccines targeting diverse antigens." *Frontiers in Immunology* 5, Article 359 (2014): 1-16.
Clement et al., "Validation of an enzyme-linked immunosorbent assay for the quantification of human IgG directed against the repeat region of the circumsporozoite protein of the parasite *Plasmodium falciparum." Malaria Journal* 11, No. 384 (2012): 1-15.
Espinosa et al., "Proteolytic Cleavage of the Plasmodium falciparum Circumsporozoite Protein Is a Target of Protective Antibodies." *J Infect Dis* 212, No. 7 (2015): 1111-1119.
Foquet et al., "Vaccine-induced monoclonal antibodies targeting circumsporozoite protein prevent Plasmodium falciparum infection." *The Journal of Clinical Investigation* 124, No. 1 (2014): 140-144.
Ishizuka et al., "Protection against malaria at 1 year and immune correlates following PfSPZ vaccination." *Nature Medicine* 22, No. 6 (2016): 614-692.
Kisalu et al., "A human monoclonal antibody prevents malaria infection and defines new site of vulnerability on Plasmodium falciparum circumsporozoite protein." *Nat Med.* 24, No. 4 (2018): 408-416, including Supplemental Materials and Amendments.

* cited by examiner

*Primary Examiner* — Robert A Zeman
(74) *Attorney, Agent, or Firm* — Klarquist Sparkman, LLP

(57) ABSTRACT

Antibodies and antigen binding fragments that specifically bind to *P. falciparum* circumsporozoite protein and neutralize *P. falciparum* are disclosed. Nucleic acids encoding these antibodies, vectors and host cells are also provided. The disclosed antibodies, antigen binding fragments, nucleic acids and vectors can be used, for example, to inhibit a *P. falciparum* infection.

18 Claims, 32 Drawing Sheets

Specification includes a Sequence Listing.

FIG. 1F

Heavy Chain Variable Region

|  |  | CDR1 |  | CDR2 |
|---|---|---|---|---|
| CIS04 | QVQLVQSGAEVKKPGASVKVSCKASGYTFTS | YAIH | WVRQAPGQRLEWMG | WIKAGNGDTRYSQKFQG |
| CIS06 | QVQLVQSGPEVKKPGTSVKVSCKASGFTFSS | SAVQ | WVRQARGQRLEWIG | WIVVGSGKTKYAQNFQQ |
| CIS23 | EVQLVESGGGVVQPGRSLRLSCAASGFTFSS | YGMY | WVRQAPGKGLEWVA | LISHDGSNKFYADSVKG |
| CIS34 | QVQLVESGGGVVQPGRSLRLSCAASGFTFSS | YGIH | WVRQAPGKGLEWVA | VIWYDGSKKYYGDSVKG |
| CIS42 | QVQLVQSGSELKKPGASVKVSCKTSGYTFTT | YAMN | WVRQAPGQGLEWMG | WINTNTGNPTYAPGFTG |
| CIS43 | QVQLVQSGAEVKKPGASVKVSCKASGYTFTS | YAIH | WVRQAPGQRLEWMG | WIKAGNGNTRYSQKFQD |
| mAb10 | EVQLVESGGGVVQPGRSLRLSCEASGFTFST | YGMH | WVRQAPGKGLEWVA | IIWHDGSKKYHADSVRG |

|  |  | CDR3 |  |
|---|---|---|---|
| CIS04 | RVTITRDTSATTAYMELSSLRSEDTAVYYCG | LLTVLTPDDAFDI | WGQGTMVTVSS |
| CIS06 | RVTITRDMSTSTAYLELSTLRSEDTAVYYCA | AVVNWNDESGFDP | WGQGTLVTVSS |
| CIS23 | RFTISRDNSKNTLYLQMNSLRAEDTAVYYCA | KDLGYSSSWGYFDY | WGQGTLVTVSS |
| CIS34 | RFTISRDNSKNTLYLQMNSLRVEDTAVYYCA | RAVIAATGTRGYWFDP | WGQGTLVTVSS |
| CIS42 | RVFSFDTSVSTAYLQISSLKAEDTAVYYCA | RVYSYGVPFDY | WGQGTLVTVSS |
| CIS43 | RVTITRDTSTTTAYMELSSLRSEDTAVYYCA | LLTVLTPDDAFDI | WGQGTMVTVSS |
| mAb10 | RFTISRDNSKNTLYLQMNSLRAEDTAVYFCA | RVGNYGGDWGAGFDY | WGQGTLVTVSS |

Light Chain Variable Region

| VL |  | CDR1 |  | CDR2 |
|---|---|---|---|---|
| CIS04 | DIVMTQSPDSLAVSLGERATINC | KSSQSVLYSSNNKNYLA | WYQQKPGQPPKLLIY | WASIRES |
| CIS06 | DIQMTQSPSSLSAFVGDRVTITC | RASQSIGTYLN | WYQQKVGQAPKLLIY | TASSLRS |
| CIS23 | EIVLTQSPATLSLSPGERATLSC | RASQSVSSYLA | WYQQKPGQAPRLLIY | DASNRAT |
| CIS34 | DIIMTQSPVSLSASVGDRVTITC | RASQSISSHLN | WYQQKPGKAPKLLIY | AASSLQS |
| CIS42 | QSVLTQPASVSGSPGQSITISC | TATSSNVGSFNLVS | WYQHHPGKAPKLIIH | EVSKRPS |
| CIS43 | DIVMTQSPDSLAVSLGERATINC | KSSQSVLYSSNNKNYLA | WYQQKPGQPPNLLIY | WASTRQS |
| mAb10 | DIQMTQSPSFLSASVGDRVTIAC | RASQSISSWLA | WYQQKPGKAPKLLIY | HASSLES |

| VL |  | CDR3 |  |
|---|---|---|---|
| CIS04 | GVPDRFSGSGSGTDFTLTISSLQAEDVAVYYC | HQYYSSPLT | FGGGTKVEIK |
| CIS06 | GVPSRFSGSGSGTDFTLTITSLQPEDFATYYC | QQSYSTYT | FGQGTKLEIK |
| CIS23 | GIPARFSGSGSGTDFTLTISSLEPEDFAVYYC | QQRSNWYT | FGQGTKLEIK |
| CIS34 | GVPSRFSGSGSGTDFTLTISSLQPEDFATYSC | QQTYRGFT | FAPGTKVDIK |
| CIS42 | GASNRFSGSKSGNTASLTISGLQAEDEADYYC | CSYVGSDTWV | FGGGTKLTVL |
| CIS43 | GVPDRFSGSGSGTDFTLTISSLQAEDVAVYYC | HQYYSSPLT | FGGGTKVEIK |
| mAb10 | GVPSRFSGSASGTEFALTISSLQPDDFATYYC | QQYSSYWT | FGQGTKVEIK |

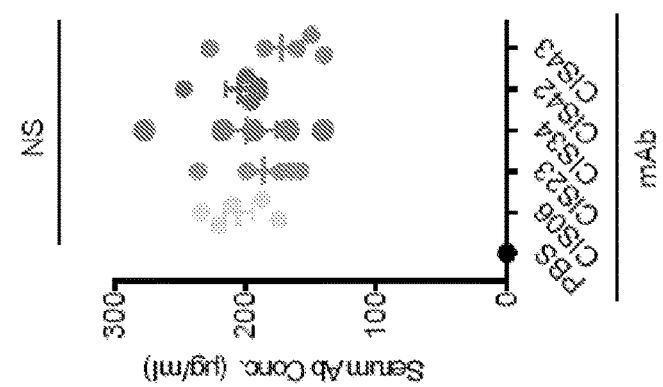
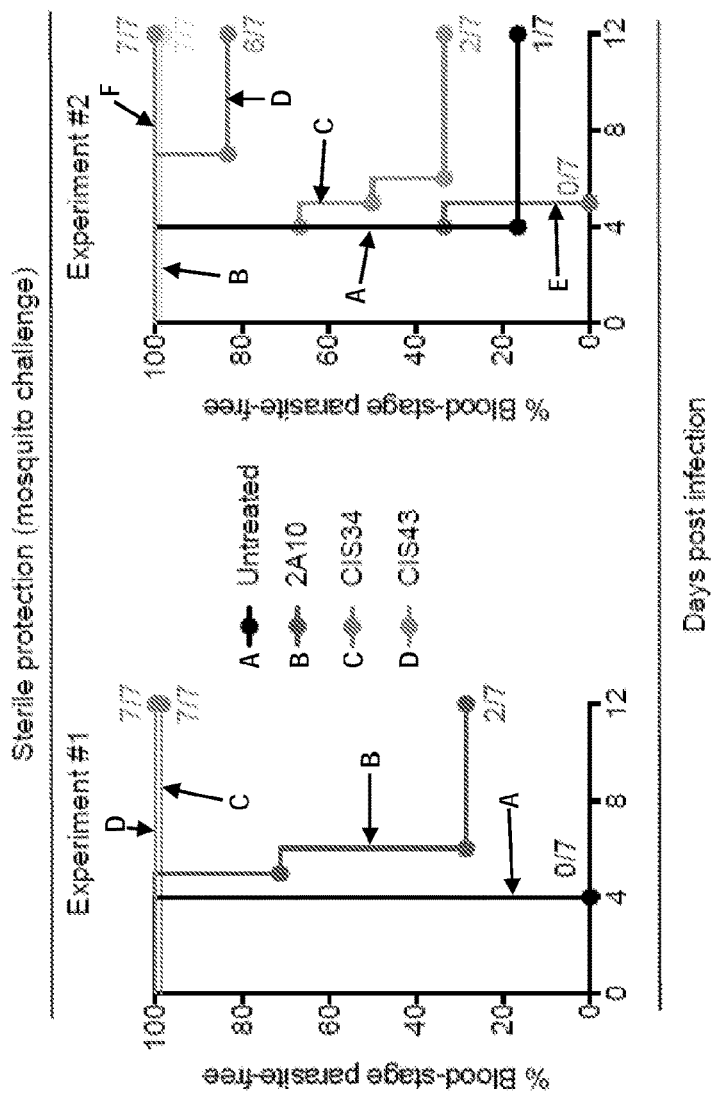
FIG. 2D
FIG. 2C

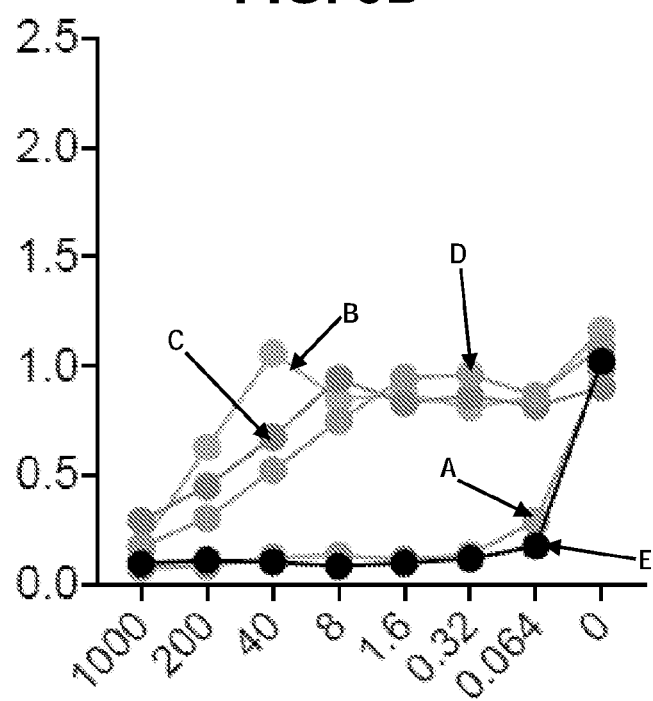

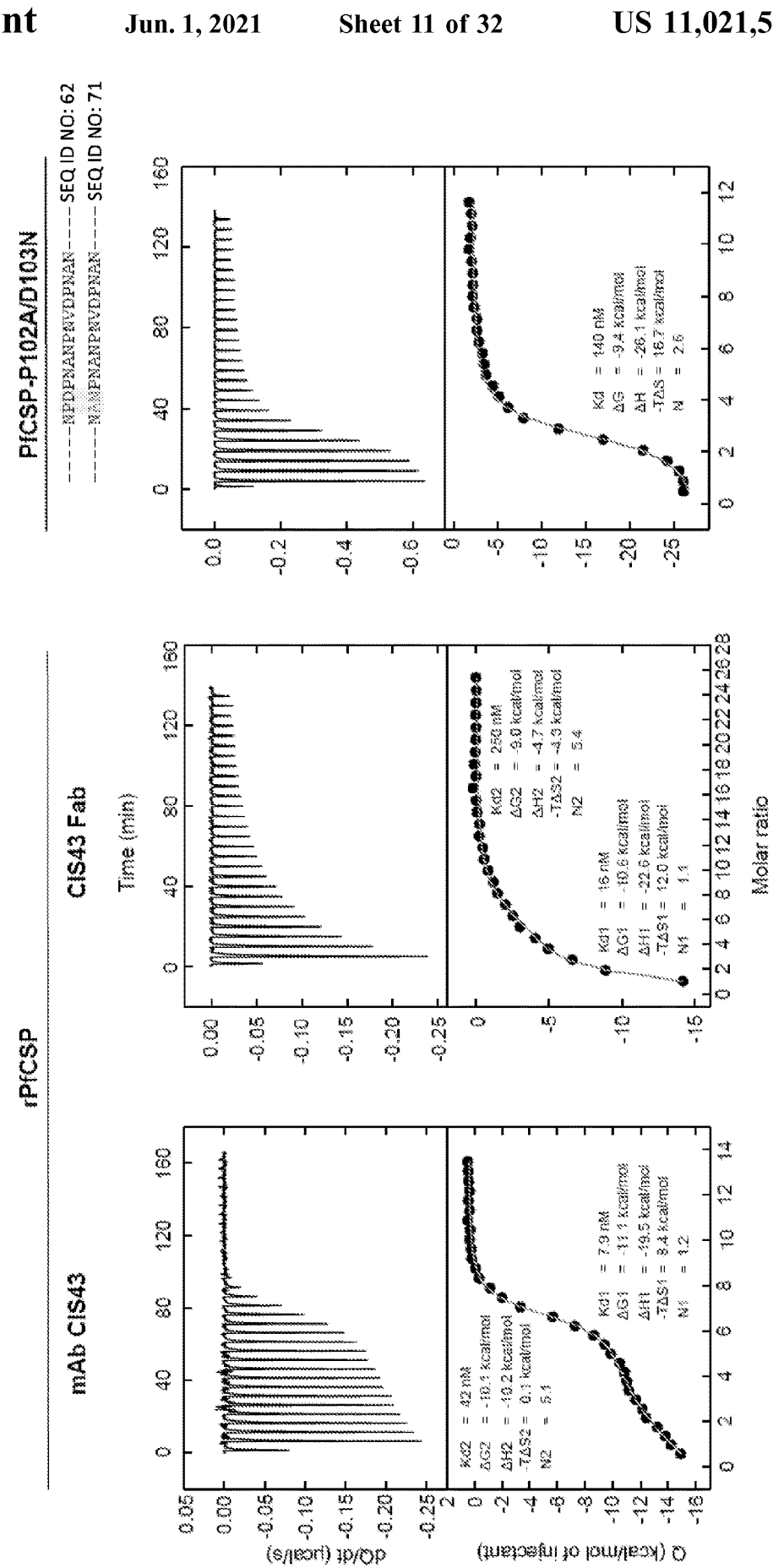

FIG. 4B

```
                              CDR H1                    CDR H2
              1        10        20    ┌──30──┐  40    50 52    60
CIS43 Heavy   QVQLVQSGAEVKKPGASVKVSCKASGYTFTSYAIHWVRQAPGQRLEWMGWIKAGNGNTRYS
IGHV1-3*01    ................................M....................N......K..
Peptide 20                               ** *                 *  * *         *
Peptide 21                               ** *                 *  * *         *
Peptide 25                               ** *                 *  * *         *
Peptide 29                               ** *                 *  * *
              ┌61     70        80 82    90       CDR H3       110
                                    ABC         ┌──100──┐
                                                    ABCD
CIS43 Heavy   QKFQDRVTITRDTSTTTAYMELSSLRSEDTAVYYCALLTVLTPDDAFDIWGQGTMVTVSS
IGHV1-3*01    ....G.........AS....................R......................
Peptide 20                                            ******
Peptide 21                                         *******
Peptide 25                                            ******
Peptide 29                                            ******
                                              CDR L1
              1        10        20   ┌─27──30──┐  40
                                        ABCDEF
CIS43 Kappa   DIVMTQSPDSLAVSLGERATINCKSSQSVLYSSNNKNYLAWYQQKPGQPPNLLIY
IGKV4-1*01    .....................................................K....
Peptide 20                             ** *           *
Peptide 21                             ** ** * *
Peptide 25                                *         *
Peptide 29                                * * *
              CDR L2                                 CDR L3
              ┌50─┐  60        70        80     ┌─90─┐    100
CIS43 Kappa   WASTRQSGVPDRFSGSGSGTDFTLTISSLQAEDVAVYYCHQYYSSPLTFGGGTKVEIK
IGKV4-1*01    .....E..................................Q....T.
Peptide 20    *                                       * ****  *
Peptide 21    *                                       * ****  *
Peptide 25    *                                       * ****  *
Peptide 29    *                                       * ****  *
```

|   | SEQ ID NO: |
|---|---|
| A — 20: PADGNPDPNANPNVD | 61 |
| B — 21: NPDPNANPNVDPNAN | 62 |
| C — 22: NANPNVDPNANPNVD | 63 |
| D — 25: NVDPNANPNVDPNAN | 66 |
| E — 27: NVDPNANPNANPNAN | 68 |
| F — 29: NANPNANPNANPNAN | 69 |
| G — 43: NANPNANPNVDPNAN | 71 |
| H — 44: NANPNVDPNANPNAN | 72 |
| I — 61: NANPNANPNANPNKN | 74 |

SEQ ID NO:
A —— 20: PADGNPDPNANPNVD 61
B —— 21: NPDPNANPNVDPNAN 62
C —— 22: NANPNVDPNANPNVD 63
D —— 25: NVDPNANPNVDPNAN 66
E —— 27: NVDPNANPNANPNAN 68
F —— 29: NANPNANPNANPNAN 69
G —— 43: NANPNANPNVDPNAN 71
H —— 44: NANPNVDPNANPNAN 72
I —— 61: NANPNANPNANPNKN 74

PfCSP mAbs bound to rPfCSP

FIG. 7A

```
CIS43   Heavy   QVQLVQSGAEVKKPGASVKVSCKASGYTFTSYAIHWVRQA
CIS43v  Heavy   QVQLVQSGAEVKKPGASVKVSCKASGYTFTSYAIHWVRQA CIS43   Heavy   PGQRLEWMGWIKAGNGNTRYSQKFQDRVTITRDTSTTTAY
CIS43v  Heavy   PGQRLEWMGWIKAGNGGGGYSGKFQDRVTITRDTSTTTAY CIS43   Heavy   MELSSLRSEDTAVYYCALLTVLTPDDAFDIWGQGTMVTVSS
CIS43v  Heavy   MELSSLRSEDTAVYYCALLTVLTPDDAFDIWGQGTMVTVSS
```

FIG. 7B

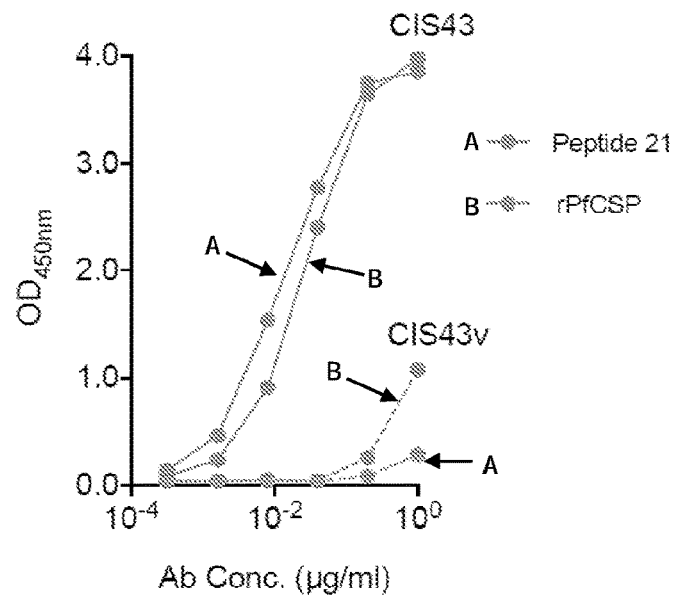

FIG. 7C

| CIS43 variant | |
|---|---|
| Mutation | Binding free-energy changes ($\Delta\Delta G$) (kcal/mol) |
| N56G | -0.01 |
| T57G | -0.01 |
| R58G | 1.7 |
| Q61G | 0 |
| N56G, T57G, R58G, Q61G | 1.4 |

FIG. 8A
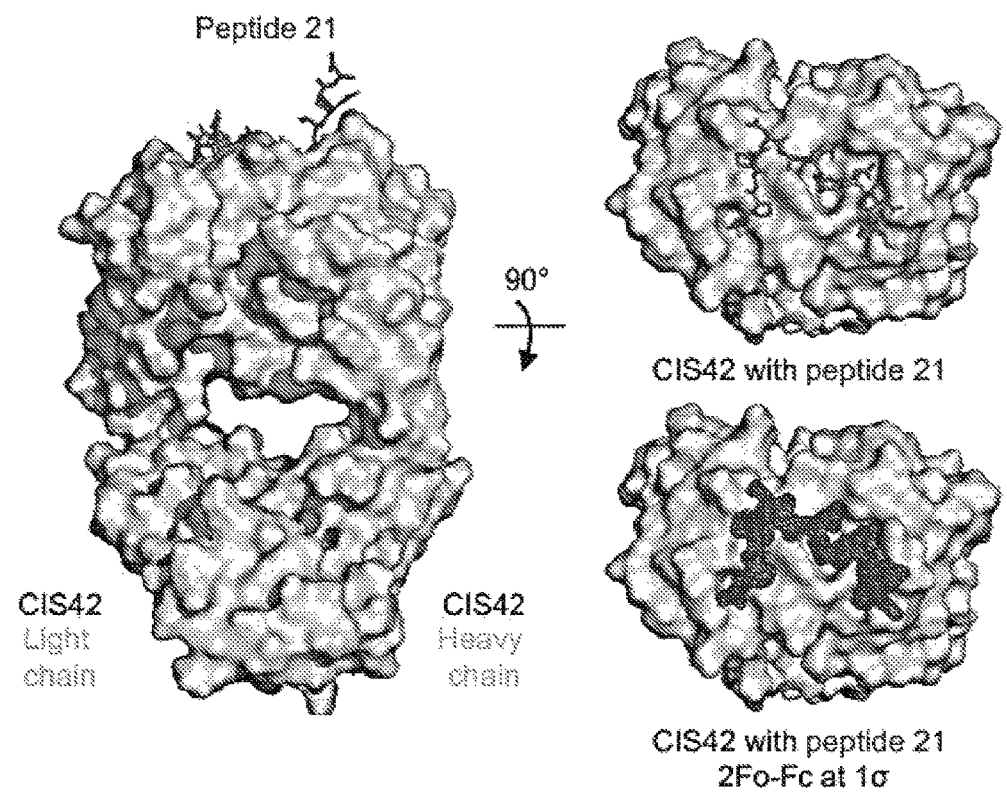
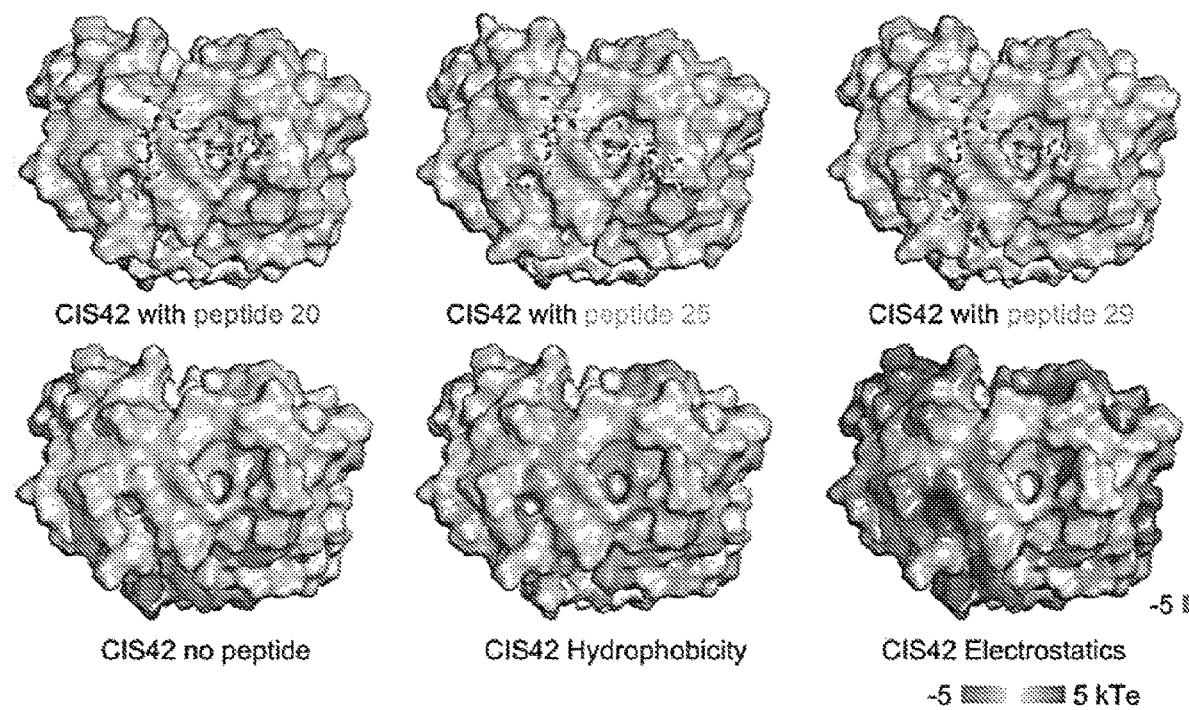

FIG. 9

PfCSP immunoglobulin V-gene family usage.

| mAb | V$_H$ | V$_H$ maturation (nt, %) | D | J$_H$ | CDRH3 length (aa) | V$_L$ | V$_L$ maturation (nt, %) | J$_L$ |
|---|---|---|---|---|---|---|---|---|
| CIS06 | VH1-58*01 | 4.2 | DH1-1*01 | JH5*02 | 14 | Vk1-39*01 | 11.1 | Jk2*01 |
| CIS23 | VH3-30*03 | 2.1 | DH6-13*01 | JH4*02 | 15 | Vk3-11*01 | 1.9 | Jk2*01 |
| CIS34 | VH3-33*01 | 2.8 | DH6-13*13 | JH5*02 | 17 | Vk1-39*01 | 3.7 | Jk3*01 |
| CIS42 | VH7-4-1*02 | 3.1 | DH5-18*01 | JH4*02 | 12 | Vλ2-23*02 | 3.5 | Jλ3*02 |
| CIS43 | VH1-3*01 | 3.8 | DH4-23*01 | JH3*02 | 14 | Vk4-1*01 | 2.9 | Jk4*01 |
| mAb04 | VH3-33*01 | 2.0 | DH3-22*01 | JH4*02 | 16 | Vk2D-29*01 | 0.0 | Jk2*01 |
| mAb09 | VH3-33*01 | 3.1 | DH3-22*01 | JH3*02 | 15 | Vk3-11*01 | 1.4 | Jk3*01 |
| mAb10 | VH3-33*01,04 | 3.3 | DH4-23*01 | JH4*02 | 16 | Vk1-5*01 | 1.7 | Jk1*01 |
| mAb15 | VH3-33*01 | 0.2 | DH3-22*01 | JH6*02 | 22 | Vk3-20*01 | 0.3 | Jk1*01 |
| mAb19 | VH6-1*01 | 1.1 | DH2-2*01 | JH1*01 | 13 | Vk4-1*01 | 1.1 | Jk4*01 |
| mAb21 | VH3-30*04 | 2.9 | DH2-1R2*01 | JH3*02 | 10 | Vλ2-8*01 | 0.6 | Jλ1*01 |
| mAb22 | VH3-33*01 | 0.5 | DH2-21*02 | JH4*02 | 19 | Vk3-20*01 | 0.0 | Jk3*01 |
| mAb25 | VH3-33*01 | 1.7 | DH6-13*01 | JH3*02 | 19 | Vk1-5*03 | 1.2 | Jk1*01 |
| mAb26 | VH3-48*03 | 0.7 | DH2-2*01 | JH4*02 | 18 | Vk1-5*03 | 0.3 | Jk1*01 |
| mAb27 | VH3-49*03 | 0.8 | DH6-13*01 | JH4*02 | 12 | Vk3-15*01 | 0.3 | Jk3*01 |
| mAb28 | VH4-34*12 | 3.7 | DH4-17*01 | JH4*01 | 13 | Vk1D-17*01 | 2.0 | Jk4*01 |
| mAb30 | VH3-33*01 | 1.5 | DH4-17*01 | JH4*02 | 16 | Vk1-5*03 | 0.0 | Jk1*01 |

V, variable region; H, heavy chain; L, light chain; κ, Kappa; λ, Lambda; nt, nucleotides; aa, amino acid. Yellow-highlighted, mAbs isolated from PfCSP-specific memory B cells. Non-highlighted, mAbs isolated from plasmablasts.

FIG. 10A

Detailed interactions of peptide 20 with Fab CIS43 Heavy chain.

| Peptide 20 | HSDC | ASA | BSA | | CIS43 Heavy | HSDC | ASA | BSA |
|---|---|---|---|---|---|---|---|---|
| A:ASN 1 | | 189.10 | 0.00 | | H:TYR 32 | | 49.76 | 7.29 |
| A:PRO 2 | | 122.29 | 0.00 | | H:ALA 33 | H | 26.51 | 25.02 |
| A:ASP 3 | S | 94.15 | 13.78 | | H:HIS 35 | | 31.33 | 22.80 |
| A:PRO 4 | | 110.73 | 0.00 | | H:TRP 47 | | 95.04 | 5.45 |
| A:ASN 5 | | 123.92 | 54.45 | | H:TRP 50 | | 49.23 | 39.99 |
| A:ALA 6 | | 88.82 | 24.95 | | H:LYS 52 | | 89.40 | 22.60 |
| A:ASN 7 | H | 71.29 | 41.44 | | H:ARG 58 | S | 155.13 | 70.70 |
| A:PRO 8 | | 120.80 | 69.85 | | H:THR 95 | | 44.77 | 11.09 |
| A:ASN 9 | H | 137.55 | 132.43 | | H:VAL 97 | | 97.33 | 26.46 |
| A:VAL 10 | | 162.51 | 52.43 | | H:LEU 98 | H | 12.38 | 12.38 |
| | | | | | H:LEU 98 | | 134.71 | 45.15 |
| | | | | | H:THR 99 | | 56.84 | 7.93 |

| Hydrogen Bonds | | |
|---|---|---|
| Peptide 20 | Dist.[Å] | CIS43 Heavy |
| A:ASN 7[HD21] | 1.84 | H:LEU 95[ O ] |
| A:ASN 9[HD21] | 2.23 | H:ALA 33[ O ] |
| A:ASN 9[HD22] | 2.33 | H:LEU 95[ O ] |
| A:ASN 9[ O ] | 2.03 | H:LEU 98[ H ] |
| A:ASN 9[ OD1] | 1.86 | H:ALA 33[ H ] |

| Salt Bridges | | |
|---|---|---|
| Peptide 20 | Dist.[Å] | CIS43 Heavy |
| A:ASP 3[ OD1] | 4.00 | H:ARG 58[ NH1] |
| A:ASP 3[ OD2] | 3.74 | H:ARG 58[ NH1] |

Detailed interactions of peptide 20 with Fab CIS43 Light chain.

| Peptide 20 | HSDC | ASA | BSA | | CIS43 Kappa | HSDC | ASA | BSA |
|---|---|---|---|---|---|---|---|---|
| A:ASN 1 | H | 189.10 | 45.59 | | L:TYR 27D | | 110.16 | 39.99 |
| A:PRO 2 | | 122.29 | 104.31 | | L:TYR 32 | | 43.77 | 23.67 |
| A:ASP 3 | H | 94.15 | 31.27 | | L:TRP 50 | | 83.36 | 15.48 |
| A:PRO 4 | | 110.73 | 0.00 | | L:HIS 89 | | 12.52 | 1.92 |
| A:ASN 5 | | 123.92 | 1.72 | | L:TYR 91 | | 63.33 | 38.63 |
| A:ALA 6 | | 88.82 | 63.87 | | L:TYR 92 | H | 85.81 | 70.54 |
| A:ASN 7 | | 71.29 | 29.85 | | L:SER 93 | | 37.03 | 9.52 |
| A:PRO 8 | | 120.80 | 0.00 | | L:SER 94 | | 101.08 | 35.11 |
| A:ASN 9 | | 137.55 | 0.00 | | L:LEU 96 | | 110.28 | 39.75 |
| A:VAL 10 | | 162.51 | 86.59 | | | | | |

| Hydrogen Bonds | | |
|---|---|---|
| Peptide 20 | Dist.[Å] | CIS43 Kappa |
| A:ASN 1[ H2 ] | 2.12 | L:TYR 92[ OH ] |
| A:ASP 3[ H ] | 2.09 | L:TYR 92[ O ] |

ASA Accessible Surface Area, Å²   BSA Buried Surface Area, Å²   ||||  Buried area percentage, one bar per 10%

FIG. 10B

Detailed interactions of peptide 21 with Fab CIS43 Heavy chain

| Peptide 21 | HSDC | ASA | BSA | | CIS43 Heavy | HSDC | ASA | BSA |
|---|---|---|---|---|---|---|---|---|
| A:ASN 1 | H | 197.81 | 0.00 | | H:TYR 32 | | 48.21 | 8.36 |
| A:PRO 2 | | 115.38 | 0.00 | | H:ALA 33 | H | 29.54 | 27.97 |
| A:ASP 3 | HS | 92.88 | 17.62 | | H:HIS 35 | | 31.43 | 22.85 |
| A:PRO 4 | | 106.04 | 0.00 | | H:TRP 47 | | 86.08 | 4.68 |
| A:ASN 5 | H | 119.08 | 38.95 | | H:TRP 50 | | 48.69 | 39.15 |
| A:ALA 6 | | 83.90 | 24.56 | | H:LYS 52 | | 88.74 | 15.06 |
| A:ASP 7 | H | 73.57 | 42.01 | | H:ARG 58 | HS | 157.64 | 72.32 |
| A:PRO 8 | | 106.49 | 65.50 | | H:LEU 95 | | 42.93 | 11.66 |
| A:ASN 9 | H | 133.27 | 127.72 | | H:THR 96 | | 84.94 | 27.61 |
| A:VAL 10 | | 91.87 | 32.16 | | H:VAL 97 | H | 11.72 | 11.72 |
| A:ASP 11 | H | 130.57 | 53.62 | | H:LEU 98 | | 136.62 | 50.40 |
| A:PRO 12 | | 118.00 | 0.00 | | H:THR 99 | | 51.70 | 14.85 |
| A:ASN 13 | | 180.11 | 0.00 | | H:PRO 100 | | 151.25 | 26.95 |

Hydrogen Bonds

| Peptide 21 | Dist. [Å] | CIS43 Heavy chain |
|---|---|---|
| A:ASN 7[HD21] | 2.12 | H:LEU 95[ O ] |
| A:ASN 9[HD21] | 2.43 | H:ALA 33[ O ] |
| A:ASN 9[HD22] | 2.28 | H:LEU 95[ O ] |
| A:ASP 11[ H ] | 2.11 | H:LEU 98[ O ] |
| A:ASP 3[ OD2] | 2.30 | H:ARG 58[HH12] |
| A:ASN 9[ O ] | 2.14 | H:LEU 98[ H ] |
| A:ASN 9[ OD3] | 2.13 | H:ALA 33[ H ] |

Salt Bridges

| Peptide 21 | Dist. [Å] | CIS43 Heavy chain |
|---|---|---|
| A:ASP 3[ OD2] | 2.95 | H:ARG 58[ NH1] |
| A:ASP 3[ OD2] | 3.49 | H:ARG 58[ NH2] |

Detailed interactions of peptide 21 with Fab CIS43 Light chain

| Peptide 21 | HSDC | ASA | BSA | | CIS43 Kappa | HSDC | ASA | BSA |
|---|---|---|---|---|---|---|---|---|
| A:ASN 1 | H | 197.81 | 63.98 | | L:LEU 27C | | 50.03 | 1.10 |
| A:PRO 2 | H | 115.38 | 95.18 | | L:TYR 27D | | 110.66 | 54.04 |
| A:ASP 3 | | 92.88 | 36.24 | | L:SER 27F | | 89.14 | 3.83 |
| A:PRO 4 | | 106.04 | 0.00 | | L:ASN 28 | | 55.06 | 18.51 |
| A:ASN 5 | | 119.08 | 1.12 | | L:LYS 30 | | 82.68 | 12.33 |
| A:ALA 6 | | 83.90 | 59.34 | | L:TYR 32 | | 43.71 | 38.24 |
| A:ASP 7 | | 73.57 | 31.56 | | L:TRP 50 | | 82.52 | 30.72 |
| A:PRO 8 | | 106.49 | 0.00 | | L:HIS 89 | | 11.34 | 1.00 |
| A:ASN 9 | | 133.27 | 0.00 | | L:TYR 91 | | 63.18 | 38.20 |
| A:VAL 10 | | 91.87 | 53.83 | | L:TYR 92 | H | 83.80 | 67.99 |
| A:ASP 11 | | 130.57 | 11.40 | | L:SER 93 | | 46.55 | 12.29 |
| A:PRO 12 | | 118.00 | 54.25 | | L:SER 94 | | 104.12 | 45.35 |
| A:ASN 13 | | 180.11 | 7.14 | | L:LEU 96 | | 108.83 | 38.01 |

Hydrogen Bonds

| Peptide 21 | Dist. [Å] | CIS43 Kappa |
|---|---|---|
| A:ASN 1[ H2 ] | 1.68 | L:TYR 92[ OH ] |
| A:ASP 3[ H ] | 2.05 | L:TYR 92[ O ] |

ASA Accessible Surface Area, Å²  BSA Buried Surface Area, Å²  ||||  Buried area percentage, one bar per 10%

FIG. 10C

Detailed interactions of peptide 25 with CIS43 Fab heavy chain.

| Peptide 25 | HSDC | ASA | BSA |
|---|---|---|---|
| A:ASN 1 | | 204.22 | 0.00 |
| A:VAL 2 | HS | 139.38 | 0.00 |
| A:ASP 3 | | 84.63 | 24.76 |
| A:PRO 4 | | 102.14 | 0.00 |
| A:ASN 5 | | 116.90 | 47.76 |
| A:ALA 6 | | 88.13 | 24.36 |
| A:ASP 7 | H | 68.20 | 41.09 |
| A:PRO 8 | | 108.76 | 67.35 |
| A:ASN 9 | H | 136.18 | 125.57 |
| A:VAL 10 | | 105.11 | 39.98 |
| A:ASP 11 | H | 187.37 | 41.71 |

| CIS43 Heavy | HSDC | ASA | BSA |
|---|---|---|---|
| H:TYR 32 | | 73.77 | 5.50 |
| H:ALA 33 | H | 51.34 | 28.38 |
| H:HIS 35 | | 30.06 | 22.23 |
| H:TRP 47 | | 87.45 | 5.62 |
| H:TRP 50 | | 54.24 | 43.70 |
| H:CYS 52 | | 90.55 | 32.47 |
| H:ARG 58 | HS | 157.34 | 53.76 |
| H:LEU 95 | | 47.19 | 11.71 |
| H:THR 96 | | 82.91 | 28.06 |
| H:VAL 97 | | 25.90 | 18.25 |
| H:LEU 98 | H | 125.95 | 50.45 |
| H:THR 99 | | 73.37 | 6.69 |
| H:PRO 100 | | 140.90 | 13.39 |

Hydrogen Bonds

| Peptide 25 | Dist. [Å] | CIS43 Heavy chain |
|---|---|---|
| A:ASN 7[HD21] | 2.20 | H:LEU 95[ O ] |
| A:ASN 9[HD22] | 1.96 | H:ALA 33[ O ] |
| A:ASN 9[HD22] | 2.33 | H:LEU 95[ O ] |
| A:ASP 11[ H ] | 2.33 | H:LEU 98[ O ] |
| A:ASP 3[ OD2] | 2.42 | H:ARG 58[NH22] |
| A:ASN 9[ O ] | 2.28 | H:LEU 98[ H ] |
| A:ASN 9[ OD1] | 2.03 | H:ALA 33[ H ] |

Salt Bridges

| Peptide 25 | Dist. [Å] | CIS43 Heavy chain |
|---|---|---|
| A:ASP 3[ OD1] | 3.89 | H:ARG 58[ NH1] |
| A:ASP 3[ OD2] | 3.05 | H:ARG 58[ NH1] |
| A:ASP 3[ OD2] | 3.25 | H:ARG 58[ NH2] |

Detailed interactions of peptide 25 with Fab CIS43 Light chain.

| Peptide 25 | HSDC | ASA | BSA |
|---|---|---|---|
| A:ASN 1 | | 204.22 | 49.19 |
| A:VAL 2 | | 139.38 | 111.89 |
| A:ASP 3 | H | 84.63 | 32.89 |
| A:PRO 4 | | 102.14 | 0.00 |
| A:ASN 5 | | 116.90 | 1.54 |
| A:ALA 6 | | 88.13 | 63.77 |
| A:ASP 7 | | 68.20 | 27.12 |
| A:PRO 8 | | 108.76 | 0.00 |
| A:ASN 9 | | 136.18 | 0.00 |
| A:VAL 10 | | 105.11 | 64.61 |
| A:ASP 11 | | 187.37 | 5.57 |

| CIS43 Kappa | HSDC | ASA | BSA |
|---|---|---|---|
| L:TYR 27D | | 102.41 | 36.16 |
| L:TYR 32 | | 40.82 | 25.92 |
| L:TYR 50 | | 72.36 | 21.10 |
| L:HIS 89 | | 14.47 | 3.09 |
| L:TYR 91 | | 61.22 | 38.35 |
| L:TYR 92 | H | 91.82 | 68.34 |
| L:SER 93 | | 42.53 | 16.86 |
| L:SER 94 | | 102.72 | 40.17 |
| L:LEU 96 | | 104.59 | 36.51 |

Hydrogen Bonds

| Peptide 25 | Dist. [Å] | CIS43 Kappa |
|---|---|---|
| A:ASP 3[ H ] | 2.09 | L:TYR 92[ O ] |

ASA Accessible Surface Area, Å²    BSA Buried Surface Area, Å²    ||||  Buried area percentage, one bar per 10%

FIG. 10D

Detailed interactions of peptide 29 with Fab CIS43 Heavy chain.

| Peptide 29 | HSDC | ASA | BSA | NK43 heavy chain | HSDC | ASA | BSA | Hydrogen Bonds Peptide 29 | | Dist. [Å] | NK43 heavy chain |
|---|---|---|---|---|---|---|---|---|---|---|---|
| A:ASN 3 | | 152.02 | 0.00 | H:TYR 32 | | 70.79 | 8.03 | A:ASN 7 | H:O 21 | 1.87 | H:LEU 95 | O |
| A:PRO 4 | | 112.17 | 0.00 | H:ALA 33 | | 28.80 | 27.39 | A:ASN 9 | H:O 21 | 1.99 | H:ALA 33 | O |
| A:ASN 5 | | 157.68 | 1.97 | H:HIS 35 | | 32.94 | 23.54 | A:ASN 9 | O 1 | 2.22 | H:LEU 95 | H |
| A:ALA 6 | | 77.61 | 11.11 | H:TRP 50 | | 53.65 | 33.85 | A:ASN 9 | CD 1 | 2.10 | H:ALA 33 | H |
| A:ASN 7 | H | 80.26 | 48.53 | H:LYS 52 | | 93.44 | 18.67 | | | | |
| A:PRO 8 | | 129.13 | 78.52 | H:LEU 94 | | 0.45 | 0.45 | | | | |
| A:ASN 9 | H | 136.85 | 137.93 | H:LEU 95 | | 42.46 | 10.80 | | | | |
| A:ALA 10 | | 69.61 | 29.58 | H:THR 96 | | 89.48 | 29.30 | | | | |
| A:ASN 11 | | 190.99 | 40.11 | H:VAL 97 | | 19.03 | 15.73 | | | | |
| | | | | H:LEU 98 | H | 125.94 | 49.24 | | | | |
| | | | | H:THR 99 | | 67.65 | 4.33 | | | | |
| | | | | H:PRO 100 | | 142.86 | 11.88 | | | | |

Detailed interactions of peptide 29 with Fab CIS43 Light chain.

| Peptide 29 | HSDC | ASA | BSA | NK43 Kappa | HSDC | ASA | BSA | Hydrogen Bonds Peptide 29 | | Dist. [Å] | NK43 light chain |
|---|---|---|---|---|---|---|---|---|---|---|---|
| A:ASN 3 | | 152.02 | 50.02 | L:TYR 27D | | 91.00 | 44.32 | A:ALA 6 | O 1 | 3.89 | L:SER 94 | OG |
| A:PRO 4 | | 112.17 | 74.83 | L:ASN 28 | | 58.18 | 5.25 | | | | |
| A:ASN 5 | | 157.68 | 49.31 | L:LYS 30 | | 78.39 | 10.87 | | | | |
| A:ALA 6 | H | 77.61 | 62.66 | L:TYR 32 | | 42.26 | 33.09 | | | | |
| A:ASN 7 | | 80.26 | 33.73 | L:TRP 50 | | 75.38 | 29.47 | | | | |
| A:PRO 8 | | 129.13 | 0.00 | L:HIS 89 | | 11.69 | 2.17 | | | | |
| A:ASN 9 | | 136.85 | 0.00 | L:TYR 91 | | 57.24 | 33.66 | | | | |
| A:ALA 10 | | 69.61 | 40.20 | L:TYR 92 | | 87.31 | 59.89 | | | | |
| A:ASN 11 | | 190.99 | 44.54 | L:SER 93 | | 40.13 | 15.12 | | | | |
| | | | | L:SER 94 | H | 98.77 | 39.18 | | | | |
| | | | | L:LEU 96 | | 105.03 | 30.65 | | | | |

ASA Accessible Surface Area, Å²  BSA Buried Surface Area, Å²  |||| Buried area percentage, one bar per 10%

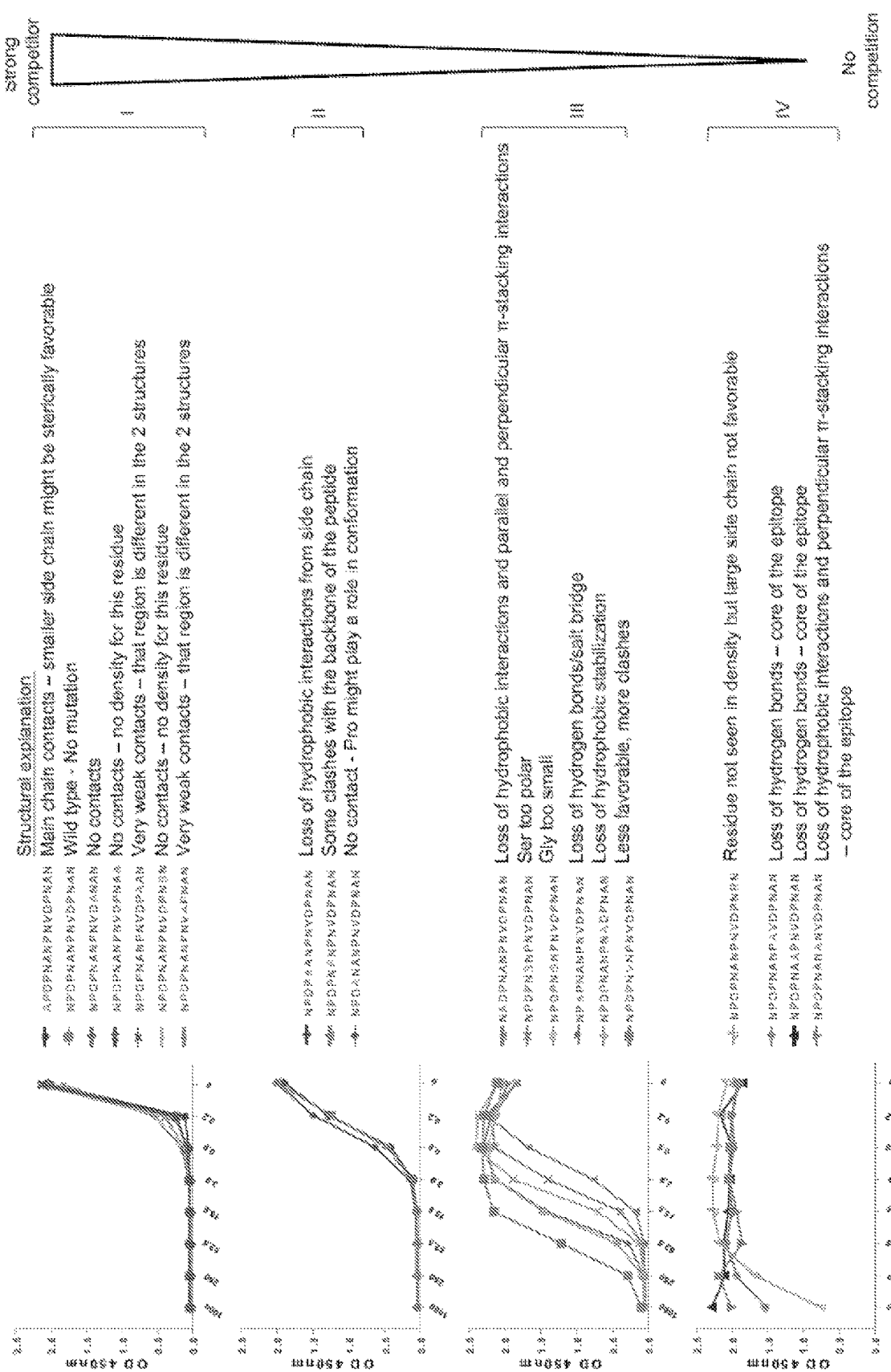

NEUTRALIZING ANTIBODIES TO PLASMODIUM FALCIPARUM CIRCUMSPOROZOITE PROTEIN AND THEIR USE

CROSS REFERENCE TO RELATED APPLICATIONS

This application is the U.S. National Stage of International Application No. PCT/US2018/017826, which was published in English under PCT Article 21(2), which in turn claims the benefit of U.S. Provisional Application No. 62/457,720, filed Feb. 10, 2017. The provisional application is incorporated herein in its entirety.

FIELD

This relates to monoclonal antibodies and antigen binding fragments that specifically bind to *Plasmodium falciparum* (*P. falciparum* or Pf) circumsporozoite protein (CSP) and their use, for example, in methods of inhibiting *P. falciparum* infection in a subject.

BACKGROUND

Malaria ranks as one of the world's top deadliest infectious diseases, with approximately 300 million cases per year. Malaria in humans is caused by five species of the *Plasmodium* parasite: *P. falciparum*, *P. vivax*, *P. ovale*, *P. knowlesi* and *P. malariae*. *P. falciparum* causes the most severe form of malaria disease, leading to the death of about ~500,000 people annually, most of whom are young children.

Each of the *Plasmodium* species that infect humans is transmitted through the bite of an infected female *Anopheles* mosquito, which introduces *Plasmodium* sporozoites into the bloodstream of the human host. The major protein on the surface of the infecting sporozoites is CSP. The sporozoites rapidly reach the liver where they are sequestered by hepatocytes and undergo asexual expansion. One week later, the infected hepatocytes rupture and release mature parasites, the merozoites. These then begin the erythrocytic phase of malaria by attaching to and invading red blood cells, or erythrocytes. The invasion of the erythrocytes by the malarial parasites leads to malarial pathogenesis and clinical infection.

There is no FDA approved vaccine for malaria. Moreover, malarial parasites are increasingly becoming resistant to antimalarial drugs used to treat the disease. Therefore, preventive interventions to inhibit malaria infection are urgently needed.

SUMMARY

This disclosure provides monoclonal antibodies and antigen binding fragments directed against the *Plasmodium falciparum* (Pf) circumsporozoite protein (PfCSP). Data shows that passive transfer of these antibodies, including the CIS43 antibody, confers sterile protection in multiple animal models of malaria infection.

In some embodiments, the antibody or antigen binding fragment comprises a heavy chain variable region ($V_H$) comprising a HCDR1, a HCDR2, and a HCDR3 of the $V_H$ set forth as SEQ ID NO: 1 (CIS04 $V_H$) and a light chain variable region ($V_L$) comprising a LCDR1, a LCDR2, and a LCDR3 of the $V_L$ set forth as SEQ ID NO: 2 (CIS04 $V_L$). In some embodiments, the antibody or antigen binding fragment comprises a $V_H$ comprising a HCDR1, a HCDR2, and a HCDR3 of the $V_H$ set forth as SEQ ID NO: 3 (CIS06 $V_H$) and a $V_L$ comprising a LCDR1, a LCDR2, and a LCDR3 of the $V_L$ set forth as SEQ ID NO: 4 (CIS06 $V_L$). In some embodiments, the antibody or antigen binding fragment comprises a $V_H$ comprising a HCDR1, a HCDR2, and a HCDR3 of the $V_H$ set forth as SEQ ID NO: 5 (CIS23 $V_H$) and a $V_L$ comprising a LCDR1, a LCDR2, and a LCDR3 of the $V_L$ set forth as SEQ ID NO: 6 (CIS23 $V_L$). In some embodiments, the antibody or antigen binding fragment comprises a $V_H$ comprising a HCDR1, a HCDR2, and a HCDR3 of the $V_H$ set forth as SEQ ID NO: 7 (CIS34 $V_H$) and a $V_L$ comprising a LCDR1, a LCDR2, and a LCDR3 of the $V_L$ set forth as SEQ ID NO: 8 (CIS34 $V_L$). In some embodiments, the antibody or antigen binding fragment comprises a $V_H$ comprising a HCDR1, a HCDR2, and a HCDR3 of the $V_H$ set forth as SEQ ID NO: 9 (CIS42 $V_H$) and a $V_L$ comprising a LCDR1, a LCDR2, and a LCDR3 of the $V_L$ set forth as SEQ ID NO: 10 (CIS42 $V_L$). In some embodiments, the antibody or antigen binding fragment comprises a $V_H$ comprising a HCDR1, a HCDR2, and a HCDR3 of the $V_H$ set forth as SEQ ID NO: 11 (CIS43 $V_H$) and a $V_L$ comprising a LCDR1, a LCDR2, and a LCDR3 of the $V_L$ set forth as SEQ ID NO: 12 (CIS43 $V_L$). In some embodiments, the antibody or antigen binding fragment comprises a $V_H$ comprising a HCDR1, a HCDR2, and a HCDR3 of the $V_H$ set forth as SEQ ID NO: 81 (mAb10 $V_H$) and a $V_L$ comprising a LCDR1, a LCDR2, and a LCDR3 of the $V_L$ set forth as SEQ ID NO: 82 (mAb10 $V_L$).

Also disclosed are compositions including the antibodies and antigen binding fragments, nucleic acids encoding the antibodies and antigen binding fragments, expression vectors comprising the nucleic acids, and isolated host cells that comprise the nucleic acids. In several embodiments, the nucleic acid molecule encoding a disclosed antibody or antigen binding fragment can be a cDNA molecule that encodes the antibody or antigen binding fragment. In additional embodiments, the nucleic acid molecule can be a bicistronic expression construct encoding the $V_H$ and $V_L$ of the antibody or antigen binding fragment.

The disclosed antibodies and antigen binding fragments potently neutralize *P. falciparum* and inhibit *P. falciparum* infection in accepted in vitro and in vivo models. Accordingly, a method is disclosed for inhibiting (including preventing) *P. falciparum* infection in a subject. The method comprises administering an effective amount (that is, an amount effective to inhibit *P. falciparum* infection in a subject) of one or more of the disclosed antibodies, antigen binding fragments, nucleic acid molecules, vectors, or compositions, to the subject, such as a subject at risk of or having a *P. falciparum* infection.

The antibodies, antigen binding fragments, nucleic acid molecules, vectors, and compositions disclosed herein can be used for a variety of additional purposes, such as for diagnosing *P. falciparum* infection in a subject, or detecting *P. falciparum* in a sample The foregoing and other features and advantages of this disclosure will become more apparent from the following detailed description of several embodiments, which proceeds with reference to the accompanying figures.

BRIEF DESCRIPTION OF THE FIGURES

FIGS. 1A-1F. Isolation and binding specificity of mAbs from rPfCSP specific-memory B cells. FIG. 1A, Schematic representation of rPfCSP (residues 21-375). Signal (1-21) and anchor (375-397) residues are excluded. The N-, C-terminal, and repeat domains are shown. The conserved region I (RI) is indicated. FIG. 1B, Gating strategy for sorting rPfCSP and (NANP)$_9$ (SEQ ID NO: 79) memory B cells. rPfCSP-specific, CD19+ IgG+ CD27+ memory B cells from pre-vaccination or after the 5th (last) vaccination. FIG. 1C, Binding of varying concentrations of mAbs to rPfCSP by ELISA. OD405 nm, optical density at 405 nm. FIG. 1D, Binding of mAbs to PfSPZ by ELISA. FIG. 1E, Binding of mAbs to PfSPZ by immunofluorescence assay (IFA). Phase contrast and fluorescence channels are shown. Scale bar, 10 µm. In FIGS. 1C-1E, Negative controls: Mock, transfection filtrate; VRC01, a human anti-HIV-1 IgG1 isotype control mAb. Positive control: 2A10, mouse anti-PfCSP repeat mAb. (FIG. 1F) Sequence alignment of the heavy and light chain variable regions of the CSP-specific CIS04, CIS06, CIS23, CIS34, CIS42, CIS43, and mAb10 antibodies, with CDRs according to kabat positioning indicated. The heavy and light chain variable region sequences are SEQ ID NOs: 1 and 2 (CIS04), 3 and 4 (CIS06), 5 and 6 (CIS23), 7 and 8 (CIS34), 9 and 10 (CIS42), 11 and 12 (CIS43), and 81 and 82 (mAb10).

FIGS. 2A-2G. Protection against malaria infection by PfCSP mAbs. FIG. 2A, Protective effect of PfCSP mAbs isolated from PfCSP-specific memory B cells on liver burden. Following passive transfer of the indicated mAbs, C57BL/6 mice (n=5/group) were challenged intravenously (IV) with chimeric PbSPZ expressing PfCSP (Pb-PfCSP). Liver burden is expressed as Pb 18s ribosomal RNA (rRNA) copies/mL. Significance is denoted with * p<0.016, and ** p<0.008, and NS=not significant. (*) on top refer to comparison to the untreated group. Brackets reflect comparison between mAb CIS43 and mAb2A10. FIG. 2B, Protective effect of PfCSP mAbs isolated from plasmablasts on liver burden as in FIG. 2A. Brackets reflect comparison between mAb CIS43 and mAb2A10 or mAb10 (** p<0.008). FIG. 2C, Sterile protection by PfCSP mAbs following Pb-PfCSP SPZ infection by mosquito bite. C57BL/6 mice challenged with 5 infected mosquitoes following passive transfer (300 µg) of the indicated mAbs. Kaplan Meier curves show frequencies of mice free of parasites as determined by Giemsa staining of blood. Differences between mAbs CIS43, CIS34 and mAb10 as compared to untreated mice were statistically significant (p<0.0001). FIG. 2D, Serum PfCSP mAb levels were assessed one hour after passive transfer of 300 µg of the indicated mAbs by ELISA against rPfCSP in a separate group of C57BL/6 mice (n=5/group). FIG. 2E, Protective effect of mAb CIS43 on parasite liver burden following Pf infection in FRG-huHep mice. Mice were challenged with 50 mosquitoes infected with Pf expressing GFP-luciferase, and parasite burden was determined 6 days later by bioluminescent imaging (flux). Results were normalized to mice receiving a non-specific IgG (Mock). Mock, n=12 mice; mAb CIS43 150 and 30 µg, n=7 and 6 mice, respectively. * p<0.041 and  p<0.001. FIG. 2F, Sterile protection by PfCSP mAbs following PfSPZ infection by mosquito bite. Following passive transfer (50 µg) of the indicated mAbs, FRG-huHep mice challenged with 5 infected mosquitoes. Kaplan Meier curves show frequencies of mice free of parasites as determined by Pf 18s rRNA on day 7 and 9. In both experiments mAb CIS43 was significantly more protective than untreated mice (p<0.0002). FIG. 2G, Serum PfCSP mAb levels in FRG-huHep mice (shown in FIG. 2F, Exp. #1 and #2) were assessed by ELISA against rPfCSP at time of challenge ( p<0.001).

FIGS. 3A-3F. Epitope mapping and ITC analysis of mAb CIS43. FIG. 3A, Binding of mAb CIS43 to overlapping peptides of PfCSP, with specified sequences numbered and color coded 20-61 (representing amino acid residues 97-276) by ELISA. Peptides 28-41 and 46-60, consist only of NANP repeats, and are represented by peptide 29. FIG. 3B, Binding of mAb CIS43 to rPfCSP in the presence of varying concentrations of peptides. The sequence of CIS43 $V_H$ (SEQ ID NO: 11) and $V_L$ (SEQ ID NO: 12) is shown. FIG. 3C, Binding of mAb CIS43 to rPfCSP in the presence of peptide 21 sequence variants. Wild type peptide 21 sequence with numeric position listed and mutated residues highlighted. FIG. 3D, Binding of mAb CIS43 to PfSPZ in the presence of peptide 21 and its sequence variants. FIG. 3E, ITC of mAb CIS43 and CIS43 Fab binding to rPfCSP. FIG. 3F, ITC of mAb CIS43 binding to PfCSP mutant, PfCSP(P102A, D103N), with changes in the junctional epitope sequence depicted in grey and highlighted. Upper panels show the output signal, dQ/dt, as a function of time. Lower panels show the integrated heats as a function of the antibody-site/PfCSP molar ratio in the cell. The solid line represents the result from best non-linear least squares fit of the data to a binding model that takes into account two sets of sites with different affinities for rPfCSP. Data shown are representative of three independent experiments. Dissociation constant (Kd), changes in Gibbs energy (ΔG) of binding, enthalpy (ΔH) and entropy (−TΔS) and stoichiometry (N) are shown. The sequences shown in FIGS. 3C and 3D are as follows: SEQ ID NO: 62 (NPDPNANPNVDPNAN), SEQ ID NO: 94 (APDPNANPNVDPNAN), SEQ ID NO: 95 (NADPNANPNVDPNAN), SEQ ID NO: 96 (NPAPNANPNVDPNAN), SEQ ID NO: 97 (NPDANANPNVDPNAN), SEQ ID NO: 98 (NPDPAANPNVDPNAN), SEQ ID NO: 99 (NPDPNSNPNVDPNAN), SEQ ID NO: 100 (NPDPNAAPNVDPNAN), SEQ ID NO: 101 (NPDPNANANVDPNAN), SEQ ID NO: 102 (NPDPNANPAVDPNAN), SEQ ID NO: 103 (NPDPNANPNADPNAN), SEQ ID NO: 104 (NPDPNANPNVAPNAN), SEQ ID NO: 105 (NPDPNANPNVDANAN), SEQ ID NO: 106 (NPDPNANPNVDPAAN), SEQ ID NO: 107 (NPDPNANPNVDPNSN), SEQ ID NO: 108 (NPDPNANPNVDPNRN), SEQ ID NO: 109 (NPDPNANPNVDPNAA), SEQ ID NO: 110 (NPDPNGNPNVDPNAN), SEQ ID NO: 111 (NPDPNVNPNVDPNAN), SEQ ID NO: 112 (NPDPNPNPNVDPNAN), SEQ ID NO: 113 (NPDPNAAPNVDPNAN), SEQ ID NO: 114 (NPDPNANVDPNAN), SEQ ID NO: 115 (NPDPNANPAVDPNAN), and SEQ ID NO: 116 (NPDPNANPAVDPAAN).

FIGS. 4A-4D. Crystal structures of CIS43 Fab in complex with PfCSP peptides. FIG. 4A, Surface representation of CIS43 Fab with peptide 21 ($N_{101}$PDPNANPNVDPN$_{113}$, SEQ ID NO: 62) shown in sticks and 90° rotation with view down towards the combining sites. FIG. 4B, Sequence of CIS43 Fab following Kabat numbering and alignment with germline gene. The heavy chain variable region (SEQ ID NO: 11) and the light chain variable region (SEQ ID NO: 12) of CIS43 are shown. Residues that contact each peptide are shown as closed circle for main chain only, open star for side chains only and closed star for both main and side chains. FIG. 4C, Effect of mAbs on cleavage of PfCSP. Concentrations of mAbs (µg/ml) are indicated on top of the autoradiograph. P, pulse. Negative control: mAb15 (anti C terminus PfCSP mAb). Positive control: mAb5D5 (mouse anti-N terminus PfCSP mAb). Molecular mass is indicated in kilodaltons on the left side of the autoradiograph. FIG. 4D, Densitometry analysis of scanned autoradiograph. The density ratio of top to bottom PfCSP bands is shown for each chased sample. A ratio of 1 indicates the density of the top and bottom bands is equal. A representative of 3 independent experiments is shown.

FIG. 5A, Binding of varying concentrations of PfCSP mAbs isolated from plasmablasts to rPfCSP by ELISA. FIG. 5B, Effect of PfCSP mAbs on primary hepatocyte infection by PfSPZ in vitro. Infection rate was determined by enumeration of liver-stage parasites or exoerythrocytic forms (EEF) present at day 3.5 post infection and normalized by expressing as a fraction of untreated controls. Antibody concentrations are as shown, (bars represent mean EEF Fraction+/−one standard deviation). Representative of two independent experiments is shown. FIG. 5C, Binding specificity of PfCSP mAbs to rPfCSP, N-, Repeat, or C-terminal domains of PfCSP by ELISA. Controls: 2A10, a mouse anti-PfCSP repeat mAb, and 5D5, a mouse PfCSP N-terminus specific mAb. FIGS. 5D and 5E, Binding of mAbs to overlapping peptides spanning the repeat region (residues 97-276) of PfCSP with specified sequences numbered 20-61. Peptides 28-41, which consist only of NANP repeats, are represented by peptide 29.

FIGS. 5F and 5G, Binding of PfCSP mAbs to rPfCSP in the presence of varying concentrations of peptides.

FIG. 6A, CIS23, CIS34, CIS42, mAb10. FIG. 6B, Binding of mAb CIS43 to peptides 21 and 29. FIG. 6C, Binding of mAb10 to PfCSP mutant (PfCSP-P102A/D103N). Changes in the junctional epitope is highlighted. Upper panels show the output signal, dQ/dt, as a function of time. Lower panels show the integrated heats as a function of the antibody-site/rPfCSP molar ratio in the cell. The solid line represents the result from best non-linear least-squares fit of the data to a binding model that takes into account one or two sets of sites with different affinities. Dissociation constant (Kd), changes in Gibbs energy (ΔG) of binding, enthalpy (ΔH) and entropy (−TΔS) and stoichiometry (N) are shown.

FIGS. 7A-7D. Binding specificity and functional capacity of mAb CIS43 variant. FIG. 7A, Amino acid sequence alignment of mAb CIS43 (SEQ ID NO: 11) and mAb CIS43 variant (CIS43v, SEQ ID NO: 117) heavy chain variable regions. FIG. 7B, Binding of varying concentrations of mAb CIS43 (solid lines) and mAb CIS43 variant (dashed lines) to peptide 21 and to rPfCSP by ELISA. FIG. 7C, Binding free-energy changes (ΔΔG) of CIS43 variant Fab to peptide 21 were calculated for each individual mutation as well as for the four combined mutations. FIG. 7D, Effect of mAb CIS43 variant on primary human hepatocyte infection by PfSPZ in vitro. Infection rate was determined by enumerating EEFs at day 3.5 (as described in FIG. 2). Bars represent mean EEF+/−one standard deviation.

FIGS. 8A and 8B. Structures of CIS42 Fab in complex with PfCSP peptides. FIG. 8A, Surface representation of CIS42 Fab with peptide 21 in sticks representation and 90° rotation with view down towards the combining sites. The surface representation of CIS42 Fab with peptides 21, 20, 25, and 29 shown as sticks is provided, as is surface representation of CIS42 Fab with 2Fo-Fc electron density map shown at 1a around peptide 21, with peptide removed for visualization, with hydrophobic residues (glycine, alanine, valine, leucine, isoleucine, proline, phenylalanine, methionine, and tryptophan) shown in dark grey and electrostatics. FIG. 8B, Sequence of CIS42 Fab following Kabat numbering with residues that contact each peptide shown as open star for side chains only, closed circle for main chain only and closed star for both main and side chains. The sequence of CIS42 $V_H$ (SEQ ID NO: 9) and $V_L$ (SEQ ID NO: 10) is shown.

FIG. 9. PfCSP Immunoglobulin V-gene family usage.

FIGS. 10A-10D. Details of the interactions of CIS43 Fab with peptides 20, 21, 25, and 29.

FIGS. 11A-11D. Crystal structures of CIS43 Fab in complex with PfCSP peptides and structural explanation for peptide 21 scanning mutagenesis. FIG. 11A, Surface representation of CIS43 Fab with peptide 20, 21, 25, and 29 shown in sticks. FIG. 11B, Surface representation of CIS43 Fab with 2Fo-Fc map shown at 1a around peptide 21, with peptide removed for visualization, with hydrophobic residues (glycine, alanine, valine, leucine, isoleucine, proline, phenylalanine, methionine, and tryptophan) shown in orange and electrostatics. FIG. 11C, Ranking and structural explanation of peptide 21 alanine variants based on competition results from FIG. 3C. FIG. 11D, Structural visualization of the mutations. X indicates loss of hydrogen bonding when mutating the residue. Sequences shown in FIG. 11C are as follows: APDPNANPNVDPNAN (SEQ ID NO: 94), NPDPNANPNVDPNAN (SEQ ID NO: 62), NPDPNANPNVDANAN (SEQ ID NO: 105), NPDPNANPNVDPNAA (SEQ ID NO: 109), NPDPNANPNVDPAAN (SEQ ID NO: 106), NPDPNANPNVDPNSN (SEQ ID NO: 107), NPDPNANPNVAPNAN (SEQ ID NO: 104), NPDPAANPNVDPNAN (SEQ ID NO: 98), NPDPNPNPNVDPNAN (SEQ ID NO: 112), NPDANANPNVDPNAN (SEQ ID NO: 197), NADPNANPNVDPNAN (SEQ ID NO: 95), NPDPNSNPNVDPNAN (SEQ ID NO: 99), NPDPNGNPNVDPNAN (SEQ ID NO: 110), NPAPNANPNVDPNAN (SEQ ID NO: 96), NPDPNANPNADPNAN (SEQ ID NO: 103), NPDPNVNPNVDPNAN (SEQ ID NO: 111), NPDPNANPNVDPNRN (SEQ ID NO: 108), NPDPNPAVDPNAN (SEQ ID NO: 102), NPDPNAAPNVDPNAN (SEQ ID NO: 100), and NPDPNANANVDPNAN (SEQ ID NO: 101).

SEQUENCES

Figure 1A:
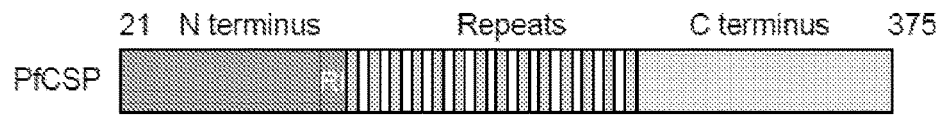

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "98294_Sequence.txt" (~72 kb), which is created on Aug. 2, 2019, and which is incorporated by reference herein. In the accompanying sequence listing:

SEQ ID NO: 1 is the amino acid sequence of the CIS04 $V_H$.
QVQLVQSGAEVKKPGASVKVSCKASGYTFTSYAIHWVRQAPGQRLEWMGWIKAGNGDTRYSQKFQGRVTITRDTSAT

TAYMELSSLRSEDTAVYYCGLLTVLTPDDAFDIWGQGTMVTVSS

-continued

SEQ ID NO: 2 is the amino acid sequence of the CIS04 $V_L$.
DIVMTQSPDSLAVSLGERATINCKSSQSVLYSSNNKNYLAWYQQKPGQPPKLLIYWASIRESGVPDRFSGSGSGTDF

TLTISSLQAEDVAVYYCHQYYSSPLTFGGGTKVEIK

SEQ ID NO: 3 is the amino acid sequence of the CIS06 $V_H$.
QVQLVQSGPEVKKPGTSVKVSCKASGFTFSSSAVQWVRQARGQRLEWIGWIVVGSGKTKYAQNFQQRVTITRDMSTS

TAYLELSTLRSEDTAVYYCAAVVNWNDESGFDPWGQGTLVTVSS

SEQ ID NO: 4 is the amino acid sequence of the CIS06 $V_L$.
DIQMTQSPSSLSAFVGDRVTITCRASQSIGTYLNWYQQKVGQAPKLLIYTASSLRSGVPSRFSGSGSGTDFTLTITS

LQPEDFATYYCQQSYSTYTFGQGTKLEIK

SEQ ID NO: 5 is the amino acid sequence of the CIS23 $V_H$.
EVQLVESGGGVVQPGRSLRLSCAASGFTFSSYGMYWVRQAPGKGLEWVALISHDGSNKFYADSVKGRFTISRDNSKN

TLYLQMNSLRAEDTAVYYCAKDLGYSSSWGYFDYWGQGTLVTVSS

SEQ ID NO: 6 is the amino acid sequence of the CIS23 $V_L$.
EIVLTQSPATLSLSPGERATLSCRASQSVSSYLAWYQQKPGQAPRLLIYDASNRATGIPARFSGSGSGTDFTLTISS

LEPEDFAVYYCQQRSNWYTFGQGTKLEIK

SEQ ID NO: 7 is the amino acid sequence of the CIS34 $V_H$.
QVQLVESGGGVVQPGRSLRLSCAASGFTFSSYGIHWVRQAPGKGLEWVAVIWYDGSKKYYGDSVKGRFTISRDNSKN

TLYLQMNSLRVEDTAVYYCARAVIAATGTRGYWFDPWGQGTLVTVSS

SEQ ID NO: 8 is the amino acid sequence of the CIS34 $V_L$.
DIIMTQSPVSLSASVGDRVTITCRASQSISSHLNWYQQKPGKAPKLLIYAASSLQSGVPSRFSGSGSGTDFTLTISS

LQPEDFATYSCQQTYRGFTFAPGTKVDIK

SEQ ID NO: 9 is the amino acid sequence of the CIS42 $V_H$.
QVQLVQSGSELKKPGASVKVSCKTSGYTFTTYAMNWVRQAPGQGLEWMGWINTNTGNPTYAPGFTGRFVFSFDTSVS

TAYLQISSLKAEDTAVYYCARVYSYGVPFDYWGQGTLVTVSS

SEQ ID NO: 10 is the amino acid sequence of the CIS42 $V_L$.
QSVLTQPASVSGSPGQSITISCTATSSNVGSFNLVSWYQHHPGKAPKLIIHEVSKRPSGASNRFSGSKSG

NTASLTISGLQAEDEADYYCCSYVGSDTWVFGGGTKLTVL

SEQ ID NO: 11 is the amino acid sequence of the CIS43 $V_H$.
QVQLVQSGAEVKKPGASVKVSCKASGYTFTSYAIHWVRQAPGQRLEWMGWIKAGNGNTRYSQKFQDRVTITROTSTT

TAYMELSSLRSEDTAVYYCALLTVLTPDDAFDIWGQGTMVTVSS

SEQ ID NO: 12 is the amino acid sequence of the CIS43 $V_L$.
DIVMTQSPDSLAVSLGERATINCKSSQSVLYSSNNKNYLAWYQQKPGQPPNLLIYWASTRQSGVPDRFSGSGSGTDF

TLTISSLQAEDVAVYYCHQYYSSPLTFGGGTKVEIK

SEQ ID NO: 13 is the amino acid sequence of an IgG1 heavy chain including the
CIS43 $V_H$.
QVQLVQSGAEVKKPGASVKVSCKASGYTFTSYAIHWVRQAPGQRLEWMGWIKAGNGNTRYSQKFQDRVTITRDTSTT

TAYMELSSLRSEDTAVYYCALLTVLTPDDAFDIWGQGTMVTVSSASTKGPSVFPLAPSSKSTSGGTAALGCLVKDYF

PEPVTVSWNSGALTSGVHTFPAVLQSSGLYSLSSVVTVPSSSLGTQTYICNVNHKPSNTKVDKKVEPKSCDKTHTCP

PCPAPELLGGPSVFLFPPKPKDTLMISRTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHYTQKSLSLSPGK

SEQ ID NO: 14 is the amino acid sequence of an IgG1 light chain including the
CIS43 $V_L$.
DIVMTQSPDSLAVSLGERATINCKSSQSVLYSSNNKNYLAWYQQKPGQPPNLLIYWASTRQSGVPDRFSGSGSGTDF

TLTISSLQAEDVAVYYCHQYYSSPLTFGGGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQGLSSPVTKSFNRGEC

SEQ ID NOs: 15-46 are the amino acid sequences of antibody CDRs.

SEQ ID NO: 47 is an exemplary nucleic acid sequence encoding the CIS04 $V_H$.
caggtgcagcttgtgcagtctggggctgaggtgaagaagcctggggcctcagtgaaggtttcctgcaaggcctctgg atacaccttcactagttatgctatacattgggtgcgccaggcccccggacaaaggcttgagtggatgggatggatca aggctggcaatggtgatacaagatattcacagaagttccagggcagagtcaccattaccagggacacatccgcgacc acagcctacatggagctgagcagcctgagatctgaagacacggctgtatattactgtggcctacttacggtgctaac tcctgatgatgcatttgatatctggggccaagggacaatggtcaccgtctcttca SEQ ID NO: 48 is an exemplary nucleic acid sequence encoding the CIS04 $V_L$.
gacatcgtgatgacccagtctccagactccctggctgtgtctctgggcgagagggccaccatcaactgcaagtccag ccagagtgttttatacagctccaacaataagaactacttagcttggtaccagcagaaaccaggacagcctcctaagc tgctcatttattgggcatctatccggaatccggggtccctgaccgattcagtggcagcgggtctgggacagatttc actctcaccatcagcagcctgcaggctgaagatgtggcagtttattactgtcaccagtattatagtagtcctctcac tttcggcggagggaccaaggtggaaatcaaa SEQ ID NO: 49 is an exemplary nucleic acid sequence encoding the CIS06 $V_H$.
caggtgcagctggtgcagtctgggcctgaggtgaagaagcctgggacctcagtgaaggtctcctgcaaggcttctgg attcacctttagtagctctgctgtgcagtgggtgcgacaggctcgtggacaacgccttgagtggataggatggatcg tcgttggcagtggtaagacaaagtacgcacagaacttccaacaaagagtcaccattaccagggacatgtccacaagt acagcctatctggagctgagcaccctgagatccgaggacacggccgtgtattactgtgcggcagttgtcaactggaa cgacgaaagcgggttcgaccctggggccagggaaccctggtcaccgtctcctca SEQ ID NO: 50 is an exemplary nucleic acid sequence encoding the CIS06 $V_L$.
gacatccagatgacccagtctccatcgtccctgtctgcatttgtgggagacagagtcaccatcacttgccgggcaag tcagagcattggcacctatttaaattggtatcagcagaaagtaggtcaagcccctaagctcctgatatatactgcat ccagtctgcgaagtggggtcccatcaaggttcagtggcagtggatctgggacagatttcactctcaccatcaccagt ctgcaacctgaagattttgcaacttactactgtcaacagagttacagtacctacacttttggccaggggaccaagct ggagatcaaa SEQ ID NO: 51 is an exemplary nucleic acid sequence encoding the CIS23 $V_H$.
gaggtgcagttggtggagtctggggggaggcgtggtccagcctggggaggtccctgagactctcctgtgcagcctctgg attcaccttcagtagctatggcatgtactgggtccgccaggctccaggcaaggggctggagtgggtggcacttatat cacatgatggaagtaataaattctatgcagactccgtgaagggccgattcaccatctccagagacaattccaagaac acgctgtatctgcaaatgaacagcctgagagctgaggacacggctgtgtattactgtgcgaaagacttgggttatag cagcagctgggggtactttgactactggggccagggaaccctggtcaccgtctcctca SEQ ID NO: 52 is an exemplary nucleic acid sequence encoding the CIS23 $V_L$.
gaaattgtgttgacacagtctccagccaccctgtctttgtctccaggggaaagagccaccctctcctgcagggccag tcagagtgttagcagctacttagcctggtaccaacagaaacctggccaggctcccaggctcctcatctatgatgcat ccaacagggccactggcatcccagccaggttcagtggcagtgggtctgggacagacttcactctcaccatcagcagc ctagagcctgaagattttgcagtttattactgtcagcagcgtagcaactggtacacttttggccaggggaccaagct ggagatcaaa SEQ ID NO: 53 is an exemplary nucleic acid sequence encoding the CIS34 $V_H$.
caggtgcagctggtggagtctgggggaggcgtggtccagcctggggaggtccctgagactctcctgtgcagcgtctgg attcaccttcagtagctatggcatacactgggtccgccaggctccaggcaaggggctggagtgggtggcagttatat ggtatgatggaagtaagaaatattatggagactctgtgaagggccgattcaccatctccagagacaattccaagaac acgctgtatctgcaaatgaacagcctgagagtcgaggacacggctgtgtattactgtgcgagggctgttatagcagc aactggtacgcgaggttactggttcgaccctggggccagggaaccctggtcaccgtctcctca SEQ ID NO: 54 is an exemplary nucleic acid sequence encoding the CIS34 $V_L$.
gacatcattatgacccagtctccagtctccctgtctgcatctgtaggagacagagtcaccatcacttgccgggcaag tcagagcattagcagccatttaaattggtatcagcagaaaccagggaaagcccctaagctcctgatctatgctgcat ccagtttgcaaagtggggtcccatcaaggttcagtggcagtggatctgggacagatttcactctcaccatcagcagt ctgcaacctgaagattttgcaacttactcctgtcaacagacttacaggggggttcactttcgcccctgggaccaaagt ggatatcaaa SEQ ID NO: 55 is an exemplary nucleic acid sequence encoding the CIS42 $V_H$.
caggtgcagctggtgcaatctgggtctgagttgaagaagcctggggcctcagtgaaggtttcctgcaagacttctgg atacaccttcactacctatgctatgaattgggtgcgacaggcccctggacaaaggccttgagtggatgggatggatca acaccaacactggaaacccaacgtacgccccgggcttcacagggcggtttgtcttctccttcgacacctctgtcagc acggcatatctgcagatcagcagcctgaaggctgaggacactgccgtttattactgtgcgagagtctacagctatgg ggtcccatttgactactggggccagggaaccctggtcaccgtctcctca SEQ ID NO: 56 is an exemplary nucleic acid sequence encoding the CIS42 $V_L$.
cagtctgtgctgactcagcctgcctccgtgtctgggtctcctggacagtcgatcaccatctcctgcactgcaaccag cagtaatgttgggagttttaaccttgtctcctggtaccaacatcacccaggcaaagcccccaaactcatcattcatg aggtcagtaagcggccctcaggggcttctaatcgcttctctggctccaagtctggcaacacggcctccctgacaatc tctgggctccaggctgaggacgaggctgattattactgctgctcatatgtaggcagtgacacttgggtgttcggcgg agggaccaagctgaccgtcctgggtcagcccaaggctgccccctcggtcactctgttcccgcc SEQ ID NO: 57 is an exemplary nucleic acid sequence encoding the CIS43 $V_H$.
caggtgcagcttgtgcagtctggggctgaggtgaagaagcctggggcctcagtgaaggtttcctgcaaggcctctgg atacaccttcactagttatgctatacattgggtgcgccaggcccccggacaaaggcttgagtggatggggtggatca aggctggcaatggtaatacaagatattcacagaagttccaggacagagtcaccattaccagggacacatccacgacc acagcctacatggagctgagcagcctgagatctgaagacacggctgtgtattactgtgccctacttacggtgctaac tcctgatgatgcttttgatatctggggccaggggaccatggtcaccgtctcttca SEQ ID NO: 58 is an exemplary nucleic acid sequence encoding the CIS43 $V_L$.
gacatcgtgatgacccagtctccagactccctggctgtgtctctgggcgagagggccaccatcaactgcaagtccag ccagagtgttctatacagctccaacaataagaactacttagcttggtaccagcagaaaccaggacagcctcctaacc tgctcatttactgggcatctacccggcaatccggggtccctgaccgattcagtggcagcgggtctgggacagatttc actctcaccatcagcagcctgcaggctgaagatgtggcagtttattactgtcaccagtattatagtagtcctctcac tttcggcggagggaccaaggtggaaatcaaa SEQ ID NO: 59 is an exemplary nucleic acid sequence encoding the amino acid
sequence of an IgG1 heavy chain including the CIS43 $V_H$.
caggtgcagcttgtgcagtctggggctgaggtgaagaagcctggggcctcagtgaaggtttcctgcaaggcctctgg atacaccttcactagttatgctatacattgggtgcgccaggcccccggacaaaggcttgagtggatggggtggatca aggctggcaatggtaatacaagatattcacagaagttccaggacagagtcaccattaccagggacacatccacgacc acagcctacatggagctgagcagcctgagatctgaagacacggctgtgtattactgtgccctacttacggtgctaac tcctgatgatgcttttgatatctggggccaggggaccatggtcaccgtctcttcagcgtcgaccaagggcccatcgg tcttccccctggcaccctcctccaagagcacctctgggggcacagcggccctgggctgcctggtcaaggactacttc cccgaacccgtgacggtgtcgtggaactcaggcgccctgaccagcggcgtgcacaccttcccggctgtcctacagtc ctcaggactctactccctcagcagcgtggtgaccgtgccctccagcagcttgggcacccagacctacatctgcaacg tgaatcacaagcccagcaacaccaaggtggacaagaaagttgagcccaaatcttgtgacaaaactcacacatgccca ccgtgcccagcacctgaactcctggggggaccgtcagtcttcctcttccccccaaaacccaaggacaccctcatgat ctcccggacccctgaggtcacatgcgtggtggtggacgtgagccacgaagaccctgaggtcaagttcaactggtacg tggacggcgtggaggtgcataatgccaagacaaagccgcgggaggagcagtacaacagcacgtaccgtgtggtcagc

```
gtcctcaccgtcctgcaccaggactggctgaatggcaaggagtacaagtgcaaggtctccaacaaagcccctcccagc ccccatcgagaaaaccatctccaaagccaaagggcagccccgagaaccacaggtgtacaccctgcccccatcccggg atgagctgaccaagaaccaggtcagcctgacctgcctggtcaaaggcttctatcccagcgacatcgccgtggagtgg gagagcaatgggcagccggagaacaactacaagaccacgcctcccgtgctggactccgacggctccttcttcctcta cagcaagctcaccgtggacaagagcaggtggcagcaggggaacgtcttctcatgctccgtgatgcatgaggctctgc acaaccactacacgcagaagagcctctccctgtctccgggtaaa
```

SEQ ID NO: 60 is an exemplary nucleic acid sequence encoding the amino acid sequence of an IgG1 light chain including the CIS43 $V_L$.
```
gacatcgtgatgacccagtctccagactccctggctgtgtctctgggcgagagggccaccatcaactgcaagtccag ccagagtgttctatacagctccaacaataagaactacttagcttggtaccagcagaaaccaggacagcctcctaacc tgctcatttactgggcatctacccggcaatccggggtccctgaccgattcagtggcagcgggtctgggacagatttc actctcaccatcagcagcctgcaggctgaagatgtggcagtttattactgtcaccagtattatagtagtcctctcac tttcggcggagggaccaaggtggaaatcaaacgtacggtggctgcaccatctgtcttcatcttcccgccatctgatg agcagttgaaatctggaactgcctctgttgtgtgcctgctgaataacttctaccccagagaagccaaagtgcagtgg aaggtggacaacgcccctgcagagcggaaacagccaggaaagcgtgacagagcaggattccaaggattccacatacag cctgagcagcacactgacactgtccaaggccgactacgagaagcacaaggtgtacgcctgcgaagtgacacaccagg gactgtcctcccctgtgacaaagagcttcaacagaggagaatgc
```

SEQ ID NOs: 61-79 are peptide sequences.
SEQ ID NO 61: PADGNPDPNANPNVD (peptide 20)

SEQ ID NO 62: NPDPNANPNVDPNAN (peptide 21)

SEQ ID NO 63: NANPNVDPNANPNVD (peptide 22)

SEQ ID NO 64: NVDPNANPNVDPNAN (peptide 23)

SEQ ID NO 65: NANPNVDPNANPNVD (peptide 24)

SEQ ID NO 66: NVDPNANPNVDPNAN (peptide 25)

SEQ ID NO 67: NANPNVDPNANPNAN (peptide 26)

SEQ ID NO 68: NVDPNANPNANPNAN (peptide 27)

SEQ ID NO 69: NANPNANPNANPNAN (peptide 29)

SEQ ID NO 70: NANPNANPNANPNVD (peptide 42)

SEQ ID NO 71: NANPNANPNVDPNAN (peptide 43)

SEQ ID NO 72: NANPNVDPNANPNAN (peptide 44)

SEQ ID NO 73: NVDPNANPNANPNAN (peptide 45)

SEQ ID NO 74: NANPNANPNANPNKN (peptide 61)

SEQ ID NO 75: NANPNANPNKNNQGN (peptide 62)

SEQ ID NO 76: NANPNKNNQGNGQGH (peptide 63)

SEQ ID NO 77: QEYQCYGSSSNTRVL (peptide 1)

SEQ ID NO 78: KLKQPADGNPDPNAN (peptide 19)

SEQ ID NO 79: NANPNANPNANPNANPNANPNANPNANPNANPNANP (NANP)$_9$

SEQ ID NO: 80 is an exemplary amino acid sequence for PfCSP (GenBank Acc. No. CAB38998.2, incorporated by reference herein)
MMRKLAILSVSSFLFVEALFQEYQCYGSSSNTRVLNELNYDNAGTNLYNELEMNYYGKQENWYSLKKNSRSLGENDD

GNNEDNEKLRKPKHKKLKQPADGNPDPNANPNVDPNANPNVDPNANPNVDPNANPNANPNANPNANPNANPNANPNA

NPNANPNANPNANPNANPNANPNANPNANPNANPNANPNANPNVDPNANPNANPNANPNANPNANPNANPNANPNAN

PNANPNANPNANPNANPNANPNANPNANPNANPNANPNANPNKNNQGNGQGHNMPNDPNRNVDENANANSAVKNNNN

-continued

EEPSDKHIKEYLNKIQNSLSTEWSPCSVTCGNGIQVRIKPGSANKPKDELDYANDIEKKICKMEKCSSVFNVVNSSI

GLIMVLSFLFLN

SEQ ID NO: 81 is the amino acid sequence of the mAb10 $V_H$
EVQLVESGGGVVQPGRSLRLSCEASGFTFSTYGMHWVRQAPGKGLEWVAIIWHDGSKKYHADSVRGRFTISRDNSKN

TLYLQMNSLRAEDTAVYFCARVGNYGGDWGAGFDYWGQGTLVTVSS

SEQ ID NO: 82 is the amino acid sequence of the mAb10 $V_L$

DIQMTQSPSFLSASVGDRVTIACRASQSISSWLAWYQQKPGKAPKLLIYHASSLESGVPSRFSGSASGTEFALTISS

LQPDDFATYYCQQYSSYWTFGQGTKVEIK

SEQ ID NO: 83 is an exemplary nucleic acid sequence encoding the mAb10 $V_H$
gaggtacagctggtcgaaagcggagggggggtcgtacaaccagggcgatcattgcggttaagctgtgaggcctcggg attcacattctcaacctatggaatgcactgggtgagacaggcaccaggaaaggggcttgagtgggtggctattattt ggcacgatggaagcaaaaagtatcacgctgacagcgtacgaggtcgctttacaatctcacgtgacaactccaaaaac acgctatatttgcaaatgaatagtctgcgtgcagaggatacagcagtctatttctgtgcacgagttgggaactacgg aggcgactggggtgccgggtttgattactgggggcaagggacacttgttactgttagctct SEQ ID NO: 84 is an exemplary nucleic acid sequence encoding the mAb10 $V_L$
gacatacaaatgacccaatcgccctcgttcctttcggcgagcgtcggtgatcgtgtcaccatagcctgccgggcaag tcaatcgatctcgagttggttggcgtggtatcagcagaaacctgggaaggctcccaaactattaatttatcacgcct catctttagaatctggggtgccctcacgatttttctggctcagcgagtggcactgagtttgccttaacaatcagctca ttacaacctgatgactttgcaacatactactgtcaacagtacagctcttactggacatttgggcaggggaccaaagt cgaaattaac SEQ ID NO: 85 is the amino acid sequence of an IgG1 heavy chain including the
mAb10 $V_H$.
EVQLVESGGGVVQPGRSLRLSCEASGFTFSTYGMHWVRQAPGKGLEWVAIIWHDGSKKYHADSVRGRFTISRDNSKN

TLYLQMNSLRAEDTAVYFCARVGNYGGDWGAGFDYWGQGTLVTVSSPSTKGPSVFPLAPSSKSTSGGTAALGCLVKD

YFPEPVTVSWNSGALTSGVHTFPAVLQSSGLYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVMHEALHNHYTQKSLSLSPGK

SEQ ID NO: 86 is an exemplary nucleic acid sequence of an IgG1 heavy chain
including the mAb10 $V_H$.
gaggtacagctggtcgaaagcggagggggggtcgtacaaccagggcgatcattgcggttaagctgtgaggcctcggg attcacattctcaacctatggaatgcactgggtgagacaggcaccaggaaaggggcttgagtgggtggctattattt ggcacgatggaagcaaaaagtatcacgctgacagcgtacgaggtcgctttacaatctcacgtgacaactccaaaaac acgctatatttgcaaatgaatagtctgcgtgcagaggatacagcagtctatttctgtgcacgagttgggaactacgg aggcgactggggtgccgggtttgattactgggggcaagggacacttgttactgttagctctccgtcgaccaagggcc catcggtcttccccctggcaccctcctccaagagcacctctgggggcacagcggccctgggctgcctggtcaaggac tacttccccgaaccggtgacggtgtcgtggaactcaggcgccctgaccagcggcgtgcacaccttcccggctgtcct acagtcctcaggactctactccctcagcagcgtggtgaccgtgccctccagcagcttgggcacccagacctacatct gcaacgtgaatcacaagcccagcaacaccaaggtggacaagaaagttgagcccaaatcttgtgacaaaactcacaca tgcccaccgtgcccagcacctgaactcctggggggaccgtcagtcttcctcttccccccaaaacccaaggacaccct catgatctcccggacccctgaggtcacatgcgtggtggtggacgtgagccacgaagaccctgaggtcaagttcaact ggtacgtggacggcgtggaggtgcataatgccaagacaaagccgcgggaggagcagtacaacagcacgtaccgtgtg gtcagcgtcctcaccgtcctgcaccaggactggctgaatggcaaggagtacaagtgcaaggtctccaacaaagccct cccagcccccatcgagaaaaccatctccaaagccaaagggcagccccgagaaccacaggtgtacaccctgcccccat

```
cccgggatgagctgaccaagaaccaggtcagcctgacctgcctggtcaaaggcttctatcccagcgacatcgccgtg gagtgggagagcaatgggcagccggagaacaactacaagaccacgcctcccgtgctggactccgacggctccttctt cctctacagcaagctcaccgtggacaagagcaggtggcagcaggggaacgtcttctcatgctccgtgatgcatgagg ctctgcacaaccactacacgcagaagagcctctcccctgtctccgggtaaa
```

SEQ ID NO: 87 is the amino acid sequence of an IgG1 light chain including the mAb10 V$_L$.
DIQMTQSPSFLSASVGDRVTIACRASQSISSWLAWYQQKPGKAPKLLIYHASSLESGVPSRFSGSASGTEFALTISS

LQPDDFATYYCQQYSSYWTFGQGTKVEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC

SEQ ID NOs: 88-93 are CDR amino acid sequences of mAb10.

SEQ ID NOs: 94-116 are peptide sequences.
SEQ ID NO: 94: APDPNANPNVDPNAN

SEQ ID NO: 95: NADPNANPNVDPNAN

SEQ ID NO: 96: NPAPNANPNVDPNAN

SEQ ID NO: 97: NPDANANPNVDPNAN

SEQ ID NO: 98: NPDPAANPNVDPNAN

SEQ ID NO: 99: NPDPNSNPNVDPNAN

SEQ ID NO: 100: NPDPNAAPNVDPNAN

SEQ ID NO: 101: NPDPNANANVDPNAN

SEQ ID NO: 102: NPDPNANPAVDPNAN

SEQ ID NO: 103: NPDPNANPNADPNAN

SEQ ID NO: 104: NPDPNANPNVAPNAN

SEQ ID NO: 105: NPDPNANPNVDANAN

SEQ ID NO: 106: NPDPNANPNVDPAAN

SEQ ID NO: 107: NPDPNANPNVDPNSN

SEQ ID NO: 108: NPDPNANPNVDPNRN

SEQ ID NO: 109: NPDPNANPNVDPNAA

SEQ ID NO: 110: NPDPNGNPNVDPNAN

SEQ ID NO: 111: NPDPNVNPNVDPNAN

SEQ ID NO: 112: NPDPNPNPNVDPNAN

SEQ ID NO: 113: NPDPNAAPNVDPNAN

SEQ ID NO: 114: NPDPNANANVDPNAN

SEQ ID NO: 115: NPDPNANPAVDPNAN

SEQ ID NO: 116: NPDPNANPAVDPAAN

SEQ ID NO: 117 is the amino acid sequence of the CIS43 V$_H$.
QVQLVQSGAEVKKPGASVKVSCKASGYTFTSYAIHWVRQAPGQRLEWMGWIKAGNGGGGYSGKFQDRVTITRDTSTT

TAYMELSSLRSEDTAVYYCALLTVLTPDDAFDIWGQGTMVTVSS

SEQ ID NO: 118 is the amino acid sequence of a signal peptide.
MGWSCIILFLVATATGVHS SEQ ID NO: 119 is the amino acid sequence of an IgG1 heavy chain including the CIS34 V$_H$.
QVQLVESGGGVVQPGRSLRLSCAASGFTFSSYGIHWVRQAPGKGLEWVAVIWYDGSKKYYGDSVKGRFTISRDNSKN

TLYLQMNSLRVEDTAVYYCARAVIAATGTRGYWFDPWGQGTLVTVSSASTKGPSVFPLAPSSKSTSGGTAALGCLVK

DYFPEPVTVSWNSGALTSGVHTFPAVLQSSGLYSLSSVVTVPSSSLGTQTYICNVNHKPSNTKVDKKVEPKSCDKTH

TCPPCPAPELLGGPSVFLFPPKPKDTLMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTLPPSRDELTKNQVSLTCLVKGFYPSDIA

VEWESNGQPENNYKTTPPVLDSDGSFFLYSKLTVDKSRWQQGNVFSCSVMHEALHNHYTQKSLSLSPGK

SEQ ID NO: 120 is the amino acid sequence of an IgG1 light chain including the
CIS34 $V_L$.
DIIMTQSPVSLSASVGDRVTITCRASQSISSHLNWYQQKPGKAPKLLIYAASSLQSGVPSRFSGSGSGTDFTLTISS

LQPEDFATYSCQQTYRGFTFAPGTKVDIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC

SEQ ID NO: 121 is an exemplary nucleic acid sequence encoding the amino acid
sequence of an IgG1 heavy chain including the CIS34 $V_H$.
caggtgcagctggtggagtctgggggaggcgtggtccagcctggggaggtccctgagactctcctgtgcagcgtctgg attcaccttcagtagctatggcatacactgggtccgccaggctccaggcaaggggctggagtgggtggcagtttatat ggtatgatggaagtaagaaatattatggagactctgtgaagggccgattcaccatctccagagacaattccaagaac acgctgtatctgcaaatgaacagcctgagagtcgaggacacggctgtgtattactgtgcgagggctgttatagcagc aactggtacgcgaggttactggttcgacccctggggccagggaaccctggtcaccgtctcctcagcgtcgaccaagg gcccatcggtcttccccctggcaccctcctccaagagcacctctgggggcacagcggccctgggctgcctggtcaag gactacttccccgaacccgtgacggtgtcgtggaactcaggcgccctgaccagcggcgtgcacaccttcccggctgt cctacagtcctcaggactctactccctcagcagcgtggtgaccgtgccctccagcagcttgggcacccagacctaca tctgcaacgtgaatcacaagcccagcaacaccaaggtggacaagaaagttgagcccaaatcttgtgacaaaactcac acatgcccaccgtgcccagcacctgaactcctggggggaccgtcagtcttcctcttccccccaaaacccaaggacac cctcatgatctcccggacccctgaggtcacatgcgtggtggtggacgtgagccacgaagaccctgaggtcaagttca actggtacgtggacggcgtggaggtgcataatgccaagacaaagccgcgggaggagcagtacaacagcacgtaccgt gtggtcagcgtcctcaccgtcctgcaccaggactggctgaatggcaaggagtacaagtgcaaggtctccaacaaagc cctcccagcccccatcgagaaaaccatctccaaagccaaagggcagccccgagaaccacaggtgtacaccctgcccc catcccgggatgagctgaccaagaaccaggtcagcctgacctgcctggtcaaaggcttctatcccagcgacatcgcc gtggagtgggagagcaatgggcagccggagaacaactacaagaccacgcctcccgtgctggactccgacggctcctt cttcctctacagcaagctcaccgtggacaagagcaggtggcagcaggggaacgtcttctcatgctccgtgatgcatg aggctctgcacaaccactacacgcagaagagcctctccctgtctccgggtaaa SEQ ID NO: 122 is an exemplary nucleic acid sequence encoding the amino acid
sequence of an IgG1 light chain including the CIS34 $V_L$.
gacatcattatgacccagtctccagtctccctgtctgcatctgtaggagacagagtcaccatcacttgccgggcaag tcagagcattagcagccatttaaattggtatcagcagaaaccagggaaagcccctaagctcctgatctatgctgcat ccagtttgcaaagtgggg̃tcccatcaaggttcagtggcagtggatctgggacagatttcactctcaccatcagcagt ctgcaacctgaagattttgcaacttactcctgtcaacagacttacaggggg̃ttcactttcgcccctgggaccaaagt ggatatcaaacgtacggtggctgcaccatctgtcttcatcttcccgccatctgatgagcagttgaaatctggaactg cctctgttgtgtgcctgctgaataacttctaccccagagaagccaaagtgcagtggaaggtggacaacgccctgcag agcggaaacagccaggaaagcgtgacagagcaggattccaaggattccacatacagcctgagcagcacactgacact gtccaaggccgactacgagaagcacaaggtgtacgcctgcgaagtgacacaccagggactgtcctcccctgtgacaa agagcttcaacagaggagaatgc SEQ ID NO: 123 is an exemplary nucleic acid sequence codon-optimized for
expression in human cells and encoding the mAb10 $V_H$
gaggtgcagctggtggaaagcggcggaggcgtggtgcagcctggcagatctctgagactgagctgcgaggccagcgg cttcaccttcagcacctacggcatgcactgggtgcgccagccccctggaaaaggcctggaatgggtggccatcatct ggcacgacggcagcaagaagtaccacgccgatagcgtgcgggg̃cagattcaccatcagccgggacaacagcaagaac -continued

```
accctgtacctgcagatgaacagcctgcgggccgaggataccgccgtgtacttctgtgccagagtgggcaactacgg cggcgattggggagccggctttgactattggggccagggcacactcgtgaccgtgtcctct
```

SEQ ID NO: 124 is an exemplary nucleic acid sequence codon-optimized for
expression in human cells and encoding the mAb10 V$_L$.

```
gacatccagatgacccagagccccagcttcctgagcgccagcgtgggcgacagagtgacaatcgcctgtagagccag ccagagcatcagcagctggctggcctggtatcagcagaagcctggcaaggcccccaaactgctgatctaccacgcca gcagcctggaaagcggcgtgcccagcagattttctggcagcgcctccggcaccgagttcgccctgacaatcagctcc ctgcagcccgacgacttcgccacctactactgccagcagtacagcagctactggaccttcggccagggcaccaaggt ggaaatcaag
```

DETAILED DESCRIPTION

Malaria is a mosquito-borne parasitic disease causing high morbidity and mortality, primarily in infants and young children in sub-Saharan Africa. Development of a highly effective vaccine or antibodies that can prevent and ultimately eliminate malaria is urgently needed. This disclosure provides a number of human monoclonal antibodies and antigen binding fragments directed against PfCSP. Data in the examples show that passive transfer of one of these antibodies, mAb CIS43, confers high-level, sterile protection in two different mouse malaria infection models including human liver-chimeric mice infected with PfSPZ by mosquito bites. mAb CIS43 preferentially binds with high affinity to a unique "junctional" epitope positioned immediately after the highly conserved Region I site at the junction of the N-terminus and the central repeat domain of PfCSP and prevents cleavage of PfCSP on PfSPZ. Moreover, stoichiometry and affinity of mAb CIS43 for PfCSP show two sequential multivalent binding events, recognizing a total of 6 sites per PfCSP with the junctional epitope being bound first with 7-fold higher affinity. Thus, the PfCSP-specific antibodies and antigen binding fragments provided herein, including CIS43, are effective for passive prevention of malaria for use in suitable subjects, such as travelers, military personnel, and subjects in elimination campaigns.

Features of interest for conferring protection by passive transfer of mAbs are potency and durability. As shown herein, biophysical and structural analyses showing sequential and multivalent, high affinity binding of mAb CIS43 to rPfCSP demonstrate a unique mechanism for neutralization that has not been observed for other antibodies. Moreover, binding of mAb CIS43 at a specific angle and rare conformation of the junctional epitope is unique. mAb CIS43 has multiple mechanisms for mediating protection in vivo. Multivalent binding of mAb CIS43 to PfCSP could inhibit sporozoite motility in the skin and by interfering with cleavage of PfCSP, this mAb would limit invasion of hepatocytes by sporozoites. Heretofore there are no human mAb that show sterile protection and also mediate their effect by binding to the junctional epitope on PfSPZ or effect cleavage of PfCSP. The findings presented herein showing that mAb CIS43 leads to a 10-100 fold reduction in liver burden compared to mAb10, an antibody against the NANP repeat region further provides clear evidence for greater potency.

I. SUMMARY OF TERMS

Unless otherwise noted, technical terms are used according to conventional usage. Definitions of many common terms in molecular biology may be found in Krebs et al. (eds.), Lewin's genes XII, published by Jones & Bartlett Learning, 2017. As used herein, the singular forms "a," "an," and "the," refer to both the singular as well as plural, unless the context clearly indicates otherwise. For example, the term "an antigen" includes singular or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Administration: The introduction of a composition into a subject by a chosen route. Administration can be local or systemic. For example, if the chosen route is intravenous, the composition is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Antibody and Antigen Binding Fragment: An immunoglobulin, antigen-binding fragment, or derivative thereof, that specifically binds and recognizes an analyte (antigen) such as PfCSP. The term "antibody" is used herein in the broadest sense and encompasses various antibody structures, including but not limited to monoclonal antibodies, polyclonal antibodies, multispecific antibodies (e.g., bispecific antibodies), and antigen binding fragments, so long as they exhibit the desired antigen-binding activity.

Non-limiting examples of antibodies include, for example, intact immunoglobulins and variants and fragments thereof that retain binding affinity for the antigen. Examples of antigen binding fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dübel (Eds.), *Antibody Engineering*, Vols. 1-2, 2$^{nd}$ ed., Springer-Verlag, 2010).

Antibodies also include genetically engineered forms such as chimeric antibodies (such as humanized murine antibodies) and heteroconjugate antibodies (such as bispecific antibodies).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Typically, a naturally occurring immunoglobulin has heavy (H) chains and light (L) chains interconnected by disulfide bonds Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain) In combination, the heavy and the light chain variable regions specifically bind the antigen.

References to "$V_H$" or "VH" refer to the variable region of an antibody heavy chain, including that of an antigen binding fragment, such as Fv, scFv, dsFv or Fab. References to "$V_L$" or "VL" refer to the variable domain of an antibody light chain, including that of an Fv, scFv, dsFv or Fab.

The $V_H$ and $V_L$ contain a "framework" region interrupted by three hypervariable regions, also called "complementarity-determining regions" or "CDRs" (see, e.g., Kabat et al., *Sequences of Proteins of Immunological Interest*, $5^{th}$ ed., NIH Publication No. 91-3242, Public Health Service, National Institutes of Health, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. (*Sequences of Proteins of Immunological Interest*, $5^{th}$ ed., NIH Publication No. 91-3242, Public Health Service, National Institutes of Health, U.S. Department of Health and Human Services, 1991; "Kabat" numbering scheme), Al-Lazikani et al., ("Standard conformations for the canonical structures of immunoglobulins," *J. Mol. Bio.*, 273(4):927-948, 1997; "Chothia" numbering scheme), and Lefranc et al. ("IMGT unique numbering for immunoglobulin and T cell receptor variable domains and Ig superfamily V-like domains," *Dev. Comp. Immunol.*, 27(1):55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the $V_H$ of the antibody in which it is found, whereas a $V_L$ CDR1 is the CDR1 from the $V_L$ of the antibody in which it is found. Light chain CDRs are sometimes referred to as LCDR1, LCDR2, and LCDR3. Heavy chain CDRs are sometimes referred to as HCDR1, HCDR2, and HCDR3.

In some embodiments, a disclosed antibody includes a heterologous constant domain. For example, the antibody includes a constant domain that is different from a native constant domain, such as a constant domain including one or more modifications (such as the "LS" mutations) to increase half-life.

A "monoclonal antibody" is an antibody obtained from a population of substantially homogeneous antibodies, that is, the individual antibodies comprising the population are identical and/or bind the same epitope, except for possible variant antibodies, for example, containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. In some examples monoclonal antibodies are isolated from a subject. Monoclonal antibodies can have conservative amino acid substitutions which have substantially no effect on antigen binding or other immunoglobulin functions. (See, for example, Greenfield (Ed.), *Antibodies: A Laboratory Manual*, $2^{nd}$ ed. New York: Cold Spring Harbor Laboratory Press, 2014.)

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. *Phage display: A Laboratory Manuel.* $1^{st}$ Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

Antibody or antigen binding fragment that neutralizes *P. falciparum*: An antibody or antigen binding fragment that specifically binds to a *P. falciparum* antigen (such as CSP) in such a way as to inhibit a biological function associated with *P. falciparum* that inhibits *P. falciparum* infection. The antibody can neutralize the activity of *P. falciparum* at various points during the lifecycle of the pathogen. For example, an antibody or antigen binding fragment that neutralizes *P. falciparum* may interfere with pathogen entry into the liver, attachment and invasion of a target cell by interfering with the interaction of the pathogen and one or more cell surface receptors. Alternately, an antibody may interfere with one or more post-attachment interactions of the pathogen with its receptors, for example, by interfering with pathogen internalization by receptor-mediated endocytosis.

In some embodiments, an antibody or antigen binding fragment that specifically binds to PfCSP and neutralizes *P. falciparum* inhibits sporozoite invasion of hepatocytes, for example, by at least 50% (such as at least 60%, at least 70%, at least 80%, at least 90%, or more) compared to a control antibody or antigen binding fragment. In some embodiments, an antibody or antigen binding fragment that specifically binds to PfCSP and neutralizes *P. falciparum* inhibits infection of a human subject by *P. falciparum*, for example, by at least 50% compared to a control antibody or antigen binding fragment.

Biological sample: A sample obtained from a subject. Biological samples include all clinical samples useful for detection of disease or infection (for example, *P. falciparum* infection) in subjects, including, but not limited to, cells, tissues, and bodily fluids, such as blood, derivatives and fractions of blood (such as serum), cerebrospinal fluid; as well as biopsied or surgically removed tissue, for example tissues that are unfixed, frozen, or fixed in formalin or paraffin. In a particular example, a biological sample is obtained from a subject having or suspected of having a *P. falciparum* infection.

Bispecific antibody: A recombinant molecule composed of two different antigen binding domains that consequently binds to two different antigenic epitopes. Bispecific antibodies include chemically or genetically linked molecules of two antigen-binding domains. The antigen binding domains can be linked using a linker. The antigen binding domains can be monoclonal antibodies, antigen-binding fragments (e.g., Fab, scFv), or combinations thereof. A bispecific antibody can include one or more constant domains, but does not necessarily include a constant domain.

Circumsporozoite protein (CSP): The circumsporozoite protein (CSP) is a major malaria parasite surface protein during the sporogonic cycle. CSP covers the surface of *P. falciparum* sporozoites, which are transmitted from the mosquito salivary gland to host hepatocytes. An exemplary PfCSP amino acid sequence is provided as SEQ ID NO: 80.

Conditions sufficient to form an immune complex: Conditions which allow an antibody or antigen binding fragment to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Greenfield (Ed.), *Antibodies: A Laboratory Manual*, 2$^{nd}$ ed. New York: Cold Spring Harbor Laboratory Press, 2014, for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intraorganismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The formation of an immune complex can be detected through conventional methods, for instance immunohistochemistry (IHC), immunoprecipitation (IP), flow cytometry, immunofluorescence microscopy, ELISA, immunoblotting (for example, Western blot), magnetic resonance imaging (MRI), computed tomography (CT) scans, radiography, and affinity chromatography Immunological binding properties of selected antibodies may be quantified using known methods.

Conjugate: A complex of two molecules linked together, for example, linked together by a covalent bond. In one embodiment, an antibody is linked to an effector molecule; for example, an antibody that specifically binds to CSP from *P. falciparum* covalently linked to an effector molecule. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules."

Conservative variants: "Conservative" amino acid substitutions are those substitutions that do not substantially affect or decrease a function of a protein, such as the ability of the protein to interact with a target protein. For example, a CSP-specific antibody can include up to 1, 2, 3, 4, 5, 6, 7, 8, 9, or up to 10 conservative substitutions compared to a reference antibody sequence and retain specific binding activity for CSP, and/or *P. falciparum* neutralization activity. The term conservative variation also includes the use of a substituted amino acid in place of an unsubstituted parent amino acid.

Individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the CSP specific antibody, such as the ability to specifically bind to CSP or neutralize *P. falciparum*. For instance, if an amino acid residue is essential for a function of the protein, even an otherwise conservative substitution may disrupt that activity. Thus, a conservative substitution does not alter the basic function of a protein of interest.

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antibody. Contacting can also include contacting a cell for example by placing an antibody in direct physical association with a cell.

Control: A reference standard. In some embodiments, the control is a negative control, such as sample obtained from a healthy patient not infected with *P. falciparum*. In other embodiments, the control is a positive control, such as a tissue sample obtained from a patient diagnosed with *P. falciparum* infection. In still other embodiments, the control is a historical control or standard reference value or range of values (such as a previously tested control sample, such as a group of *P. falciparum* patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, or at least about 500%.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). Methods for using detectable markers and guidance in the choice of detectable markers appropriate for various purposes are discussed for example in Green and Sambrook (*Molecular Cloning: A Laboratory Manual*, 4$^{th}$ ed., New York: Cold Spring Harbor Laboratory Press, 2012) and Ausubel et al. (Eds.) (*Current Protocols in Molecular Biology*, New York: John Wiley and Sons, including supplements, 2017).

Detecting: To identify the existence, presence, or fact of something.

Effective amount: A quantity of a specific substance sufficient to achieve a desired effect in a subject to whom the substance is administered. For instance, this can be the amount necessary to inhibit a *P. falciparum* infection, such as the amount necessary to inhibit or prevent *P. falciparum* sporozoites from invading the liver in the subject or to measurably alter outward symptoms of the *P. falciparum* infection.

In some embodiments, administration of an effective amount of a disclosed antibody or antigen binding fragment that binds to PfCSP can reduce or inhibit a *P. falciparum* infection (for example, as measured by infection of cells, or by number or percentage of subjects infected by the *P. falciparum*, or by an increase in the survival time of infected subjects, or reduction in symptoms associated with *P. falciparum* infection) by a desired amount, for example by at least 10%, at least 20%, at least 50%, at least 60%, at least 70%, at least 80%, at least 90%, at least 95%, at least 98%, or even at least 100% (elimination or prevention of detectable *P. falciparum* infection), as compared to a suitable control.

The effective amount of an antibody or antigen binding fragment that specifically binds PfCSP that is administered to a subject to inhibit *P. falciparum* infection will vary depending upon a number of factors associated with that subject, for example the overall health and/or weight of the subject. An effective amount can be determined by varying the dosage and measuring the resulting response, such as, for example, a reduction in pathogen titer. Effective amounts also can be determined through various in vitro, in vivo or in situ immunoassays.

An effective amount encompasses a fractional dose that contributes in combination with previous or subsequent administrations to attaining an effective response. For example, an effective amount of an agent can be administered in a single dose, or in several doses, for example daily, during a course of treatment lasting several days or weeks. However, the effective amount can depend on the subject being treated, the severity and type of the condition being treated, and the manner of administration. A unit dosage form of the agent can be packaged in an amount, or in multiples of the effective amount, for example, in a vial (e.g., with a pierceable lid) or syringe having sterile components.

Effector molecule: A molecule intended to have or produce a desired effect; for example, a desired effect on a cell to which the effector molecule is targeted. Effector molecules can include, for example, polypeptides and small molecules. In one non-limiting example, the effector molecule is a toxin. Some effector molecules may have or produce more than one desired effect.

Epitope: An antigenic determinant. These are particular chemical groups or peptide sequences on a molecule that are antigenic, i.e. that elicit a specific immune response. An antibody specifically binds a particular antigenic epitope on a polypeptide. In some examples a disclosed antibody specifically binds to an epitope on CSP from *P. falciparum*.

Expression: Transcription or translation of a nucleic acid sequence. For example, an encoding nucleic acid sequence (such as a gene) can be expressed when its DNA is transcribed into RNA or an RNA fragment, which in some examples is processed to become mRNA. An encoding nucleic acid sequence (such as a gene) may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcriptional terminators, a start codon (ATG) in front of a protein-encoding gene, splice signals for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Non-limiting examples of expression vectors include cosmids, plasmids (e.g., naked or contained in liposomes) and viruses (e.g., lentiviruses, retroviruses, adenoviruses, and adeno-associated viruses) that incorporate the recombinant polynucleotide.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Fc region: The constant region of an antibody excluding the first heavy chain constant domain Fc region generally refers to the last two heavy chain constant domains of IgA, IgD, and IgG, and the last three heavy chain constant domains of IgE and IgM. An Fc region may also include part or all of the flexible hinge N-terminal to these domains. For IgA and IgM, an Fc region may or may not include the tailpiece, and may or may not be bound by the J chain. For IgG, the Fc region is typically understood to include immunoglobulin domains C$\gamma$2 and C$\gamma$3 and optionally the lower part of the hinge between C$\gamma$1 and C$\gamma$2. Although the boundaries of the Fc region may vary, the human IgG heavy chain Fc region is usually defined to include residues following C226 or P230 to the Fc carboxyl-terminus, wherein the numbering is according to Kabat. For IgA, the Fc region includes immunoglobulin domains C$\alpha$2 and C$\alpha$3 and optionally the lower part of the hinge between C$\alpha$1 and C$\alpha$2.

IgA: A polypeptide belonging to the class of antibodies that are substantially encoded by a recognized immunoglobulin alpha gene. In humans, this class or isotype comprises IgA$_1$ and IgA$_2$. IgA antibodies can exist as monomers, polymers (referred to as pIgA) of predominantly dimeric form, and secretory IgA. The constant chain of wild-type IgA contains an 18-amino-acid extension at its C-terminus called the tail piece (tp). Polymeric IgA is secreted by plasma cells with a 15-kDa peptide called the J chain linking two monomers of IgA through the conserved cysteine residue in the tail piece.

IgG: A polypeptide belonging to the class or isotype of antibodies that are substantially encoded by a recognized immunoglobulin gamma gene. In humans, this class comprises IgG$_1$, IgG$_2$, IgG$_3$, and IgG$_4$.

Immune complex: The binding of antibody or antigen binding fragment (such as a scFv) to a soluble antigen forms an immune complex. The formation of an immune complex can be detected through conventional methods, for instance immunohistochemistry, immunoprecipitation, flow cytometry, immunofluorescence microscopy, ELISA, immunoblotting (for example, Western blot), magnetic resonance imaging, CT scans, radiography, and affinity chromatography.

Inhibiting a disease or condition: Reducing the full development of a disease or condition in a subject, for example, reducing the full development of a *P. falciparum* infection in a subject who is at risk of a *P. falciparum* infection. This includes neutralizing, antagonizing, prohibiting, preventing, restraining, slowing, disrupting, stopping, or reversing progression or severity of the disease or condition.

Inhibiting a disease or condition refers to a prophylactic intervention administered before the disease or condition has begun to develop (for example a treatment initiated in a subject at risk of *P. falciparum* infection, but not infected by *P. falciparum*) that reduces subsequent development of the disease or condition and/or ameliorates a sign or symptom of the disease or condition following development. The term "ameliorating," with reference to inhibiting a disease or condition refers to any observable beneficial effect of the prophylactic intervention intended to inhibit the disease or condition. The beneficial effect can be evidenced, for example, by a delayed onset of clinical symptoms of the disease or condition in a susceptible subject, a reduction in severity of some or all clinical symptoms of the disease or condition, a slower progression of the disease or condition, an improvement in the overall health or well-being of the subject, a reduction in infection, or by other parameters known in the art that are specific to the particular disease or condition.

In some embodiments, the disclosed CSP-specific antibodies and antigen binding fragments inhibit the invasion of *Plasmodium falciparum* sporozoites into human liver cells (hepatocytes). As mentioned above, the invasion of liver cells is a key event in the infection of a subject with the malaria parasite. Inhibition of the invasion of human liver cells can be measured by one or more of several standard assays (see, for example, Example 1). For example, the disclosed CSP-specific antibodies and antigen binding fragments can inhibit the invasion of *Plasmodium falciparum* sporozoites into human liver cells by at least 20%, at least 30%, at least 40%, or at least 50%, compared to a suitable control.

In some embodiments, the disclosed CSP-specific antibodies and antigen binding fragments inhibit the growth of *Plasmodium falciparum* in a subject, for example, the antibodies and antigen binding fragments inhibit the multiplication of *Plasmodium falciparum* in the subject, resulting in a reduction in pathogen load in the subject compared to a relevant control. For example, the disclosed CSP-specific antibodies and antigen binding fragments can inhibit the growth of *Plasmodium falciparum* in a subject by at least 20%, at least 30%, at least 40%, or at least 50%, compared to a suitable control.

Isolated: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. An isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

Kabat position: A position of a residue in an amino acid sequence that follows the numbering convention delineated by Kabat et al. (*Sequences of Proteins of Immunological Interest*, 5$^{th}$ Edition, Department of Health and Human Services, Public Health Service, National Institutes of Health, Bethesda, NIH Publication No. 91-3242, 1991).

Linker: A bi-functional molecule that can be used to link two molecules into one contiguous molecule, for example, to link an effector molecule to an antibody. Non-limiting examples of peptide linkers include glycine-serine linkers.

The terms "conjugating," "joining," "bonding," or "linking" can refer to making two molecules into one contiguous molecule; for example, linking two polypeptides into one contiguous polypeptide, or covalently attaching an effector molecule or detectable marker radionuclide or other molecule to a polypeptide, such as an scFv. The linkage can be either by chemical or recombinant means. "Chemical means" refers to a reaction between the antibody moiety and the effector molecule such that there is a covalent bond formed between the two molecules to form one molecule.

Malaria: Malaria is a parasitic infection of humans by the *Plasmodium* species *P. falciparum, P. vivax, P. ovale, P. malariae*, and *P. knowlesi*. Humans become infected following the bite of an infected mosquito, the host of the malarial parasite. Malaria rarely occurs in humans following a blood transfusion or subsequent to needle-sharing. Clinical manifestations of malarial infection which may occur include blackwater fever, cerebral malaria, respiratory failure, hepatic necrosis, occlusion of myocardial capillaries and death.

Infection begins when malaria sporozoites gain access to or are directly injected into the bloodstream of a host by a mosquito. After injection, they migrate to the liver and multiply in hepatocytes for ~one week. The sporozoites substantially expand in the liver and differentiate to merozoites which are released from the liver into the blood stream, where they infect erythrocytes. When the merozoite matures in the red blood cell, it is known as a trophozoite and, when fully developed, as a schizont. A schizont is the stage when nuclear division occurs to form individual merozoites which are released to invade other red cells. Malaria clinical symptoms appear during the blood-stage. After several schizogonic cycles, some parasites, instead of becoming schizonts through asexual reproduction, develop into large uninucleate parasites, known as gametocytes. These gametocytes are the sexual blood cell stage forms of the parasite.

Sexual development of the malaria parasites involves the female macrogametocyte and the male microgametocyte. If a mosquito feeds on the blood of an infected host, it can ingest gametocytes within the blood. Fertilization and sexual recombination of the parasite occurs in the mosquito's gut. The fertilized parasite, which is known as a zygote, then develops into an ookinete. The ookinete penetrates the midgut wall of the mosquito and develops into an oocyst, within which many small sporozoites form. When the oocyst ruptures, the sporozoites migrate to the salivary gland of the mosquito via the hemolymph. Once in the saliva of the mosquito, the parasite can be injected into a host, repeating the life cycle.

Nucleic acid (molecule or sequence): A deoxyribonucleotide or ribonucleotide polymer or combination thereof including without limitation, cDNA, mRNA, genomic DNA, and synthetic (such as chemically synthesized) DNA or RNA. The nucleic acid can be double stranded (ds) or single stranded (ss). Where single stranded, the nucleic acid can be the sense strand or the antisense strand. Nucleic acids can include natural nucleotides (such as A, T/U, C, and G), and can include analogs of natural nucleotides, such as labeled nucleotides.

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington: The Science and Practice of Pharmacy,* 22$^{nd}$ ed., London, UK: Pharmaceutical Press, 2013, describes compositions and formulations suitable for pharmaceutical delivery of the disclosed agents.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, added preservatives (such as non-natural preservatives), and pH buffering agents and the like, for example sodium acetate or sorbitan monolaurate. In particular examples, the pharmaceutically acceptable carrier is sterile and suitable for parenteral administration to a subject for example, by injection. In some embodiments, the active agent and pharmaceutically acceptable carrier are provided in a unit dosage form such as a pill or in a selected quantity in a vial. Unit dosage forms can include one dosage or multiple dosages (for example, in a vial from which metered dosages of the agents can selectively be dispensed).

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. A polypeptide includes both naturally occurring proteins, as well as those that are recombinantly or synthetically produced. A polypeptide has an amino terminal (N-terminal) end and a carboxy-terminal end. In some embodiments, the polypeptide is a disclosed antibody or a fragment thereof.

Purified: The term purified does not require absolute purity; rather, it is intended as a relative term. Thus, for example, a purified peptide preparation is one in which the peptide or protein (such as an antibody) is more enriched than the peptide or protein is in its natural environment within a cell. In one embodiment, a preparation is purified such that the protein or peptide represents at least 50% of the total peptide or protein content of the preparation.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sequence identity: The identity between two or more nucleic acid sequences, or two or more amino acid sequences, is expressed in terms of the identity between the sequences. Sequence identity can be measured in terms of percentage identity; the higher the percentage, the more identical the sequences. Homologs and variants of a $V_L$ or a $V_H$ of an antibody that specifically binds a target antigen are typically characterized by possession of at least about 75% sequence identity, for example at least about 80%, 85%, 90%, 91%, 92%, 93%, 94%, 95%, 96%, 97%, 98% or 99% sequence identity counted over the full-length alignment with the amino acid sequence of interest.

Methods of alignment of sequences for comparison are well known in the art. Various programs and alignment algorithms are described in: Smith and Waterman, *Adv. Appl. Math.* 2(4):482-489, 1981; Needleman and Wunsch, *J. Mol. Biol.* 48(3):443-453, 1970; Pearson and Lipman, *Proc. Natl. Acad. Sci. U.S.A.* 85(8):2444-2448, 1988; Higgins and Sharp, *Gene*, 73(1):237-244, 1988; Higgins and Sharp, *Bioinformatics*, 5(2):151-3, 1989; Corpet, *Nucleic Acids Res.* 16(22):10881-10890, 1988; Huang et al. *Bioinformatics*, 8(2):155-165, 1992; and Pearson, *Methods Mol. Biol.* 24:307-331, 1994. Altschul et al., *J. Mol. Biol.* 215(3):403-410, 1990, presents a detailed consideration of sequence alignment methods and homology calculations. The NCBI Basic Local Alignment Search Tool (BLAST) (Altschul et al., *J. Mol. Biol.* 215(3):403-410, 1990) is available from several sources, including the National Center for Biological Information and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Generally, once two sequences are aligned, the number of matches is determined by counting the number of positions where an identical nucleotide or amino acid residue is present in both sequences. The percent sequence identity between the two sequences is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100.

Specifically bind: When referring to an antibody or antigen binding fragment, refers to a binding reaction which determines the presence of a target protein in the presence of a heterogeneous population of proteins and other biologics. Thus, under designated conditions, an antibody binds preferentially to a particular target protein, peptide or polysaccharide (such as an antigen present on the surface of a pathogen, for example PfCSP) and does not bind in a significant amount to other proteins present in the sample or subject. Specific binding can be determined by standard methods. See Harlow & Lane, *Antibodies, A Laboratory Manual*, $2^{nd}$ ed., Cold Spring Harbor Publications, New York (2013), for a description of immunoassay formats and conditions that can be used to determine specific immunoreactivity.

With reference to an antibody-antigen complex, specific binding of the antigen and antibody has a $K_D$ of less than about $10^{-7}$ Molar, such as less than about $10^{-8}$ Molar, $10^{-9}$, or even less than about $10^{-10}$ Molar. $K_D$ refers to the dissociation constant for a given interaction, such as a polypeptide ligand interaction or an antibody antigen interaction. For example, for the bimolecular interaction of an antibody or antigen binding fragment and an antigen it is the concentration of the individual components of the bimolecular interaction divided by the concentration of the complex.

An antibody that specifically binds to an epitope on PfCSP is an antibody that binds substantially to PfCSP, including cells or tissue expressing PfCSP, substrate to which the PfCSP is attached, or PfCSP in a biological specimen. It is, of course, recognized that a certain degree of non-specific interaction may occur between an antibody or conjugate including an antibody (such as an antibody that specifically binds PfCSP or conjugate including such antibody) and a non-target (such as a cell that does not express PfCSP). Typically, specific binding results in a much stronger association between the antibody and protein or cells bearing the antigen than between the antibody and protein or cells lacking the antigen. Specific binding typically results in greater than 2-fold, such as greater than 5-fold, greater than 10-fold, or greater than 100-fold increase in amount of bound antibody (per unit time) to a protein including the epitope or cell or tissue expressing the target epitope as compared to a protein or cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein.

Subject: Living multi-cellular vertebrate organisms, a category that includes human and non-human mammals. In an example, a subject is a human. In an additional example, a subject is selected that is in need of inhibiting a P. falciparum infection. For example, the subject is uninfected and at risk of P. falciparum infection.

Transformed: A transformed cell is a cell into which a nucleic acid molecule has been introduced by molecular biology techniques. As used herein, the term transformed and the like (e.g., transformation, transfection, transduction, etc.) encompasses all techniques by which a nucleic acid molecule might be introduced into such a cell, including transduction with viral vectors, transformation with plasmid vectors, and introduction of DNA by electroporation, lipofection, and particle gun acceleration.

Vector: An entity containing a nucleic acid molecule (such as a DNA or RNA molecule) bearing a promoter(s) that is operationally linked to the coding sequence of a protein of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements. Viral vectors are recombinant nucleic acid vectors having at least some nucleic acid sequences derived from one or more viruses. In some embodiments, a viral vector comprises a nucleic acid molecule encoding a disclosed antibody or antigen binding fragment that specifically binds to PfCSP and neutralizes P. falciparum. In some embodiments, the viral vector can be an adeno-associated virus (AAV) vector.

II. DESCRIPTION OF SEVERAL EMBODIMENTS

A. Neutralizing Monoclonal Antibodies to CSP and Antigen Binding Fragments Thereof Isolated monoclonal antibodies and antigen binding fragments that specifically bind an epitope on PfCSP are provided. The antibodies and antigen binding fragments can be fully human. The antibodies and antigen binding fragments can neutralize P. falciparum, for example the disclosed antibodies can inhibit P. falciparum sporozoite infection of hepatocytes in vitro and P. falciparum sporozoite invasion of liver in vivo. Also disclosed herein are compositions including the antibodies and antigen binding fragments and a pharmaceutically acceptable carrier. Nucleic acids encoding the antibodies or antigen binding fragments, expression vectors (such as adeno-associated virus (AAV) viral vectors) including these nucleic acids are also provided. The antibodies, antigen binding fragments, nucleic acid molecules, host cells, and compositions can be used for research, diagnostic and prophylactic purposes. For example, the disclosed antibodies and antigen binding fragments can be used to diagnose a subject with a P. falciparum infection, or can be administered prophylactically to inhibit P. falciparum infection in a subject.

In several embodiments, the antibody or antigen binding fragment includes heavy and light chain variable regions including the HCDR1, HCDR2, and HCDR3, and LCDR1, LCDR2, and LCDR3, respectively, of one of the CIS04, CIS06, CIS23, CIS34, CIS42, CIS43, and mAb10 antibodies, and specifically binds to PfCSP and also neutralizes P. falciparum.

The discussion of monoclonal antibodies below refers to isolated monoclonal antibodies that include heavy and/or light chain variable domains (or antigen binding fragments thereof) including a CDR1, CDR2, and/or CDR3 with reference to the kabat numbering scheme (unless the context indicates otherwise). Various CDR numbering schemes (such as the Kabat, Chothia or IMGT numbering schemes) can be used to determine CDR positions. The amino acid sequence and the CDR positions of the heavy and light chain of the CIS04, CIS06, CIS23, CIS34, CIS42, CIS43, and mAb10 monoclonal antibodies according to the kabat numbering scheme are shown in Table 1.

TABLE 1

Kabat CDR sequences of CSP specific antibodies

| | CIS04 $V_H$ | | |
|---|---|---|---|
| $V_H$ | SEQ ID NO: 1 residues | A.A. Sequence | CDR SEQ ID NO |
| HCDR1 | 32-35 | YAIH | 15 |
| HCDR2 | 50-66 | WIKAGNGDTRYSQKFQG | 16 |
| HCDR3 | 98-110 | LLTVLTPDDAFDI | 17 |

| | CIS04 $V_L$ | | |
|---|---|---|---|
| $V_L$ | SEQ ID NO: 2 residues | A.A. Sequence | CDR SEQ ID NO |
| LCDR1 | 24-40 | KSSQSVLYSSNNKNYLA | 18 |
| LCDR2 | 56-62 | WASIRES | 19 |
| LCDR3 | 95-103 | HQYYSSPLT | 20 |

| | CIS06 $V_H$ | | |
|---|---|---|---|
| $V_H$ | SEQ ID NO: 3 residues | A.A. Sequence | CDR SEQ ID NO |
| HCDR1 | 32-35 | SAVQ | 21 |
| HCDR2 | 50-66 | WIVVGSGKTKYAQNFQQ | 22 |
| HCDR3 | 98-110 | AVVNWNDESGFDP | 23 |

TABLE 1-continued

Kabat CDR sequences of CSP specific antibodies

CIS06 V$_L$

| V$_L$ | SEQ ID NO: 4 residues | A.A. Sequence | CDR SEQ ID NO |
|---|---|---|---|
| LCDR1 | 24-34 | RASQSIGTYLN | 24 |
| LCDR2 | 50-56 | TASSLRS | 25 |
| LCDR3 | 89-96 | QQSYSTYT | 26 |

CIS23 V$_H$

| V$_H$ | SEQ ID NO: 5 residues | A.A. Sequence | CDR SEQ ID NO |
|---|---|---|---|
| HCDR1 | 32-35 | YGMY | 27 |
| HCDR2 | 50-66 | LISHDGSNKFYADSVKG | 28 |
| HCDR3 | 98-111 | KDLGYSSSWGYFDY | 29 |

CIS23 V$_L$

| V$_L$ | SEQ ID NO: 6 residues | A.A. Sequence | CDR SEQ ID NO |
|---|---|---|---|
| LCDR1 | 24-34 | RASQSVSSYLA | 30 |
| LCDR2 | 50-56 | DASNRAT | 31 |
| LCDR3 | 89-96 | QQRSNWYT | 32 |

CIS34 V$_H$

| V$_H$ | SEQ ID NO: 7 residues | A.A. Sequence | CDR SEQ ID NO |
|---|---|---|---|
| HCDR1 | 32-35 | YGIH | 33 |
| HCDR2 | 50-66 | VIWYDGSKKYYGDSVKG | 34 |
| HCDR3 | 98-113 | RAVIAATGTRGYWFDP | 35 |

CIS34 V$_L$

| V$_L$ | SEQ ID NO: 8 residues | A.A. Sequence | CDR SEQ ID NO |
|---|---|---|---|
| LCDR1 | 24-34 | RASQSISSHLN | 36 |
| LCDR2 | 50-56 | AASSLQS | 37 |
| LCDR3 | 89-96 | QQTYRGFT | 38 |

CIS42 V$_H$

| V$_H$ | SEQ ID NO: 9 residues | A.A. Sequence | CDR SEQ ID NO |
|---|---|---|---|
| HCDR1 | 32-35 | YAMN | 39 |
| HCDR2 | 50-66 | WINTNIGNPTYAPGFTG | 40 |
| HCDR3 | 98-108 | RVYSYGVPFDY | 41 |

TABLE 1-continued

Kabat CDR sequences of CSP specific antibodies

CIS42 V$_L$

| V$_L$ | SEQ ID NO: 10 residues | A.A. Sequence | CDR SEQ ID NO |
|---|---|---|---|
| LCDR1 | 23-36 | TATSSNVGSFNLVS | 42 |
| LCDR2 | 52-58 | EVSKRPS | 43 |
| LCDR3 | 91-100 | CSYVGSDTWV | 44 |

CIS43 V$_H$

| V$_H$ | SEQ ID NO: 11 residues | A.A. Sequence | CDR SEQ ID NO |
|---|---|---|---|
| HCDR1 | 32-35 | YAIH | 15 |
| HCDR2 | 50-66 | WIKAGNGNTRYSQKFQD | 45 |
| HCDR3 | 98-110 | LLTVLTPDDAFDI | 17 |

CIS43 V$_L$

| V$_L$ | SEQ ID NO: 12 residues | A.A. Sequence | CDR SEQ ID NO |
|---|---|---|---|
| LCDR1 | 24-40 | KSSQSVLYSSNNKNYLA | 18 |
| LCDR2 | 56-62 | WASTRQS | 46 |
| LCDR3 | 95-103 | HQYYSSPLT | 20 | mAb10 V$_H$

| V$_H$ | SEQ ID NO: 81 residues | A.A. Sequence | CDR SEQ ID NO |
|---|---|---|---|
| HCDR1 | 32-35 | YGMH | 88 |
| HCDR2 | 50-66 | IIWHDGSKKYHADSVRG | 89 |
| HCDR3 | 98-112 | RVGNYGGDWGAGFDY | 90 | mAb10 V$_L$

| V$_L$ | SEQ ID NO: 82 residues | A.A. Sequence | CDR SEQ ID NO |
|---|---|---|---|
| LCDR1 | 24-34 | RASQSISSWLA | 91 |
| LCDR2 | 50-56 | HASSLES | 92 |
| LCDR3 | 89-96 | QQYSSYWT | 93 |

CIS04

In some embodiments, the antibody or antigen binding fragment can be based on or derived from the CIS04 antibody, and specifically binds to PfCSP and neutralizes *P. falciparum*. For example, the antibody or antigen binding fragment comprises a V$_H$ and a V$_L$ comprising the HCDR1, the HCDR2, and the HCDR3, and the LCDR1, the LCDR2, and the LCDR3, respectively (for example, according to IMGT or kabat), of the CIS04 antibody, and specifically binds to PfCSP and neutralizes *P. falciparum*.

In some embodiments, the antibody or antigen binding fragment comprises a V$_H$ comprising the HCDR1, the HCDR2, and the HCDR3 of the CIS04 V$_H$ as set forth in Table 1, and specifically binds to PfCSP and neutralizes *P. falciparum*. In some embodiments, the antibody or antigen binding fragment comprises a $V_L$ comprising the LCDR1, the LCDR2, and the LCDR3 of the CIS04 $V_L$ as set forth in Table 1, and specifically binds to PfCSP and neutralizes *P. falciparum*. In some embodiments, the antibody or antigen binding fragment comprises a $V_H$ and a $V_L$ comprising the HCDR1, the HCDR2, the HCDR3, the LCDR1, the LCDR2, and the LCDR3 of the CIS04 $V_H$ and $V_L$ as set forth in Table 1, and specifically binds to PfCSP and neutralizes *P. falciparum*.

In some embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 32-35, 50-66, and 98-110, respectively, of SEQ ID NO: 1, and specifically binds to PfCSP and neutralizes *P. falciparum*. In some embodiments, the antibody or antigen binding fragment includes a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 24-40, 56-62, and 95-103, respectively, of SEQ ID NO: 2, and specifically binds to PfCSP and neutralizes *P. falciparum*. In additional embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 32-35, 50-66, and 98-110, respectively, of SEQ ID NO: 1, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 24-40, 56-62, and 95-103, respectively, of SEQ ID NO: 2, and specifically binds to PfCSP and neutralizes *P. falciparum*.

In some embodiments, the antibody or antigen binding fragment includes a $V_H$ comprising an amino acid sequence at least 90% (such as at least 95%, at least 96%, at least 97%, at least 98%, or at least 99%) identical to the amino acid sequence set forth as SEQ ID NO: 1, and specifically binds to PfCSP and neutralizes *P. falciparum*. In more embodiments, the antibody or antigen binding fragment includes a $V_L$ comprising an amino acid sequence at least 90% (such as at least 95%, at least 96%, at least 97%, at least 98%, or at least 99%) identical to the amino acid sequence set forth as SEQ ID NO: 2, and specifically binds to PfCSP and neutralizes *P. falciparum*. In additional embodiments, the antibody or antigen binding fragment includes a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 1 and 2, respectively, and specifically binds to PfCSP and neutralizes *P. falciparum*.

In some embodiments, the antibody or antigen binding fragment comprises a $V_H$ comprising a HCDR1, a HCDR2, and a HCDR3 as set forth as SEQ ID NOs: 15, 16, 17, respectively, and a $V_L$ comprising a LCDR1, a LCDR2, and a LCDR3 as set forth as SEQ ID NOs: 18, 19, 20, respectively, and specifically binds to PfCSP and neutralizes *P. falciparum*.

In some embodiments, the antibody or antigen binding fragment comprises a $V_H$ comprising a HCDR1, a HCDR2, and a HCDR3 as set forth as SEQ ID NOs: 15, 16, 17, respectively, a $V_L$ comprising a LCDR1, a LCDR2, and a LCDR3 as set forth as SEQ ID NOs: 18, 19, 20, respectively, wherein the $V_H$ comprises an amino acid sequence at least 90% identical to SEQ ID NO: 1, the $V_L$ comprises an amino acid sequence at least 90% identical to SEQ ID NO: 2, and the antibody or antigens binding fragment specifically binds to PfCSP and neutralizes *P. falciparum*.

In additional embodiments, the antibody or antigen binding fragment includes a $V_H$ comprising the amino acid sequence set forth as one of SEQ ID NO: 1, and specifically binds to PfCSP and neutralizes *P. falciparum*. In more embodiments, the antibody or antigen binding fragment includes a $V_L$ comprising the amino acid sequence set forth as SEQ ID NO: 2, and specifically binds to PfCSP and neutralizes *P. falciparum*. In some embodiments, the antibody or antigen binding fragment includes a $V_H$ and a $V_L$ comprising the amino acid sequences set forth as SEQ ID NOs: 1 and 2, respectively, and specifically binds to PfCSP and neutralizes *P. falciparum*.

CIS23

In some embodiments, the antibody or antigen binding fragment can be based on or derived from the CIS23 antibody, and specifically binds to PfCSP and neutralizes *P. falciparum*. For example, the antibody or antigen binding fragment comprises a $V_H$ and a $V_L$ comprising the HCDR1, the HCDR2, and the HCDR3, and the LCDR1, the LCDR2, and the LCDR3, respectively (for example, according to IMGT or kabat), of the CIS23 antibody, and specifically binds to PfCSP and neutralizes *P. falciparum*.

In some embodiments, the antibody or antigen binding fragment comprises a $V_H$ comprising the HCDR1, the HCDR2, and the HCDR3 of the CIS23 $V_H$ as set forth in Table 1, and specifically binds to PfCSP and neutralizes *P. falciparum*. In some embodiments, the antibody or antigen binding fragment comprises a $V_L$ comprising the LCDR1, the LCDR2, and the LCDR3 of the CIS23 $V_L$ as set forth in Table 1, and specifically binds to PfCSP and neutralizes *P. falciparum*. In some embodiments, the antibody or antigen binding fragment comprises a $V_H$ and a $V_L$ comprising the HCDR1, the HCDR2, the HCDR3, the LCDR1, the LCDR2, and the LCDR3 of the CIS23 $V_H$ and $V_L$ as set forth in Table 1, and specifically binds to PfCSP and neutralizes *P. falciparum*.

In some embodiments, the antibody or antigen binding fragment comprises a $V_H$ comprising a HCDR1, a HCDR2, and a HCDR3 comprising amino acid sequences at least 90% (such as at least 95%, at least 96%, at least 97%, at least 98%, or at least 99%) identical to amino acids 32-35, 50-66, and 98-111, respectively, of SEQ ID NO: 5, and specifically binds to PfCSP and neutralizes *P. falciparum*. In some embodiments, the antibody or antigen binding fragment comprises a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 24-34, 50-56, and 89-96, respectively, of SEQ ID NO: 6, and specifically binds to PfCSP and neutralizes *P. falciparum*. In additional embodiments, the antibody or antigen binding fragment comprises a $V_H$ comprising a HCDR1, a HCDR2, and a HCDR3 comprising amino acid sequences at least 90% (such as at least 95%, at least 96%, at least 97%, at least 98%, or at least 99%) identical to amino 32-35, 50-66, and 98-111, respectively, of SEQ ID NO: 5, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 24-34, 50-56, and 89-96, respectively, of SEQ ID NO: 6, and specifically binds to PfCSP and neutralizes *P. falciparum*.

In some embodiments, the antibody or antigen binding fragment comprises a $V_H$ comprising an amino acid sequence at least 90% (such as at least 95%, at least 96%, at least 97%, at least 98%, or at least 99%) identical to the amino acid sequence set forth as SEQ ID NO: 5, and specifically binds to PfCSP and neutralizes *P. falciparum*. In more embodiments, the antibody or antigen binding fragment comprises a $V_L$ comprising an amino acid sequence at least 90% (such as at least 95%, at least 96%, at least 97%, at least 98%, or at least 99%) identical to the amino acid sequence set forth as SEQ ID NO: 6, and specifically binds to PfCSP and neutralizes *P. falciparum*. In additional embodiments, the antibody or antigen binding fragment comprises a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 5 and 6, respectively, and specifically binds to PfCSP and neutralizes *P. falciparum*.

In some embodiments, the antibody or antigen binding fragment comprises a $V_H$ comprising a HCDR1, a HCDR2, and a HCDR3 as set forth as SEQ ID NOs: 27, 28, 29, respectively, and a $V_L$ comprising a LCDR1, a LCDR2, and a LCDR3 as set forth as SEQ ID NOs: 30, 31, 32, respectively, and specifically binds to PfCSP and neutralizes *P. falciparum*.

In some embodiments, the antibody or antigen binding fragment comprises a $V_H$ comprising a HCDR1, a HCDR2, and a HCDR3 as set forth as SEQ ID NOs: 27, 28, 29, respectively, a $V_L$ comprising a LCDR1, a LCDR2, and a LCDR3 as set forth as SEQ ID NOs: 30, 31, 32, respectively, wherein the $V_H$ comprises an amino acid sequence at least 90% identical to SEQ ID NO: 5, the $V_L$ comprises an amino acid sequence at least 90% identical to SEQ ID NO: 6, and the antibody or antigens binding fragment specifically binds to PfCSP and neutralizes *P. falciparum*.

In additional embodiments, the antibody or antigen binding fragment comprises a $V_H$ comprising the amino acid sequence set forth as one of SEQ ID NO: 5, and specifically binds to PfCSP and neutralizes *P. falciparum*. In more embodiments, the antibody or antigen binding fragment comprises a $V_L$ comprising the amino acid sequence set forth as SEQ ID NO: 6, and specifically binds to PfCSP and neutralizes *P. falciparum*. In some embodiments, the antibody or antigen binding fragment comprises a $V_H$ and a $V_L$ comprising the amino acid sequences set forth as SEQ ID NOs: 5 and 6, respectively, and specifically binds to PfCSP and neutralizes *P. falciparum*.

CIS34

In some embodiments, the antibody or antigen binding fragment can be based on or derived from the CIS34 antibody, and specifically binds to PfCSP and neutralizes *P. falciparum*. For example, the antibody or antigen binding fragment comprises a $V_H$ and a $V_L$ comprising the HCDR1, the HCDR2, and the HCDR3, and the LCDR1, the LCDR2, and the LCDR3, respectively (for example, according to IMGT or kabat), of the CIS34 antibody, and specifically binds to PfCSP and neutralizes *P. falciparum*.

In some embodiments, the antibody or antigen binding fragment comprises a $V_H$ comprising the HCDR1, the HCDR2, and the HCDR3 of the CIS34 $V_H$ as set forth in Table 1, and specifically binds to PfCSP and neutralizes *P. falciparum*. In some embodiments, the antibody or antigen binding fragment comprises a $V_L$ comprising the LCDR1, the LCDR2, and the LCDR3 of the CIS34 $V_L$ as set forth in Table 1, and specifically binds to PfCSP and neutralizes *P. falciparum*. In some embodiments, the antibody or antigen binding fragment comprises a $V_H$ and a $V_L$ comprising the HCDR1, the HCDR2, the HCDR3, the LCDR1, the LCDR2, and the LCDR3 of the CIS34 $V_H$ and $V_L$ as set forth in Table 1, and specifically binds to PfCSP and neutralizes *P. falciparum*.

In some embodiments, the antibody or antigen binding fragment comprises a $V_H$ comprising a HCDR1, a HCDR2, and a HCDR3 comprising amino acid sequences at least 90% (such as at least 95%, at least 96%, at least 97%, at least 98%, or at least 99%) identical to amino acids 32-35, 50-66, 98-113, respectively, of SEQ ID NO: 7, and specifically binds to PfCSP and neutralizes *P. falciparum*. In some embodiments, the antibody or antigen binding fragment comprises a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 24-34, 50-56, and 89-96, respectively, of SEQ ID NO: 8, and specifically binds to PfCSP and neutralizes *P. falciparum*. In additional embodiments, the antibody or antigen binding fragment comprises a $V_H$ comprising a HCDR1, a HCDR2, and a HCDR3 comprising amino acid sequences at least 90% (such as at least 95%, at least 96%, at least 97%, at least 98%, or at least 99%) identical to amino 32-35, 50-66, 98-113, respectively, of SEQ ID NO: 7, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 24-34, 50-56, and 89-96, respectively, of SEQ ID NO: 8, and specifically binds to PfCSP and neutralizes *P. falciparum*.

In some embodiments, the antibody or antigen binding fragment comprises a $V_H$ comprising an amino acid sequence at least 90% (such as at least 95%, at least 96%, at least 97%, at least 98%, or at least 99%) identical to the amino acid sequence set forth as SEQ ID NO: 7, and specifically binds to PfCSP and neutralizes *P. falciparum*. In more embodiments, the antibody or antigen binding fragment comprises a $V_L$ comprising an amino acid sequence at least 90% (such as at least 95%, at least 96%, at least 97%, at least 98%, or at least 99%) identical to the amino acid sequence set forth as SEQ ID NO: 8, and specifically binds to PfCSP and neutralizes *P. falciparum*. In additional embodiments, the antibody or antigen binding fragment comprises a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 7 and 8, respectively, and specifically binds to PfCSP and neutralizes *P. falciparum*.

In some embodiments, the antibody or antigen binding fragment comprises a $V_H$ comprising a HCDR1, a HCDR2, and a HCDR3 as set forth as SEQ ID NOs: 33, 34, 35, respectively, and a $V_L$ comprising a LCDR1, a LCDR2, and a LCDR3 as set forth as SEQ ID NOs: 36, 37, 38, respectively, and specifically binds to PfCSP and neutralizes *P. falciparum*.

In some embodiments, the antibody or antigen binding fragment comprises a $V_H$ comprising a HCDR1, a HCDR2, and a HCDR3 as set forth as SEQ ID NOs: 33, 34, 35, respectively, a $V_L$ comprising a LCDR1, a LCDR2, and a LCDR3 as set forth as SEQ ID NOs: 36, 37, 38, respectively, wherein the $V_H$ comprises an amino acid sequence at least 90% identical to SEQ ID NO: 7, the $V_L$ comprises an amino acid sequence at least 90% identical to SEQ ID NO: 8, and the antibody or antigens binding fragment specifically binds to PfCSP and neutralizes *P. falciparum*.

In additional embodiments, the antibody or antigen binding fragment comprises a $V_H$ comprising the amino acid sequence set forth as one of SEQ ID NO: 7, and specifically binds to PfCSP and neutralizes *P. falciparum*. In more embodiments, the antibody or antigen binding fragment comprises a $V_L$ comprising the amino acid sequence set forth as SEQ ID NO: 8, and specifically binds to PfCSP and neutralizes *P. falciparum*. In some embodiments, the antibody or antigen binding fragment comprises a VH and a $V_L$ comprising the amino acid sequences set forth as SEQ ID NOs: 7 and 8, respectively, and specifically binds to PfCSP and neutralizes *P. falciparum*.

CIS42

In some embodiments, the antibody or antigen binding fragment can be based on or derived from the CIS42 antibody, and specifically binds to PfCSP and neutralizes *P. falciparum*. For example, the antibody or antigen binding fragment comprises a $V_H$ and a $V_L$ comprising the HCDR1, the HCDR2, and the HCDR3, and the LCDR1, the LCDR2, and the LCDR3, respectively (for example, according to IMGT or kabat), of the CIS42 antibody, and specifically binds to PfCSP and neutralizes *P. falciparum*.

In some embodiments, the antibody or antigen binding fragment comprises a $V_H$ comprising the HCDR1, the HCDR2, and the HCDR3 of the CIS42 $V_H$ as set forth in Table 1, and specifically binds to PfCSP and neutralizes *P. falciparum*. In some embodiments, the antibody or antigen binding fragment comprises a $V_L$ comprising the LCDR1, the LCDR2, and the LCDR3 of the CIS42 $V_L$ as set forth in Table 1, and specifically binds to PfCSP and neutralizes *P. falciparum*. In some embodiments, the antibody or antigen binding fragment comprises a $V_H$ and a $V_L$ comprising the HCDR1, the HCDR2, the HCDR3, the LCDR1, the LCDR2, and the LCDR3 of the CIS42 $V_H$ and $V_L$ as set forth in Table 1, and specifically binds to PfCSP and neutralizes *P. falciparum*.

In some embodiments, the antibody or antigen binding fragment comprises a VH comprising a HCDR1, a HCDR2, and a HCDR3 comprising amino acid sequences at least 90% (such as at least 95%, at least 96%, at least 97%, at least 98%, or at least 99%) identical to amino acids 32-35, 50-66, and 98-108, respectively, of SEQ ID NO: 9, and specifically binds to PfCSP and neutralizes *P. falciparum*. In some embodiments, the antibody or antigen binding fragment comprises a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 23-36, 52-58, and 91-100, respectively, of SEQ ID NO: 10, and specifically binds to PfCSP and neutralizes *P. falciparum*. In additional embodiments, the antibody or antigen binding fragment comprises a $V_H$ comprising a HCDR1, a HCDR2, and a HCDR3 comprising amino acid sequences at least 90% (such as at least 95%, at least 96%, at least 97%, at least 98%, or at least 99%) identical to amino 32-35, 50-66, and 98-108, respectively, of SEQ ID NO: 9, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 23-36, 52-58, and 91-100, respectively, of SEQ ID NO: 10, and specifically binds to PfCSP and neutralizes *P. falciparum*.

In some embodiments, the antibody or antigen binding fragment comprises a $V_H$ comprising an amino acid sequence at least 90% (such as at least 95%, at least 96%, at least 97%, at least 98%, or at least 99%) identical to the amino acid sequence set forth as SEQ ID NO: 9, and specifically binds to PfCSP and neutralizes *P. falciparum*. In more embodiments, the antibody or antigen binding fragment comprises a $V_L$ comprising an amino acid sequence at least 90% (such as at least 95%, at least 96%, at least 97%, at least 98%, or at least 99%) identical to the amino acid sequence set forth as SEQ ID NO: 10, and specifically binds to PfCSP and neutralizes *P. falciparum*. In additional embodiments, the antibody or antigen binding fragment comprises a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 9 and 10, respectively, and specifically binds to PfCSP and neutralizes *P. falciparum*.

In some embodiments, the antibody or antigen binding fragment comprises a $V_H$ comprising a HCDR1, a HCDR2, and a HCDR3 as set forth as SEQ ID NOs: 39, 40, 41, respectively, and a $V_L$ comprising a LCDR1, a LCDR2, and a LCDR3 as set forth as SEQ ID NOs: 42, 43, 44, respectively, and specifically binds to PfCSP and neutralizes *P. falciparum*.

In some embodiments, the antibody or antigen binding fragment comprises a $V_H$ comprising a HCDR1, a HCDR2, and a HCDR3 as set forth as SEQ ID NOs: 39, 40, 41, respectively, a $V_L$ comprising a LCDR1, a LCDR2, and a LCDR3 as set forth as SEQ ID NOs: 42, 43, 44, respectively, wherein the $V_H$ comprises an amino acid sequence at least 90% identical to SEQ ID NO: 9, the $V_L$ comprises an amino acid sequence at least 90% identical to SEQ ID NO: 10, and the antibody or antigens binding fragment specifically binds to PfCSP and neutralizes *P. falciparum*.

In additional embodiments, the antibody or antigen binding fragment comprises a $V_H$ comprising the amino acid sequence set forth as one of SEQ ID NO: 9, and specifically binds to PfCSP and neutralizes *P. falciparum*. In more embodiments, the antibody or antigen binding fragment comprises a $V_L$ comprising the amino acid sequence set forth as SEQ ID NO: 10, and specifically binds to PfCSP and neutralizes *P. falciparum*. In some embodiments, the antibody or antigen binding fragment comprises a $V_H$ and a $V_L$ comprising the amino acid sequences set forth as SEQ ID NOs: 9 and 10, respectively, and specifically binds to PfCSP and neutralizes *P. falciparum*.

CIS43

In some embodiments, the antibody or antigen binding fragment can be based on or derived from the CIS43 antibody, and specifically binds to PfCSP and neutralizes *P. falciparum*. For example, the antibody or antigen binding fragment comprises a $V_H$ and a $V_L$ comprising the HCDR1, the HCDR2, and the HCDR3, and the LCDR1, the LCDR2, and the LCDR3, respectively (for example, according to IMGT or kabat), of the CIS43 antibody, and specifically binds to PfCSP and neutralizes *P. falciparum*.

In some embodiments, the antibody or antigen binding fragment comprises a $V_H$ comprising the HCDR1, the HCDR2, and the HCDR3 of the CIS43 $V_H$ as set forth in Table 1, and specifically binds to PfCSP and neutralizes *P. falciparum*. In some embodiments, the antibody or antigen binding fragment comprises a $V_L$ comprising the LCDR1, the LCDR2, and the LCDR3 of the CIS43 $V_L$ as set forth in Table 1, and specifically binds to PfCSP and neutralizes *P. falciparum*. In some embodiments, the antibody or antigen binding fragment comprises a $V_H$ and a $V_L$ comprising the HCDR1, the HCDR2, the HCDR3, the LCDR1, the LCDR2, and the LCDR3 of the CIS43 $V_H$ and $V_L$ as set forth in Table 1, and specifically binds to PfCSP and neutralizes *P. falciparum*.

In some embodiments, the antibody or antigen binding fragment comprises a VH comprising a HCDR1, a HCDR2, and a HCDR3 comprising amino acid sequences at least 90% (such as at least 95%, at least 96%, at least 97%, at least 98%, or at least 99%) identical to amino acids 32-35, 50-66, and 98-110, respectively, of SEQ ID NO: 11, and specifically binds to PfCSP and neutralizes P. falciparum. In some embodiments, the antibody or antigen binding fragment comprises a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 24-40, 56-62, and 95-103, respectively, of SEQ ID NO: 12, and specifically binds to PfCSP and neutralizes P. falciparum. In additional embodiments, the antibody or antigen binding fragment comprises a VH comprising a HCDR1, a HCDR2, and a HCDR3 comprising amino acid sequences at least 90% (such as at least 95%, at least 96%, at least 97%, at least 98%, or at least 99%) identical to amino 32-35, 50-66, and 98-110, respectively, of SEQ ID NO: 11, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 24-40, 56-62, and 95-103, respectively, of SEQ ID NO: 12, and specifically binds to PfCSP and neutralizes P. falciparum.

In some embodiments, the antibody or antigen binding fragment comprises a VH comprising an amino acid sequence at least 90% (such as at least 95%, at least 96%, at least 97%, at least 98%, or at least 99%) identical to the amino acid sequence set forth as SEQ ID NO: 11, and specifically binds to PfCSP and neutralizes P. falciparum. In more embodiments, the antibody or antigen binding fragment comprises a $V_L$ comprising an amino acid sequence at least 90% (such as at least 95%, at least 96%, at least 97%, at least 98%, or at least 99%) identical to the amino acid sequence set forth as SEQ ID NO: 12, and specifically binds to PfCSP and neutralizes P. falciparum. In additional embodiments, the antibody or antigen binding fragment comprises a VH and a $V_L$ independently comprising amino acid sequences at least 90% (such as at least 95%, at least 96%, at least 97%, at least 98%, or at least 99%) identical to the amino acid sequences set forth as SEQ ID NOs: 11 and 12, respectively, and specifically binds to PfCSP and neutralizes P. falciparum.

In some embodiments, the antibody or antigen binding fragment comprises a VH comprising a HCDR1, a HCDR2, and a HCDR3 as set forth as SEQ ID NOs: 15, 45, 17, respectively, and a $V_L$ comprising a LCDR1, a LCDR2, and a LCDR3 as set forth as SEQ ID NOs: 18, 46, 20, respectively, and specifically binds to PfCSP and neutralizes P. falciparum.

In some embodiments, the antibody or antigen binding fragment comprises a VH comprising a HCDR1, a HCDR2, and a HCDR3 as set forth as SEQ ID NOs: 15, 45, 17, respectively, a $V_L$ comprising a LCDR1, a LCDR2, and a LCDR3 as set forth as SEQ ID NOs: 18, 46, 20, respectively, wherein the VH comprises an amino acid sequence at least 90% identical to SEQ ID NO: 11, the $V_L$ comprises an amino acid sequence at least 90% identical to SEQ ID NO: 12, and the antibody or antigens binding fragment specifically binds to PfCSP and neutralizes P. falciparum.

In additional embodiments, the antibody or antigen binding fragment comprises a VH comprising the amino acid sequence set forth as one of SEQ ID NO: 11, and specifically binds to PfCSP and neutralizes P. falciparum. In more embodiments, the antibody or antigen binding fragment comprises a $V_L$ comprising the amino acid sequence set forth as SEQ ID NO: 12, and specifically binds to PfCSP and neutralizes P. falciparum. In some embodiments, the antibody or antigen binding fragment comprises a $V_H$ and a $V_L$ comprising the amino acid sequences set forth as SEQ ID NOs: 11 and 12, respectively, and specifically binds to PfCSP and neutralizes P. falciparum.

mAb10

In some embodiments, the antibody or antigen binding fragment can be based on or derived from the mAb10 antibody, and specifically binds to PfCSP and neutralizes P. falciparum. For example, the antibody or antigen binding fragment comprises a $V_H$ and a $V_L$ comprising the HCDR1, the HCDR2, and the HCDR3, and the LCDR1, the LCDR2, and the LCDR3, respectively (for example, according to IMGT or kabat), of the mAb10 antibody, and specifically binds to PfCSP and neutralizes P. falciparum.

In some embodiments, the antibody or antigen binding fragment comprises a $V_H$ comprising the HCDR1, the HCDR2, and the HCDR3 of the mAb10 $V_H$ as set forth in Table 1, and specifically binds to PfCSP and neutralizes P. falciparum. In some embodiments, the antibody or antigen binding fragment comprises a $V_L$ comprising the LCDR1, the LCDR2, and the LCDR3 of the mAb10 $V_L$ as set forth in Table 1, and specifically binds to PfCSP and neutralizes P. falciparum. In some embodiments, the antibody or antigen binding fragment comprises a $V_H$ and a $V_L$ comprising the HCDR1, the HCDR2, the HCDR3, the LCDR1, the LCDR2, and the LCDR3 of the mAb10 $V_H$ and $V_L$ as set forth in Table 1, and specifically binds to PfCSP and neutralizes P. falciparum.

In some embodiments, the antibody or antigen binding fragment comprises a $V_H$ comprising a HCDR1, a HCDR2, and a HCDR3 comprising amino acid sequences at least 90% (such as at least 95%, at least 96%, at least 97%, at least 98%, or at least 99%) identical to amino acids 32-35, 50-66, and 98-112, respectively, of SEQ ID NO: 81, and specifically binds to PfCSP and neutralizes P. falciparum. In some embodiments, the antibody or antigen binding fragment comprises a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 24-40, 56-56, and 89-96, respectively, of SEQ ID NO: 82, and specifically binds to PfCSP and neutralizes P. falciparum. In additional embodiments, the antibody or antigen binding fragment comprises a $V_H$ comprising a HCDR1, a HCDR2, and a HCDR3 comprising amino acid sequences at least 90% (such as at least 95%, at least 96%, at least 97%, at least 98%, or at least 99%) identical to amino 32-35, 50-66, and 98-112, respectively, of SEQ ID NO: 11, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 24-40, 56-56, and 89-96, respectively, of SEQ ID NO: 82, and specifically binds to PfCSP and neutralizes P. falciparum.

In some embodiments, the antibody or antigen binding fragment comprises a $V_H$ comprising an amino acid sequence at least 90% (such as at least 95%, at least 96%, at least 97%, at least 98%, or at least 99%) identical to the amino acid sequence set forth as SEQ ID NO: 81, and specifically binds to PfCSP and neutralizes P. falciparum. In more embodiments, the antibody or antigen binding fragment comprises a $V_L$ comprising an amino acid sequence at least 90% (such as at least 95%, at least 96%, at least 97%, at least 98%, or at least 99%) identical to the amino acid sequence set forth as SEQ ID NO: 82, and specifically binds to PfCSP and neutralizes P. falciparum. In additional embodiments, the antibody or antigen binding fragment comprises a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 81 and 82, respectively, and specifically binds to PfCSP and neutralizes *P. falciparum*.

In some embodiments, the antibody or antigen binding fragment comprises a $V_H$ comprising a HCDR1, a HCDR2, and a HCDR3 as set forth as SEQ ID NOs: 88, 89, 90, respectively, and a $V_L$ comprising a LCDR1, a LCDR2, and a LCDR3 as set forth as SEQ ID NOs: 91, 92, 93, respectively, and specifically binds to PfCSP and neutralizes *P. falciparum*.

In some embodiments, the antibody or antigen binding fragment comprises a $V_H$ comprising a HCDR1, a HCDR2, and a HCDR3 as set forth as SEQ ID NOs: 88, 89, 90, respectively, a $V_L$ comprising a LCDR1, a LCDR2, and a LCDR3 as set forth as SEQ ID NOs: 91, 92, 93, respectively, wherein the $V_H$ comprises an amino acid sequence at least 90% identical to SEQ ID NO: 81, the $V_L$ comprises an amino acid sequence at least 90% identical to SEQ ID NO: 82, and the antibody or antigens binding fragment specifically binds to PfCSP and neutralizes *P. falciparum*.

In additional embodiments, the antibody or antigen binding fragment comprises a $V_H$ comprising the amino acid sequence set forth as one of SEQ ID NO: 81, and specifically binds to PfCSP and neutralizes *P. falciparum*. In more embodiments, the antibody or antigen binding fragment comprises a $V_L$ comprising the amino acid sequence set forth as SEQ ID NO: 82, and specifically binds to PfCSP and neutralizes *P. falciparum*. In some embodiments, the antibody or antigen binding fragment comprises a $V_H$ and a $V_L$ comprising the amino acid sequences set forth as SEQ ID NOs: 81 and 82, respectively, and specifically binds to PfCSP and neutralizes *P. falciparum*.

Additional Antibodies that Bind to the CIS43 Epitope on PfCSP

In additional embodiments, isolated monoclonal antibodies and antigen binding fragments thereof that specifically bind to the CIS43 epitope on PfCSP are provided. Epitope mapping and structural studies provided herein allow for detailed analysis of the binding of CIS43 to PfCSP, definition of the CIS43 epitope on PfCSP, and an understanding of the structure required of an antibody to bind to the CIS43 epitope on PfCSP and provide the unexpectedly superior *P. falciparum* neutralization of CIS43.

As discussed in the Examples, the CIS43 antibody specifically binds to an epitope on PfCSP covering the junction between the N-terminal region and the repeat region of PfCSP, and binding to this particular epitope correlated with the unexpectedly superior neutralization capacity of CIS43. The corresponding epitope sequence is provided herein as peptide 21 (NPDPNANPNVDPNAN, SEQ ID NO: 62). CIS43 binds to this epitope with an apparent $K_D$ of less than 0.001 nM (determined by biolayer inferometry).

Accordingly, in some embodiments, an antibody or antigen binding fragment is provided that specifically binds to an epitope on PfCSP consisting of the amino acid sequence set forth as NPDPNANPNVDPNAN (SEQ ID NO: 62), covers the junction between the N-terminal region and the repeat region of PfCSP. In several embodiments, the antibody or antigen binding fragment specifically binds to the epitope on PfCSP consisting of the amino acid sequence set forth as NPDPNANPNVDPNAN (SEQ ID NO: 62) with a $K_D$ of less than 0.001 nM as determined by biolayer inferometry.

Antibodies that bind to the CIS43 epitope can be identified based on their ability to cross-compete (for example, to competitively inhibit the binding of, in a statistically significant manner) with the CIS43 antibody provided herein in PfCSP binding assays and/or Peptide 21 binding assay (such as those described in the Examples). An antibody "competes" for binding when the competing antibody inhibits PfCSP or Peptide 21 binding of the CIS43 antibody by more than 30% when the competing antibody and CIS43 are at equimolar concentrations. In a certain embodiment, the antibody that binds to the same epitope on PfCSP as the CIS43 antibody is a human monoclonal antibody. Such human monoclonal antibodies can be prepared and isolated as described herein.

Human antibodies that bind to the same epitope on PfCSP to which the CIS43 antibody binds can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008). Such antibodies may be prepared, for example, by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology. Human variable regions from intact antibodies generated by such animals may be further modified, e.g., by combining with a different human constant region.

Human antibodies that bind to the same epitope on PfCSP to which the CIS43 antibody binds can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4): 265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3): 185-91 (2005). Human antibodies may also be generated by isolating Fv clone variable domain sequences selected from human-derived phage display libraries. Such variable domain sequences may then be combined with a desired human constant domain.

Antibodies and antigen binding fragments that specifically bind to the same epitope on PfCSP to which the CIS43 antibody binds can also be isolated by screening combinatorial libraries for antibodies with the desired binding characteristics. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

1. Additional Description of Antibodies and Antigen Binding Fragments

The antibody or antigen binding fragment can be a human antibody or fragment thereof. Chimeric antibodies are also provided. The antibody or antigen binding fragment can include any suitable framework region, such as (but not limited to) a human framework region. Human framework regions, and mutations that can be made in a human antibody framework regions, are known (see, for example, in U.S. Pat. No. 5,585,089, which is incorporated herein by reference). Alternatively, a heterologous framework region, such as, but not limited to a mouse or monkey framework region, can be included in the heavy or light chain of the antibodies. (See, for example, Jones et al., Nature, 321 (6069):522-525, 1986; Riechmann et al., *Nature,* 332(6162): 323-327, 1988; Verhoeyen et al., *Science* 239(4847):1534-1536, 1988; Carter et al., *Proc. Natl. Acad. Sci. U.S.A.* 89(10):4285-4289, 1992; Sandhu, *Crit. Rev. Biotechnol.* 12(5-6):437-462, 1992; and Singer et al., *J. Immunol.* 150 (7):2844-2857, 1993.)

The antibody can be of any isotype. The antibody can be, for example, an IgM or an IgG antibody, such as $IgG_1$, $IgG_2$, $IgG_3$, or $IgG_4$. The class of an antibody that specifically binds PfCSP can be switched with another. In one aspect, a nucleic acid molecule encoding $V_L$ or $V_H$ is isolated such that it does not include any nucleic acid sequences encoding the constant region of the light or heavy chain, respectively. A nucleic acid molecule encoding $V_L$ or $V_H$ is then operatively linked to a nucleic acid sequence encoding a $C_L$ or $C_H$ from a different class of immunoglobulin molecule. This can be achieved, for example, using a vector or nucleic acid molecule that comprises a $C_L$ or $C_H$ chain. For example, an antibody that specifically binds PfCSP, that was originally IgG may be class switched to an IgM. Class switching can be used to convert one IgG subclass to another, such as from $IgG_1$ to $IgG_2$, $IgG_3$, or $IgG_4$.

In some examples, the disclosed antibodies are oligomers of antibodies, such as dimers, trimers, tetramers, pentamers, hexamers, septamers, octomers and so on.

The antibody or antigen binding fragment can be derivatized or linked to another molecule (such as another peptide or protein). In general, the antibody or antigen binding fragment is derivatized such that the binding to *P. falciparum* is not affected adversely by the derivatization or labeling. For example, the antibody or antigen binding fragment can be functionally linked (by chemical coupling, genetic fusion, noncovalent association or otherwise) to one or more other molecular entities, such as another antibody (for example, a bi-specific antibody or a diabody), a detectable marker, an effector molecule, or a protein or peptide that can mediate association of the antibody or antibody portion with another molecule (such as a streptavidin core region or a polyhistidine tag).

(a) Binding Affinity

In several embodiments, the antibody or antigen binding fragment specifically binds PfCSP with an affinity (e.g., measured by $K_D$) of no more than $1.0 \times 10^{-8}$ M, no more than $5.0 \times 10^{-8}$ M, no more than $1.0 \times 10^{-9}$ M, no more than $5.0 \times 10^{-9}$ M, no more than $1.0 \times 10^{-10}$ M, no more than $5.0 \times 10^{-10}$ M, or no more than $1.0 \times 10^{-11}$ M. $K_D$ can be measured, for example, by a radiolabeled antigen binding assay (RIA) performed with the Fab version of an antibody of interest and its antigen using known methods. In one assay, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293(4):865-881, 1999). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc™ Catalog #269620), 100 µM or 26 pM [$^{125}$I]-antigen are mixed with serial dilutions of a Fab of interest (e.g., consistent with assessment of the anti-VEGF antibody, Fab-12, in Presta et al., *Cancer Res.* 57(20):4593-4599, 1997). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT™-20; PerkinEmler) is added, and the plates are counted on a TOPCOUNT™ gamma counter (PerkinEmler) for ten minutes. Concentrations of each Fab that give less than or equal to 20% of maximal binding are chosen for use in competitive binding assays.

In another assay, $K_D$ can be measured using surface plasmon resonance assays using a BIACORE®-2000 or a BIACORE®-3000 (BIAcore, Inc., Piscataway, N.J.) at 25° C. with immobilized antigen CMS chips at ~10 response units (RU). Briefly, carboxymethylated dextran biosensor chips (CMS, BIACORE®, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 l/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 l/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

(b) Multispecific Antibodies

In some embodiments, the antibody or antigen binding fragment is included on a multispecific antibody, such as a bi-specific antibody. Such multispecific antibodies can be produced by known methods, such as crosslinking two or more antibodies, antigen binding fragments (such as scFvs) of the same type or of different types. Exemplary methods of making multispecific antibodies include those described in PCT Pub. No. WO2013/163427, which is incorporated by reference herein in its entirety. Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

Various types of multi-specific antibodies are known. Bispecific single chain antibodies can be encoded by a single nucleic acid molecule. Examples of bispecific single chain antibodies, as well as methods of constructing such antibodies are known in the art (see, e.g., U.S. Pat. Nos. 8,076,459, 8,017,748, 8,007,796, 7,919,089, 7,820,166, 7,635,472, 7,575,923, 7,435,549, 7,332,168, 7,323,440, 7,235,641, 7,229,760, 7,112,324, 6,723,538, incorporated by reference herein). Additional examples of bispecific single chain antibodies can be found in PCT application No. WO 99/54440; Mack et al., *J. Immunol.,* 158(8):3965-3970, 1997; Mack et al., *Proc. Natl. Acad. Sci. U.S.A.,* 92(15): 7021-7025, 1995; Kufer et al., *Cancer Immunol. Immunother.,* 45(3-4):193-197, 1997; Löffler et al., Blood, 95(6): 2098-2103, 2000; and Brühl et al., *J. Immunol.,* 166(4): 2420-2426, 2001. Production of bispecific Fab-scFv ("bibody") molecules are described, for example, in Schoonjans et al. (*J. Immunol.,* 165(12):7050-7057, 2000) and Willems et al. (*J. Chromatogr. B Analyt. Technol. Biomed Life Sci.* 786(1-2):161-176, 2003). For bibodies, a scFv molecule can be fused to one of the VL-CL (L) or VH-CH1 chains, e.g., to produce a bibody one scFv is fused to the C-term of a Fab chain.

(c) Fragments

Antigen binding fragments are encompassed by the present disclosure, such as Fab, F(ab')$_2$, and Fv which include a heavy chain and $V_L$ and specifically bind PfCSP. These antibody fragments retain the ability to selectively bind with the antigen and are "antigen-binding" fragments. Non-limiting examples of such fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the $V_L$ and $V_L$ expressed as two chains; and (5) Single chain antibody (such as scFv), defined as a genetically engineered molecule containing the $V_H$ and the $V_L$ linked by a suitable polypeptide linker as a genetically fused single chain molecule (see, e.g., Ahmad et al., *Clin. Dev. Immunol.,* 2012, doi:10.1155/2012/980250; Marbry and Snavely, *IDrugs,* 13(8):543-549, 2010). The intramolecular orientation of the $V_H$-domain and the $V_L$-domain in a scFv, is not decisive for the provided antibodies (e.g., for the provided multispecific antibodies). Thus, scFvs with both possible arrangements ($V_H$-domain-linker domain-$V_L$-domain; $V_L$-domain-linker domain-$V_H$-domain) may be used.

(6) A dimer of a single chain antibody (scFV$_2$), defined as a dimer of a scFV. This has also been termed a "miniantibody."

Methods of making these fragments are known (see for example, Harlow and Lane, *Antibodies: A Laboratory Manual,* 2', Cold Spring Harbor Laboratory, New York, 2013).

Antigen binding fragments can be prepared by proteolytic hydrolysis of the antibody or by expression in a host cell (such as an *E. coli* cell) of DNA encoding the fragment. Antigen binding fragments can also be obtained by pepsin or papain digestion of whole antibodies by conventional methods. For example, antigen binding fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

(d) Variants

In some embodiments, amino acid sequence variants of the antibodies provided herein (such as any one or more of CIS04, CIS06, CIS23, CIS34, CIS42, CIS43, and mAb10) are provided. For example, it may be desirable to improve the binding affinity and/or other biological properties of the antibody Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In some embodiments, antibody variants having one or more amino acid substitutions are provided. Sites of interest for substitutional mutagenesis include the CDRs and the framework regions. Amino acid substitutions may be introduced into an antibody of interest and the products screened for a desired activity, e.g., retained/improved antigen binding, decreased immunogenicity, or improved ADCC or CDC.

The variants typically retain amino acid residues necessary for correct folding and stabilizing between the $V_H$ and the $V_L$ regions, and will retain the charge characteristics of the residues in order to preserve the low pI and low toxicity of the molecules Amino acid substitutions can be made in the $V_H$ and the $V_L$ regions to increase yield.

In some embodiments, the heavy chain of the antibody comprises up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NOs: 1, 3, 5, 7, 9, 11, or 81. In some embodiments, the light chain of the antibody comprises up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NOs: 2, 4, 6, 8, 10, 12, or 82.

In some embodiments, the antibody or antigen binding fragment can include up to 10 (such as up to 1, up to 2, up to 3, up to 4, up to 5, up to 6, up to 7, up to 8, or up to 9) amino acid substitutions (such as conservative amino acid substitutions) in the framework regions of the heavy chain of the antibody, or the light chain of the antibody, or the heavy and light chains of the antibody, compared to a known framework region, or compared to a known framework region, or compared to the framework regions of the CIS06, CIS23, CIS34, CIS42, CIS43, or mAb10 antibody, and maintain the specific binding activity for PfCSP.

In some embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. In some embodiments of the variant $V_H$ and $V_L$ sequences provided above, each CDR either is unaltered, or contains no more than one, two or three amino acid substitutions.

To increase binding affinity of the antibody, the $V_L$ and $V_H$ segments can be randomly mutated, such as within HCDR3 region or the LCDR3 region, in a process analogous to the in vivo somatic mutation process responsible for affinity maturation of antibodies during a natural immune response. Thus in vitro affinity maturation can be accomplished by amplifying VH and $V_L$ regions using PCR primers complementary to the HCDR3 or LCDR3, respectively. In this process, the primers have been "spiked" with a random mixture of the four nucleotide bases at certain positions such that the resultant PCR products encode VH and $V_L$ segments into which random mutations have been introduced into the $V_H$ and/or $V_L$ CDR3 regions. These randomly mutated $V_H$ and $V_L$ segments can be tested to determine the binding affinity for PfCSP. In particular examples, the VH amino acid sequence is one of SEQ ID NOs: 1, 3, 5, 7, 9, 11, or 81. In other examples, the $V_L$ amino acid sequence is one of SEQ ID NOs: 2, 4, 6, 8, 10, 12, or 82. Methods of in vitro affinity maturation are known (see, e.g., Chowdhury, *Methods Mol. Biol.* 207:179-196 (2008)), and Hoogenboom et al. in *Methods in Molecular Biology* 178:1-37 (O'Brien et al., ed., Human Press, Totowa, N.J., (2001).)

In some embodiments, an antibody (such as any one or more of CIS04, CIS06, CIS23, CIS34, CIS42, CIS43, and mAb10) or antigen binding fragment is altered to increase or decrease the extent to which the antibody or antigen binding fragment is glycosylated. Addition or deletion of glycosylation sites may be conveniently accomplished by altering the amino acid sequence such that one or more glycosylation sites is created or removed.

Where the antibody (such as any one or more of CIS04, CIS06, CIS23, CIS34, CIS42, CIS43, and mAb10) comprises an Fc region, the carbohydrate attached thereto may be altered. Native antibodies produced by mammalian cells typically comprise a branched, biantennary oligosaccharide that is generally attached by an N-linkage to Asn297 of the $CH_2$ domain of the Fc region. See, e.g., Wright et al. *Trends Biotechnol.* 15(1):26-32, 1997. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region; however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/

0093621; US 2004/0132140; US 2004/0110704; US 2004/0110282; US 2004/0109865; WO 2003/085119; WO 2003/084570; WO 2005/035586; WO 2005/035778; WO2005/053742; WO 2002/031140; Okazaki et al., *J. Mol. Biol.*, 336(5):1239-1249, 2004; Yamane-Ohnuki et al., *Biotechnol. Bioeng.* 87(5):614-622, 2004. Examples of cell lines capable of producing defucosylated antibodies include Lec 13 CHO cells deficient in protein fucosylation (Ripka et al., *Arch. Biochem. Biophys.* 249(2):533-545, 1986; US Pat. Appl. No. US 2003/0157108 and WO 2004/056312, especially at Example 11), and knockout cell lines, such as alpha-1,6-fucosyltransferase gene, FUT8, knockout CHO cells (see, e.g., Yamane-Ohnuki et al., *Biotechnol. Bioeng.*, 87(5): 614-622, 2004; Kanda et al., *Biotechnol. Bioeng.*, 94(4): 680-688, 2006; and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

In several embodiments, the constant region of the antibody (such as any one or more of CIS04, CIS06, CIS23, CIS34, CIS42, CIS43, and mAb10) comprises one or more amino acid substitutions to optimize in vivo half-life of the antibody. The serum half-life of IgG Abs is regulated by the neonatal Fc receptor (FcRn). Thus, in several embodiments, the antibody comprises an amino acid substitution that increases binding to the FcRn. Several such substitutions are known, such as substitutions at IgG constant regions T250Q and M428L (see, e.g., Hinton et al., *J Immunol.*, 176(1): 346-356, 2006); M428L and N434S (the "LS" mutation, see, e.g., Zalevsky, et al., *Nature Biotechnol.*, 28(2):157-159, 2010); N434A (see, e.g., Petkova et al., *Int. Immunol.*, 18(12):1759-1769, 2006); T307A, E380A, and N434A (see, e.g., Petkova et al., *Int. Immunol.*, 18(12):1759-1769, 2006); and M252Y, S254T, and T256E (see, e.g., Dall'Acqua et al., *J. Biol. Chem.*, 281(33):23514-23524, 2006). The disclosed antibodies and antigen binding fragments can be linked to or comprise a Fc polypeptide including any of the substitutions listed above, for example, the Fc polypeptide can include the M428L and N434S substitutions.

In some embodiments, the constant region of the antibody comprises one or more amino acid substitutions to optimize ADCC. ADCC is mediated primarily through a set of closely related Fcγ receptors. In some embodiments, the antibody comprises one or more amino acid substitutions that increase binding to FcγRIIIa. Several such substitutions are known, such as substitutions at IgG constant regions S239D and I332E (see, e.g., Lazar et al., *Proc. Natl., Acad. Sci. U.S.A.*, 103(11):4005-4010, 2006); and S239D, A330L, and I332E (see, e.g., Lazar et al., *Proc. Natl., Acad. Sci. U.S.A.*, 103(11):4005-4010, 2006).

Combinations of the above substitutions are also included, to generate an IgG constant region with increased binding to FcRn and FcγRIIIa. The combinations increase antibody half-life and ADCC. For example, such combinations include antibodies with the following amino acid substitutions in the Fc region: (1) S239D/I332E and T250Q/M428L; (2) S239D/I332E and M428L/N434S; (3) S239D/I332E and N434A; (4) S239D/I332E and T307A/E380A/N434A; (5) S239D/I332E and M252Y/S254T/T256E; (6) S239D/A330L/I332E and 250Q/M428L; (7) S239D/A330L/I332E and M428L/N434S; (8) S239D/A330L/I332E and N434A; (9) S239D/A330L/I332E and T307A/E380A/N434A; or (10) S239D/A330L/I332E and M252Y/S254T/T256E. In some examples, the antibodies, or an antigen binding fragment thereof is modified such that it is directly cytotoxic to infected cells, or uses natural defenses such as complement, ADCC, or phagocytosis by macrophages.

In some embodiments, an antibody provided herein may be further modified to contain additional nonproteinaceous moieties. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in an application under defined conditions, etc.

B. Conjugates

The antibodies and antigen binding fragments that specifically bind to PfCSP (such as any one or more of CIS04, CIS06, CIS23, CIS34, CIS42, CIS43, and mAb10) can be conjugated to an agent, such as an effector molecule or detectable marker. Both covalent and noncovalent attachment means may be used. Various effector molecules and detectable markers can be used, including (but not limited to) toxins and radioactive agents such as $^{125}I$, $^{32}P$, $^{3}H$ and $^{35}S$ and other labels, target moieties and ligands, etc. The choice of a particular effector molecule or detectable marker depends on the particular target molecule or cell, and the desired biological effect.

The procedure for attaching an effector molecule or detectable marker to an antibody or antigen binding fragment varies according to the chemical structure of the effector. Polypeptides typically contain a variety of functional groups, such as carboxyl (—COOH), free amine (—NH$_2$) or sulfhydryl (—SH) groups, which are available for reaction with a suitable functional group on a polypeptide to result in the binding of the effector molecule or detectable marker. Alternatively, the antibody or antigen binding fragment is derivatized to expose or attach additional reactive functional groups. The derivatization may involve attachment of any of a number of known linker molecules, such as those available from Thermo Fisher Scientific, Waltham, Mass. and MilliporeSigma Corporation, St. Louis, Mo. The linker is capable of forming covalent bonds to both the antibody or antigen binding fragment and to the effector molecule or detectable marker. Suitable linkers include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side chains (such as through a disulfide linkage to cysteine) or the alpha carbon, or through the amino, and/or carboxyl groups of the terminal amino acids.

In view of the large number of methods that have been reported for attaching a variety of radiodiagnostic compounds, radiotherapeutic compounds, labels (such as enzymes or fluorescent molecules), toxins, and other agents to antibodies, a suitable method for attaching a given agent to an antibody or antigen binding fragment or other polypeptide can be determined.

In some embodiments, the antibody or antigen binding fragment can be conjugated with effector molecules such as small molecular weight drugs such as Monomethyl Auristatin E (MMAE), Monomethyl Auristatin F (MMAF), maytansine, maytansine derivatives, including the derivative of maytansine known as DM1 (also known as mertansine), or other agents to make an antibody drug conjugate (ADC). In several embodiments, conjugates of an antibody or antigen binding fragment and one or more small molecule toxins, such as a calicheamicin, maytansinoids, dolastatins, auristatins, a trichothecene, and CC1065, and the derivatives of these toxins that have toxin activity, are provided.

The antibody or antigen binding fragment can be conjugated with a detectable marker; for example, a detectable marker capable of detection by ELISA, spectrophotometry, flow cytometry, microscopy or diagnostic imaging techniques (such as CT, computed axial tomography (CAT), MRI, magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, green fluorescent protein (GFP), and yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present, the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

The antibody or antigen binding fragment can be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitope recognized by a secondary reporter (such as leucine zipper pair sequences, binding sites for secondary antibodies, metal binding domains, epitope tags).

The antibody or antigen binding fragment can also be conjugated with a radiolabeled amino acid, for example, for diagnostic purposes. For instance, the radiolabel may be used to detect PfCSP expressing cells by radiography, emission spectra, or other diagnostic techniques. Examples of labels for polypeptides include, but are not limited to, the following radioisotopes: $^{3}H$, $^{14}C$, $^{35}S$, $^{90}Y$, $^{99m}Tc$, $^{111}In$, $^{125}I$, $^{131}I$. The radiolabels may be detected, for example, using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The average number of effector molecule or detectable marker moieties per antibody or antigen binding fragment in a conjugate can range, for example, from 1 to 20 moieties per antibody or antigen binding fragment. In some embodiments, the average number of effector molecules or detectable marker moieties per antibody or antigen binding fragment in a conjugate range from about 1 to about 2, from about 1 to about 3, about 1 to about 8; from about 2 to about 6; from about 3 to about 5; or from about 3 to about 4. The loading (for example, effector molecule per antibody ratio) of a conjugate may be controlled in different ways, for example, by: (i) limiting the molar excess of effector molecule-linker intermediate or linker reagent relative to antibody, (ii) limiting the conjugation reaction time or temperature, (iii) partial or limiting reducing conditions for cysteine thiol modification, (iv) engineering by recombinant techniques the amino acid sequence of the antibody such that the number and position of cysteine residues is modified for control of the number or position of linker-effector molecule attachments.

C. Polynucleotides and Expression

Nucleic acid molecules (for example, cDNA or RNA molecules) encoding the amino acid sequences of antibodies, antigen binding fragments, and conjugates that specifically bind to PfCSP (such as any one or more of CIS04, CIS06, CIS23, CIS34, CIS42, CIS43, and mAb10), are provided. Nucleic acids encoding these molecules can readily be produced using the amino acid sequences provided herein (such as the CDR sequences and $V_H$ and $V_L$ sequences), sequences available in the art (such as framework or constant region sequences), and the genetic code. In several embodiments, a nucleic acid molecules can encode the $V_H$, the $V_L$, or both the $V_H$ and $V_L$ (for example in a bicistronic expression vector) of a disclosed antibody or antigen binding fragment. In several embodiments, the nucleic acid molecules can be expressed in a host cell (such as a mammalian cell) to produce a disclosed antibody or antigen binding fragment.

The genetic code can be used to construct a variety of functionally equivalent nucleic acid sequences, such as nucleic acids which differ in sequence but which encode the same antibody sequence, or encode a conjugate or fusion protein including the $V_L$ and/or $V_H$ nucleic acid sequence.

In a non-limiting example, an isolated nucleic acid molecule encodes the $V_H$ of a disclosed antibody or antigen binding fragment and comprises the nucleic acid sequence set forth as any one of SEQ ID NOs: 47, 49, 51, 53, 55, 57, or 83. In a non-limiting example, an isolated nucleic acid molecule encodes the $V_L$ of a disclosed antibody or antigen binding fragment and comprises the nucleic acid sequence set forth as any one of SEQ ID NOs: 48, 50, 52, 54, 56, 58, or 84. In a non-limiting example, an isolated nucleic acid molecule encodes the $V_H$ and $V_L$ of a disclosed antibody or antigen binding fragment and comprises the nucleic acid sequences set forth as any one of SEQ ID NOs: 47 and 48, respectively, 49 and 50, respectively, 51 and 52, respectively, 53 and 54, respectively, 55 and 56, respectively, 57 and 58, respectively, or 83 and 84, respectively.

Nucleic acid molecules encoding the antibodies, antigen binding fragments, and conjugates that specifically bind to PfCSP can be prepared by any suitable method including, for example, cloning of appropriate sequences or by direct chemical synthesis by standard methods. Chemical synthesis produces a single stranded oligonucleotide. This can be converted into double stranded DNA by hybridization with a complementary sequence or by polymerization with a DNA polymerase using the single strand as a template.

Exemplary nucleic acids can be prepared by cloning techniques. Examples of appropriate cloning and sequencing techniques can be found, for example, in Green and Sambrook (*Molecular Cloning: A Laboratory Manual*, 4$^{th}$ ed., New York: Cold Spring Harbor Laboratory Press, 2012) and Ausubel et al. (Eds.) (*Current Protocols in Molecular Biology*, New York: John Wiley and Sons, including supplements, 2017).

Nucleic acids can also be prepared by amplification methods Amplification methods include the polymerase chain reaction (PCR), the ligase chain reaction (LCR), the transcription-based amplification system (TAS), and the self-sustained sequence replication system (3SR).

The nucleic acid molecules can be expressed in a recombinantly engineered cell such as bacteria, plant, yeast, insect and mammalian cells. The antibodies, antigen binding fragments, and conjugates can be expressed as individual proteins including the $V_H$ and/or $V_L$ (linked to an effector molecule or detectable marker as needed), or can be expressed as a fusion protein. Methods of expressing and purifying antibodies and antigen binding fragments are known and further described herein (see, e.g., Al-Rubeai (Ed.), *Antibody Expression and Production*, Dordrecht; New York: Springer, 2011). An immunoadhesin can also be expressed. Thus, in some examples, nucleic acids encoding a $V_H$ and $V_L$, and immunoadhesin are provided. The nucleic acid sequences can optionally encode a leader sequence.

To create a scFv the $V_H$- and $V_L$-encoding DNA fragments can be operatively linked to another fragment encoding a flexible linker, e.g., encoding the amino acid sequence $(Gly_4-Ser)_3$, such that the VH and $V_L$ sequences can be expressed as a contiguous single-chain protein, with the $V_L$ and $V_H$ domains joined by the flexible linker (see, e.g., Bird et al., *Science*, 242(4877):423-426, 1988; Huston et al., *Proc. Natl. Acad. Sci. U.S.A.*, 85(16):5879-5883, 1988; McCafferty et al., *Nature*, 348:552-554, 1990; Kontermann and Dübel (Eds.), *Antibody Engineering*, Vols. 1-2, 2$^{nd}$ ed., Springer-Verlag, 2010; Greenfield (Ed.), *Antibodies: A Laboratory Manual*, 2$^{nd}$ ed. New York: Cold Spring Harbor Laboratory Press, 2014). Optionally, a cleavage site can be included in a linker, such as a furin cleavage site.

The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to PfCSP and another antigen. The encoded $V_H$ and $V_L$ optionally can include a furin cleavage site between the $V_H$ and $V_L$ domains.

One or more DNA sequences encoding the antibodies, antigen binding fragments, or conjugates can be expressed in vitro by DNA transfer into a suitable host cell. The cell may be prokaryotic or eukaryotic. Numerous expression systems available for expression of proteins including *E. coli*, other bacterial hosts, yeast, and various higher eukaryotic cells such as the COS, CHO, HeLa and myeloma cell lines, can be used to express the disclosed antibodies and antigen binding fragments. Methods of stable transfer, meaning that the foreign DNA is continuously maintained in the host, are known in the art. Hybridomas expressing the antibodies of interest are also encompassed by this disclosure.

The expression of nucleic acids encoding the antibodies and antigen binding fragments described herein can be achieved by operably linking the DNA or cDNA to a promoter (which is either constitutive or inducible), followed by incorporation into an expression cassette. The promoter can be any promoter of interest, including a cytomegalovirus promoter. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signals for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, for example, a strong promoter to direct transcription, a ribosome binding site for translational initiation (e.g., internal ribosomal binding sequences), and a transcription/translation terminator. For *E. coli*, this can include a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

Modifications can be made to a nucleic acid encoding a polypeptide described herein without diminishing its biological activity. Some modifications can be made to facilitate the cloning, expression, or incorporation of the targeting molecule into a fusion protein. Such modifications include, for example, termination codons, sequences to create conveniently located restriction sites, and sequences to add a methionine at the amino terminus to provide an initiation site, or additional amino acids (such as poly His) to aid in purification steps.

Once expressed, the antibodies, antigen binding fragments, and conjugates can be purified according to standard procedures in the art, including ammonium sulfate precipitation, affinity columns, column chromatography, and the like (see, generally, Simpson et al. (Eds.), *Basic methods in Protein Purification and Analysis: A Laboratory Manual*, New York: Cold Spring Harbor Laboratory Press, 2009). The antibodies, antigen binding fragment, and conjugates need not be 100% pure. Once purified, partially or to homogeneity as desired, if to be used prophylatically, the polypeptides should be substantially free of endotoxin.

Methods for expression of antibodies, antigen binding fragments, and conjugates, and/or refolding to an appropriate active form, from mammalian cells, and bacteria such as *E. coli* have been described and are applicable to the antibodies disclosed herein. See, e.g., Greenfield (Ed.), *Antibodies: A Laboratory Manual*, $2^{nd}$ ed. New York: Cold Spring Harbor Laboratory Press, 2014, Simpson et al. (Eds.), *Basic methods in Protein Purification and Analysis: A Laboratory Manual*, New York: Cold Spring Harbor Laboratory Press, 2009, and Ward et al., *Nature* 341(6242): 544-546, 1989.

D. Methods and Compositions

1. Inhibiting *P. falciparum* Infection

Methods are disclosed herein for the inhibition of a *P. falciparum* infection in a subject. The methods include administering to the subject an effective amount (that is, an amount effective to inhibit *P. falciparum* infection in the subject) of a disclosed antibody (such as any one or more of CIS04, CIS06, CIS23, CIS34, CIS42, CIS43, and mAb10), antigen binding fragment, conjugate, or a nucleic acid encoding such an antibody, antigen binding fragment, or conjugate, to a subject at risk of a *P. falciparum* infection. The methods can be used pre-exposure or post-exposure.

*P. falciparum* infection does not need to be completely eliminated or inhibited for the method to be effective. For example, the method can decrease *P. falciparum* infection by a desired amount, for example by at least 10%, at least 20%, at least 50%, at least 60%, at least 70%, at least 80%, at least 90%, at least 95%, at least 98%, or even at least 100% (elimination or prevention of detectable *P. falciparum* infection) as compared to *P. falciparum* infection in the absence of the treatment. In some embodiments, the subject can also be treated with an effective amount of an additional agent, such as anti-malaria agent.

In some embodiments, administration of an effective amount of a disclosed antibody, antigen binding fragment, conjugate, or nucleic acid molecule, inhibits the establishment of *P. falciparum* infection and/or subsequent *P. falciparum* disease progression in a subject, which can encompass any statistically significant reduction in *P. falciparum* activity (for example, growth or invasion) or symptoms of *P. falciparum* infection in the subject.

Antibodies and antigen binding fragments thereof are typically administered by intravenous infusion. Doses of the antibody or antigen binding fragment vary, but generally range between about 0.5 mg/kg to about 50 mg/kg, such as a dose of about 1 mg/kg, about 5 mg/kg, about 10 mg/kg, about 20 mg/kg, about 30 mg/kg, about 40 mg/kg, or about 50 mg/kg. In some embodiments, the dose of the antibody or antigen binding fragment can be from about 0.5 mg/kg to about 5 mg/kg, such as a dose of about 1 mg/kg, about 2 mg/kg, about 3 mg/kg, about 4 mg/kg or about 5 mg/kg. The antibody or antigen binding fragment is administered according to a dosing schedule determined by a medical practitioner. In some examples, the antibody or antigen binding fragment is administered weekly, every two weeks, every three weeks or every four weeks.

In some embodiments, the method of inhibiting *P. falciparum* infection in a subject further comprises administration of one or more additional agents to the subject. Additional agents of interest include, but are not limited to, anti-malaria agents.

In some embodiments, the method of inhibiting *P. falciparum* infection in a subject comprises administration of a first antibody that specifically binds to PfCSP as disclosed herein (such as any one of CIS04, CIS06, CIS23, CIS34, CIS42, CIS43, and mAb10) and a second antibody that that specifically binds to PfCSP. In some embodiments, the first antibody is CIS43 and the second antibody is mAb10 as disclosed herein.

In some embodiments, a subject is administered DNA or RNA encoding a disclosed antibody to provide in vivo antibody production, for example using the cellular machinery of the subject. Administration of nucleic acid constructs is known in the art and taught, for example, in U.S. Pat. Nos. 5,643,578, 5,593,972 and 5,817,637. U.S. Pat. No. 5,880,103 describes several methods of delivery of nucleic acids encoding proteins to an organism. One approach to administration of nucleic acids is direct administration with plasmid DNA, such as with a mammalian expression plasmid. The nucleotide sequence encoding the disclosed antibody, or antigen binding fragments thereof, can be placed under the control of a promoter to increase expression. The methods include liposomal delivery of the nucleic acids. Such methods can be applied to the production of an antibody, or antigen binding fragments thereof. In some embodiments, a disclosed antibody or antigen binding fragment is expressed in a subject using the pVRC8400 vector (described in Barouch et al., *J. Virol.*, 79(14), 8828-8834, 2005, which is incorporated by reference herein).

In several embodiments, a subject (such as a human subject at risk of *P. falciparum* infection) can be administered an effective amount of an AAV viral vector that includes one or more nucleic acid molecules encoding a disclosed antibody or antigen binding fragment. The AAV viral vector is designed for expression of the nucleic acid molecules encoding a disclosed antibody or antigen binding fragment, and administration of the effective amount of the AAV viral vector to the subject leads to expression of an effective amount of the antibody or antigen binding fragment in the subject. Non-limiting examples of AAV viral vectors that can be used to express a disclosed antibody or antigen binding fragment in a subject include those provided in Johnson et al., *Nat. Med.*, 15(8):901-906, 2009 and Gardner et al., *Nature*, 519(7541):87-91, 2015, each of which is incorporated by reference herein in its entirety.

In one embodiment, a nucleic acid encoding a disclosed antibody, or antigen binding fragment thereof, is introduced directly into tissue. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter.

Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

Single or multiple administrations of a composition including a disclosed PfCSP-specific antibody, antigen binding fragment, conjugate, or nucleic acid molecule encoding such molecules, can be administered depending on the dosage and frequency as required and tolerated by the patient. The dosage can be administered once, but may be applied periodically until either a desired result is achieved or until side effects warrant discontinuation of therapy. Generally, the dose is sufficient to inhibit *P. falciparum* infection without producing unacceptable toxicity to the patient.

Data obtained from cell culture assays and animal studies can be used to formulate a range of dosage for use in humans. The dosage normally lies within a range of circulating concentrations that include the $ED_{50}$, with little or minimal toxicity. The dosage can vary within this range depending upon the dosage form employed and the route of administration utilized. The effective dose can be determined from cell culture assays and animal studies.

The PfCSP-specific antibody, antigen binding fragment, conjugate, or nucleic acid molecule encoding such molecules, or a composition including such molecules, can be administered to subjects in various ways, including local and systemic administration, such as, e.g., by injection subcutaneously, intravenously, intra-arterially, intraperitoneally, intramuscularly, intradermally, or intrathecally. In an embodiment, the antibody, antigen binding fragment, conjugate, or nucleic acid molecule encoding such molecules, or a composition including such molecules, is administered by a single subcutaneous, intravenous, intra-arterial, intraperitoneal, intramuscular, intradermal or intrathecal injection once a day. The antibody, antigen binding fragment, conjugate, or nucleic acid molecule encoding such molecules, or a composition including such molecules, can also be administered by direct injection at or near the site of disease. A further method of administration is by osmotic pump (e.g., an Alzet pump) or mini-pump (e.g., an Alzet mini-osmotic pump), which allows for controlled, continuous and/or slow-release delivery of the antibody, antigen binding fragment, conjugate, or nucleic acid molecule encoding such molecules, or a composition including such molecules, over a pre-determined period. The osmotic pump or mini-pump can be implanted subcutaneously, or near a target site.

2. Compositions

Compositions are provided that include one or more of the PfCSP-specific antibody, antigen binding fragment, conjugate, or nucleic acid molecule encoding such molecules, that are disclosed herein in a carrier. In some embodiments, the composition include the CIS43 antibody and one or more additional CSP-specific antibody, such as mAb10 as disclosed herein. The compositions are useful, for example, for example, for the inhibition or detection of a *P. falciparum* infection. The compositions can be prepared in unit dosage forms for administration to a subject. The amount and timing of administration are at the discretion of the administering physician to achieve the desired purposes. The PfCSP-specific antibody, antigen binding fragment, conjugate, or nucleic acid molecule encoding such molecules can be formulated for systemic or local administration. In one example, the PfCSP-specific antibody, antigen binding fragment, conjugate, or nucleic acid molecule encoding such molecules, is formulated for parenteral administration, such as intravenous administration.

In some embodiments, the antibody, antigen binding fragment, or conjugate thereof, in the composition is at least 70% (such as at least 75%, at least 80%, at least 85%, at least 90%, at least 95%, at least 96%, at least 97%, at least 98% or at least 99%) pure. In some embodiments, the composition contains less than 10% (such as less than 5%, less than 4%, less than 3%, less than 2%, less than 1%, less than 0.5%, or even less) of macromolecular contaminants, such as other mammalian (e g, human) proteins.

The compositions for administration can include a solution of the PfCSP-specific antibody, antigen binding fragment, conjugate, or nucleic acid molecule encoding such molecules, dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical composition for intravenous administration includes about 0.01 to about 30 mg/kg of antibody or antigen binding fragment or conjugate per subject per day (or the corresponding dose of a conjugate including the antibody or antigen binding fragment). Actual methods for preparing administrable compositions are known and are described in more detail in such publications as *Remington: The Science and Practice of Pharmacy,* $22^{nd}$ ed., London, UK: Pharmaceutical Press, 2013. In some embodiments, the composition can be a liquid formulation including one or more antibodies, antigen binding fragments (such as an antibody or antigen binding fragment that specifically binds to PfCSP), in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml.

Antibodies, or an antigen binding fragment thereof or a conjugate or a nucleic acid encoding such molecules, can be provided in lyophilized form and rehydrated with sterile water before administration, although they are also provided in sterile solutions of known concentration. The antibody solution, or an antigen binding fragment or a nucleic acid encoding such antibodies or antigen binding fragments, can then be added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of Rituximab in 1997. Antibodies, antigen binding fragments, conjugates, or a nucleic acid encoding such molecules, can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30-minute period if the previous dose was well tolerated.

Controlled-release parenteral formulations can be made as implants, oily injections, or as particulate systems. For a broad overview of protein delivery systems see, Banga, *Therapeutic Peptides and Proteins: Formulation, Processing, and Delivery Systems,* Lancaster, Pa.: Technomic Publishing Company, Inc., 1995. Particulate systems include microspheres, microparticles, microcapsules, nanocapsules, nanospheres, and nanoparticles. Microcapsules contain the active protein agent, such as a cytotoxin or a drug, as a central core. In microspheres, the active protein agent is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, *Colloidal Drug Delivery Systems*, J. Kreuter (Ed.), New York, N.Y.: Marcel Dekker, Inc., pp. 219-342, 1994; and Tice and Tabibi, *Treatise on Controlled Drug Delivery: Fundamentals, Optimization, Applications*, A. Kydonieus (Ed.), New York, N.Y.: Marcel Dekker, Inc., pp. 315-339, 1992.

Polymers can be used for ion-controlled release of the antibody compositions disclosed herein. Various degradable and nondegradable polymeric matrices for use in controlled drug delivery are known in the art (Langer, *Acc. Chem. Res.* 26(10):537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.*, 9(3):425-434, 1992; and Pec et al., *J. Parent. Sci. Tech.*, 44(2):58-65, 1990). Alternatively, hydroxyapatite has been used as a microcarrier for controlled release of proteins (Ijntema et al., *Int. J. Pharm.* 112(3):215-224, 1994). In yet another aspect, liposomes are used for controlled release as well as drug targeting of the lipid-capsulated drug (Betageri et al., *Liposome Drug Delivery Systems*, Lancaster, Pa.: Technomic Publishing Co., Inc., 1993). Numerous additional systems for controlled delivery of active protein agent are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

3. Methods of Detection and Diagnosis

Methods are also provided for the detection of the presence of PfCSP in vitro or in vivo. In one example, the presence of PfCSP is detected in a biological sample from a subject, and can be used to identify a subject with *P. falciparum* infection. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. The method of detection can include contacting a cell or sample, with an antibody or antigen binding fragment that specifically binds to PfCSP, or conjugate thereof (e.g. a conjugate including a detectable marker) under conditions sufficient to form an immune complex, and detecting the immune complex (e.g., by detecting a detectable marker conjugated to the antibody or antigen binding fragment.

In one embodiment, the antibody or antigen binding fragment is directly labeled with a detectable marker. In another embodiment, the antibody that binds *P. falciparum* (the primary antibody) is unlabeled and a secondary antibody or other molecule that can bind the primary antibody is utilized for detection. The secondary antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially. Suitable labels for the antibody, antigen binding fragment or secondary antibody are known and described above, and include various enzymes, prosthetic groups, fluorescent materials, luminescent materials, magnetic agents and radioactive materials.

In some embodiments, the disclosed antibodies or antigen binding fragments thereof are used to test vaccines. For example to test if a vaccine composition including a PfCSP or fragment thereof assumes a conformation including the epitope of a disclosed antibody. Thus provided herein is a method for testing a vaccine, wherein the method includes contacting a sample containing the vaccine, such as a PfCSP immunogen, with a disclosed antibody or antigen binding fragment under conditions sufficient for formation of an immune complex, and detecting the immune complex, to detect the vaccine with an PfCSP immunogen including the epitope in the sample. In one example, the detection of the immune complex in the sample indicates that vaccine component, such as a PfCSP immunogen assumes a conformation capable of binding the antibody or antigen binding fragment.

III. EXAMPLES

The following example is provided to illustrate particular features of certain embodiments, but the scope of the claims should not be limited to those features exemplified.

Example 1

A Human Monoclonal Antibody Prevents Malaria Infection and Defines a Site of Vulnerability on *Plasmodium falciparum* Circumsporozoite Protein This example illustrates identification and characterization of human antibodies that specifically bind to PfCSP and neutralize *P. falciparum* infection.

The *P. falciparum* circumsporozoite protein (PfCSP) covers the surface of the infecting sporozoites and has a critical role in invasion of hepatocytes required for initiation of malaria infection. PfCSP is comprised of an N terminal domain, which contains a highly conserved pentapeptide sequence, termed region I (RI), followed by an immunodominant central repeat region, consisting of ~40 NANP motifs and up to 4 NVDP motifs, and a C-terminal domain (FIG. 1A). High titer antibodies against the NANP repeats have been associated with some clinical protection following vaccination with RTS,S/ASO1, a truncated formulation of PfCSP containing only NANP repeats and the C-terminal region (Casares et al., *Vaccine* 28, 4880-4894, 2010; White et al., *PLoS One* 8, e61395, 2013; Stoute et al., *N Engl J Med* 336, 86-91, 1997). Moreover, human monoclonal antibodies (mAbs) against the NANP repeats isolated from subjects vaccinated with RTS,S/ASO1 protect mice following malaria challenge (Foquet et al., *J Clin Invest*, 124, 140-144, 2014; Oyen et al., *Proc Natl Acad Sci USA*, 114, E10438-E10445, 2017). However, until now, there are limited data characterizing human mAbs to sites other than the repetitive NANP motifs that mediate sterile protection in mice. Thus, isolation of antibodies from humans exposed to whole sporozoites by vaccination or infection provides a sensitive approach to identify such mAbs since full length PfCSP is presented in its native conformation.

Figure 1B:
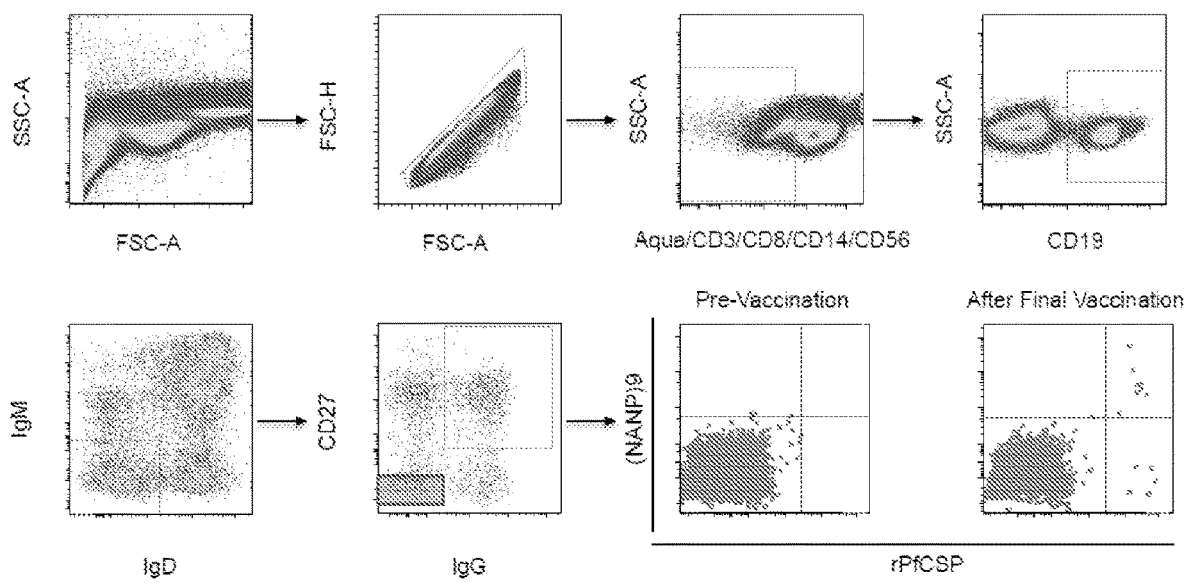
Figure 1C:
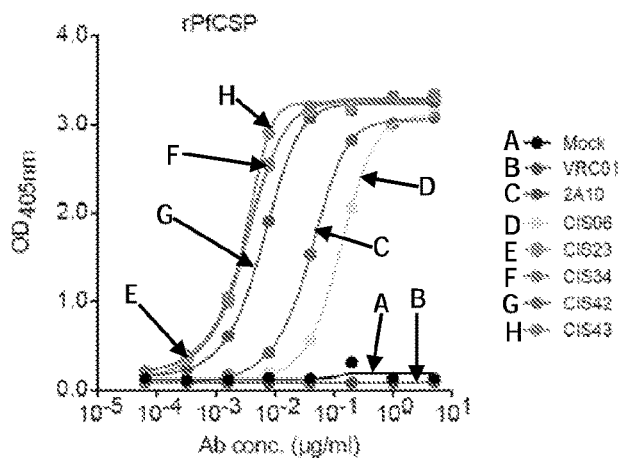
Figure 1D:
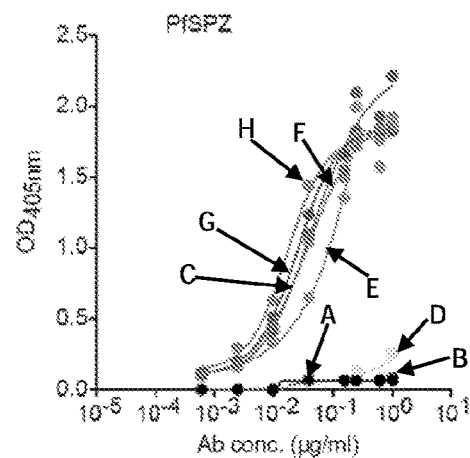
Figure 1E:
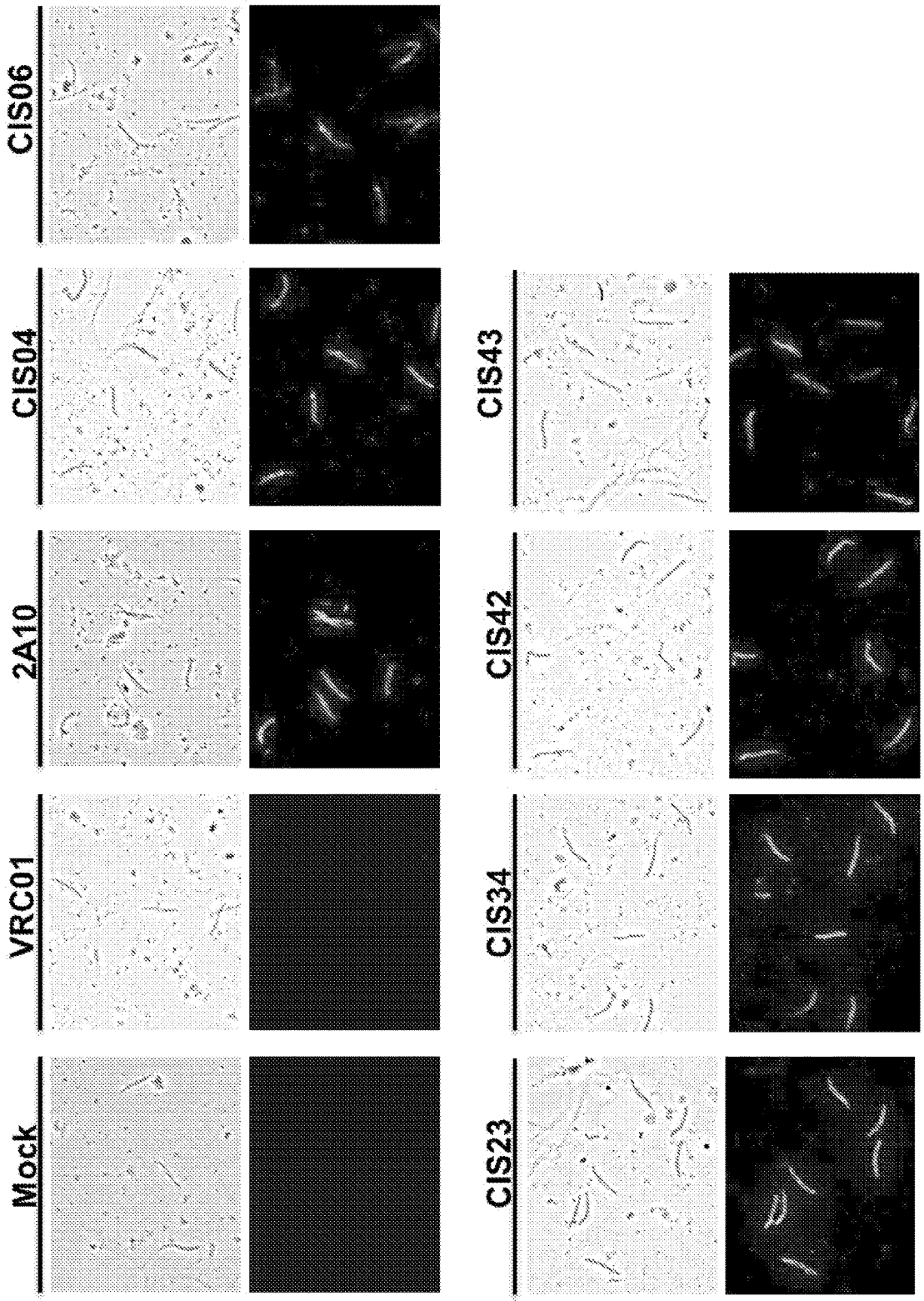
Figure 5A:
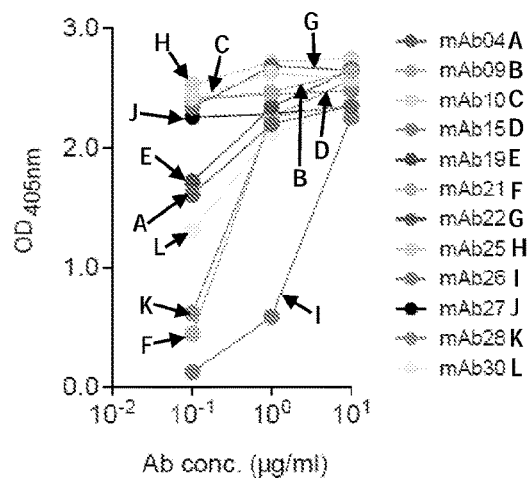
FIGS. 5A-5G. Binding specificity, in vitro inhibitory function and epitope mapping of PfCSP mAbs.

To isolate PfCSP mAbs, two different experimental approaches were used. The first approach used recombinant PfCSP (rPfCSP) and (NANP)$_9$ (SEQ ID NO: 79) repeat peptide probes to directly identify and sort PfCSP-reactive IgG+ memory B cells from peripheral blood two weeks after the final vaccination (FIG. 1B) of a malaria naïve subject who received an attenuated sporozoite vaccine (Sanaria® PfSPZ Vaccine). The subject had high serum PfCSP antibody titers with inhibition of sporozoite invasion of hepatocytes in vitro and was protected after controlled human malaria infection. Four of the five mAbs (CIS23, CIS34, CIS42, CIS43) showed dose-dependent binding to rPfCSP and PfSPZ by ELISA, with $EC_{50}s$, ranging from 0.003-0.134 µg/ml and 0.017-0.08 µg/ml, respectively (FIGS. 1C-1D). These antibodies also bound PfSPZ by immunofluorescent assay (IFA) (FIG. 1E). Additional PfCSP mAbs were generated by a second approach using plasmablasts derived from two subjects immunized with the PfSPZ Vaccine. This method provides a direct and unbiased approach for isolating mAbs against PfCSP and other PfSPZ proteins. Plasmablasts were sorted 7 days after the third immunization without any antigen-specific probe, and Ig heavy and light chain sequences recovered from mRNA were expressed as recombinant antibodies. Of the 141 mAbs expressed, 68 were rPfCSP-specific as determined by ELISA and twelve Abs were selected for additional analysis (FIG. 5A).

Each PfCSP mAb isolated utilized distinct $V_H$ and $V_L$ gene families with 95 to 100% and 89 to 100% nucleotide identity to their germline for heavy and light chains, respectively. All PfCSP mAbs had canonical third heavy complementarity-determining region (CDRH3) lengths ranging from 12-17 amino acid residues (FIG. 9). For the PfCSP mAbs isolated from plasmablasts, the IGVH3 gene family predominated, particularly $V_H3-33$ (FIG. 9).

The protein sequences and Kabat CDRs of the heavy and light chain variable regions of the CIS04, CIS06, CIS23, CIS34, CIS42, CIS43, and mAb10 antibodies are shown in FIG. 1F.

Figure 5B:
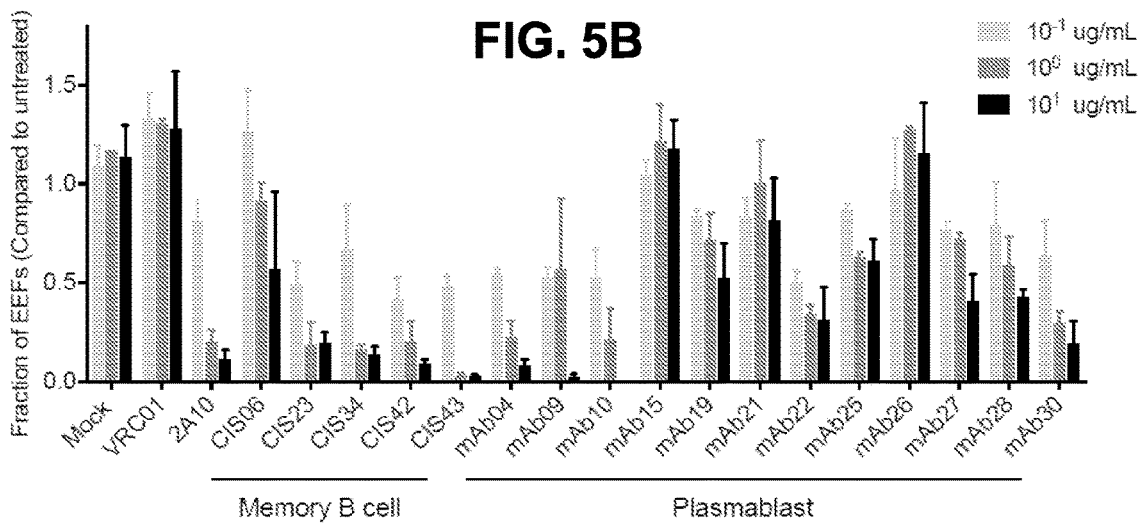

The functional inhibitory capacity of the PfCSP mAbs was first assessed using an in vitro model of liver stage development with primary human hepatocytes (see March et al., *Cell Host Microbe*, 14, 104-115, 2013; March et al., *Nat Protoc*, 10, 2027-2053, 2015). This analysis provides a high throughput initial screening assay to assess hundreds of antibodies to downselect those showing inhibition for in vivo protection studies. Four of the PfCSP mAbs (CIS23, CIS34, CIS42, and CIS43) isolated by the rPfCSP probe sorted memory B cells mAbs and three (mAb04, mAb09, and mAb10) of the PfCSP-specific antibodies isolated from plasmablasts showed dose-dependent inhibition (FIG. 5B).

Figure 2A:
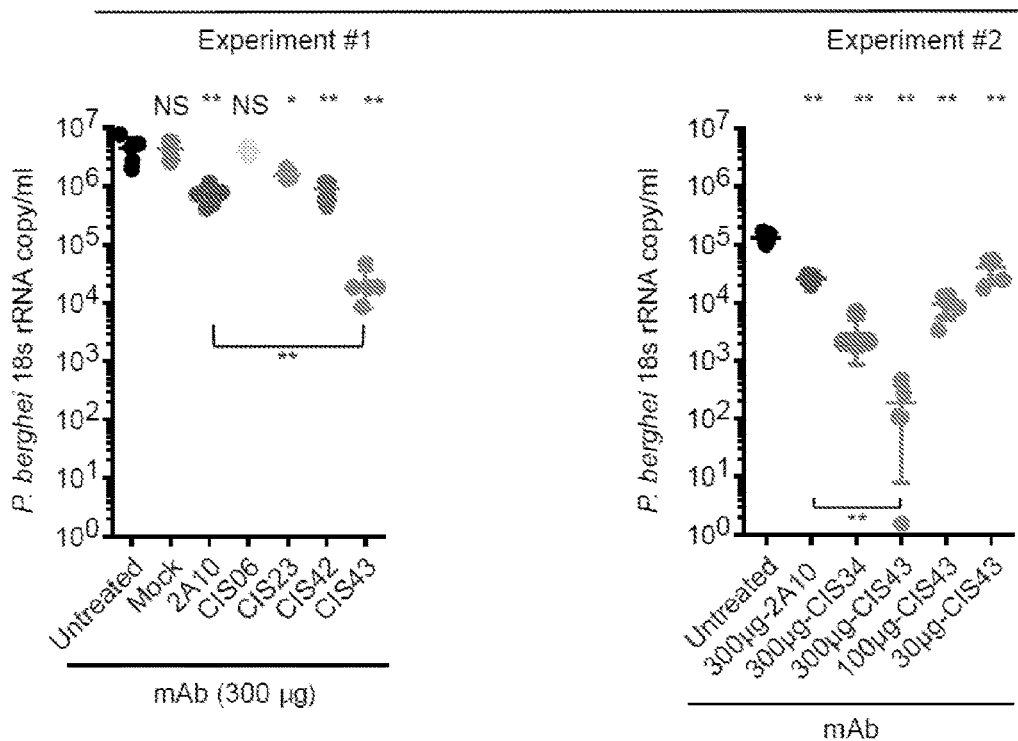
Figure 2B:
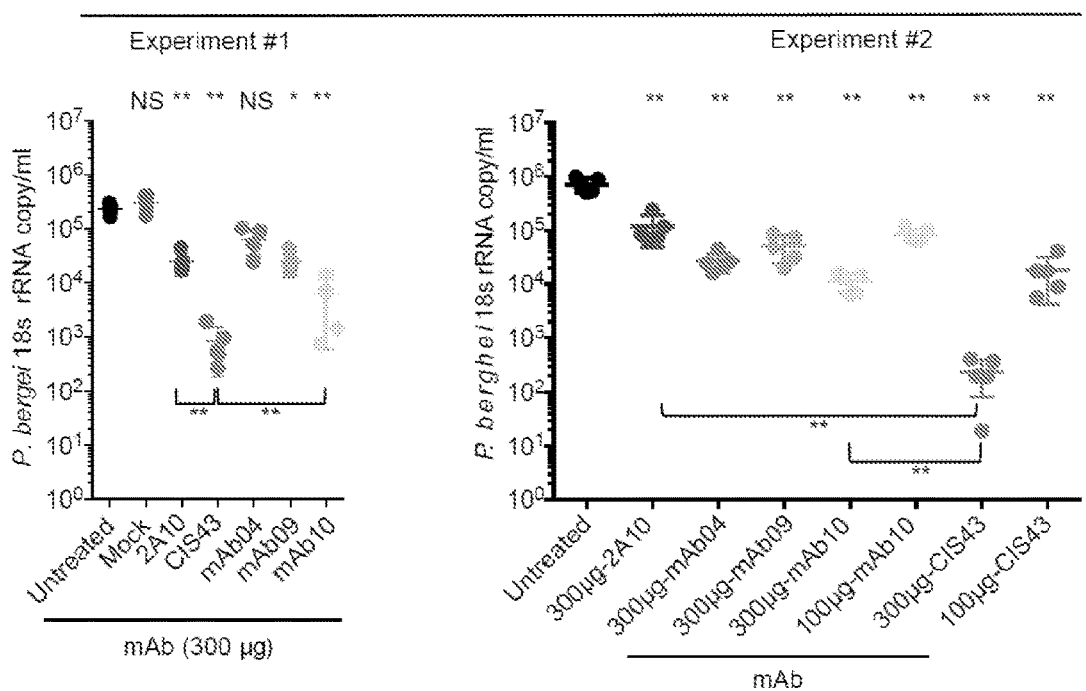

Functional inhibition of the PfCSP mAbs was then assessed in vivo using two different and complementary mouse models of malaria infection. The first model uses a transgenic strain of *P. berghei* (Pb) in which the endogenous PbCSP has been replaced with full-length PfCSP (Pb-PfCSP) (Espinosa et al., npj *Vaccines*, 2, 2017). As rodents are permissive for Pb infection, this allows assessment of the PfCSP mAbs in the context of a natural infection in a normal mouse. In this model, all antibodies that showed in vitro inhibition were tested. Passive transfer of mAb CIS43 led to the highest reduction (~2-4 logs) in a dose-dependent manner in parasite liver-stage burden (p<0.008) (FIGS. 2A and 2B), followed by mAb CIS34 which showed ~2 log reduction compared to untreated mice (p<0.008) following intravenous infection (FIG. 2A). The inhibitory capacity of the three mAbs (mAb04, mAb09, and mAb10) isolated from plasmablasts that showed in vitro inhibition was then assessed (FIG. 5B). Of these antibodies, mAb10 showed the most significant reduction (~1-2 log) in parasite liver-stage burden compared to untreated mice (p<0.008) (FIG. 2B). In all 4 experiments shown, mAb CIS43 showed significantly better protection than mAb2A10 or mAb10 (p<0.008). Of note, mAbs CIS42, mAb04, and mAb09 which all had potent inhibitory activity in vitro, did not significantly reduce liver burden in vivo. These data are consistent with prior reports showing a similar discrepancy (Sack et al. npj *Vaccines*, 2, 2017; Kublin et al., *Sci Transl Med*, 9, 2017) and highlight the importance and greater stringency of the in vivo studies for demonstrating protective efficacy. Since malaria infection is naturally transmitted by mosquito bites and antibodies to PfCSP have inhibitory effects in the skin (Vanderberg and Frevert, *Int J Parasitol*, 34, 991-996, 2004), the protective capacity of the PfCSP mAbs was further assessed in mice challenged with mosquitoes. In two independent experiments, all 14 mice that received mAb CIS43, 13 of 14 mice that received mAb CIS34, and 7 of 7 mice that received mAb10 were parasite-free in blood (p<0.0001). In contrast, only 2 of 7 mice that received mAb2A10 were parasite-free (FIG. 2C). Last, serum antibody levels following passive transfer were approximately 150-200 µg/ml for all PfCSP mAbs (FIG. 2D). These data show that differences in protective efficacy of the mAbs in vivo are related to binding specificity and affinity rather than differing amounts of antibody in vivo.

Figure 2G:
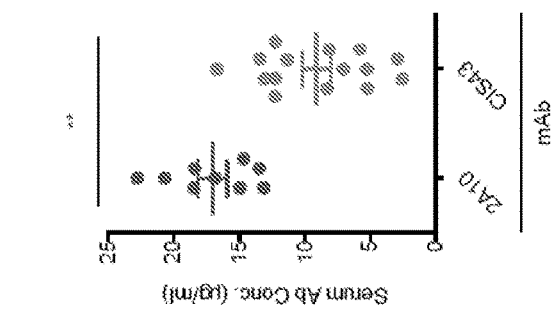
Figure 2F:
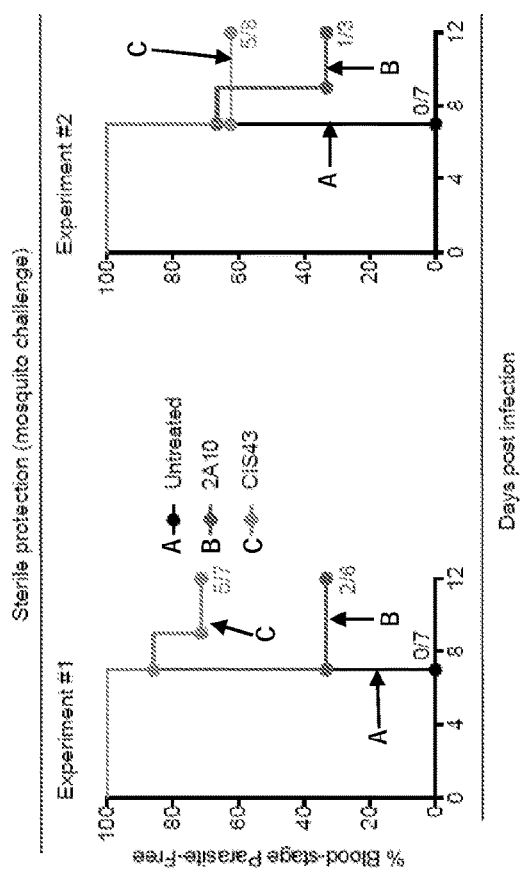
Figure 2E:
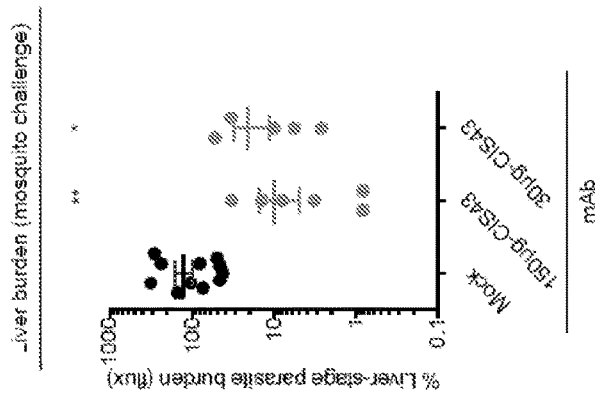

To substantiate the in vivo protective capacity of PfCSP mAbs in the second mouse model, human liver-chimeric mice (FRG-huHep) permissive to infection with *P. falciparum* were used (Sack et al., *Infect Immun*, 82, 808-817, 2014). Given the limited availability of these mice, studies focused on mAb CIS43 which was consistently the most protective antibody in vivo (FIGS. 2A and 2B). In the first experiment following passive transfer of mAb CIS43, mice were challenged with 50 infected mosquitoes. This high dose challenge model provides a dynamic range to assess reduction in parasite load in the liver as a first demonstration of protection. Compared to the mock control mAb-treated mice, there was a dose-dependent reduction (p<0.001 and p<0.041, respectively) of *P. falciparum* in liver burden by 80%-90% by mAb CIS43 (FIG. 2E). Challenge was also performed using 5 infected mosquitoes and transferred human red blood cells to assess sterile protection in blood. In two independent experiments, 10 of 15 mice were parasite-free (p<0.0002) in blood by passive transfer of only 50 µg of mAb CIS43 (FIG. 2F) with serum levels of ~10 µg/ml at the time of mosquito challenge (FIG. 2G). Collectively, these data show that mAb CIS43 conferred high-level, sterile protection in two mouse models of malaria infection.

Figure 3A:
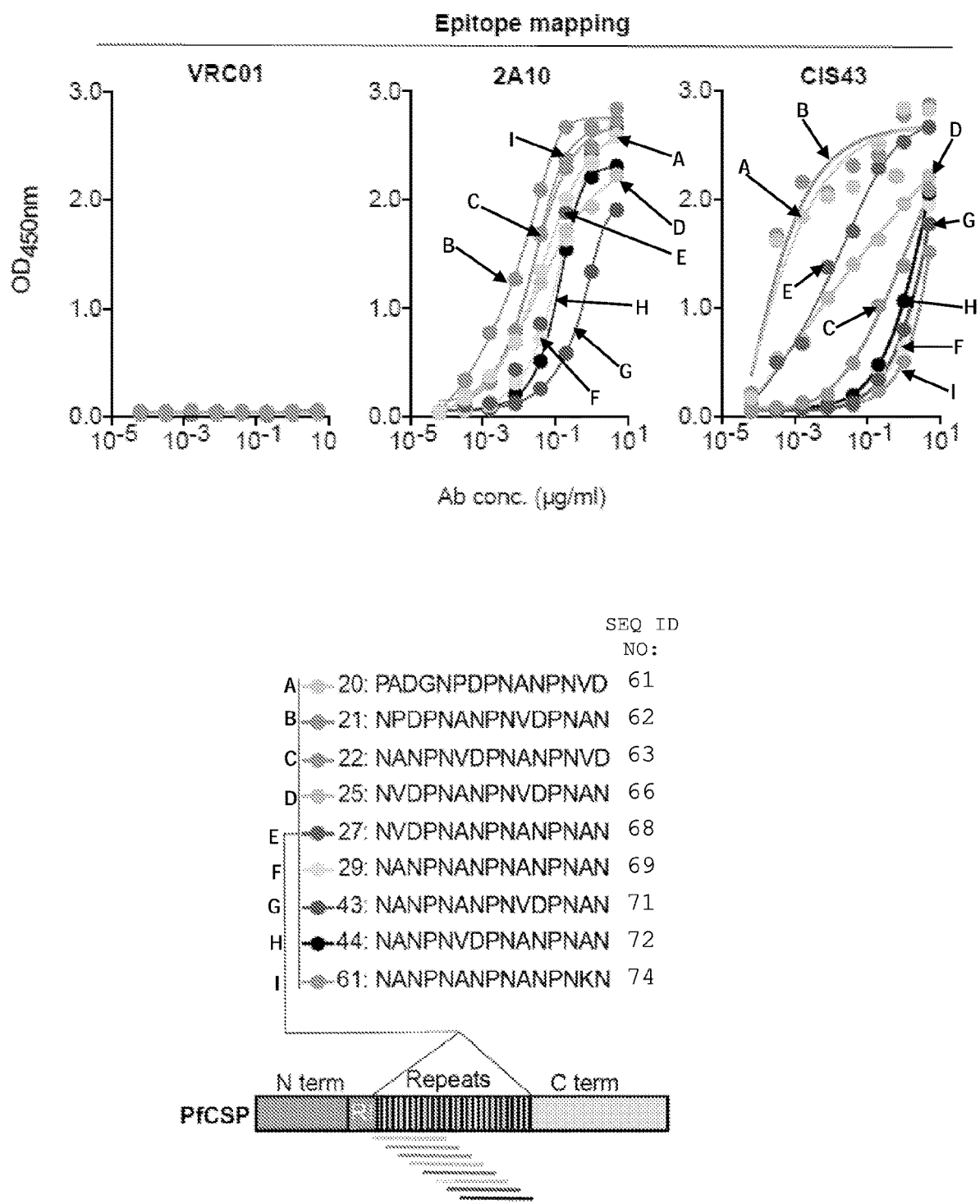
Figure 3B:
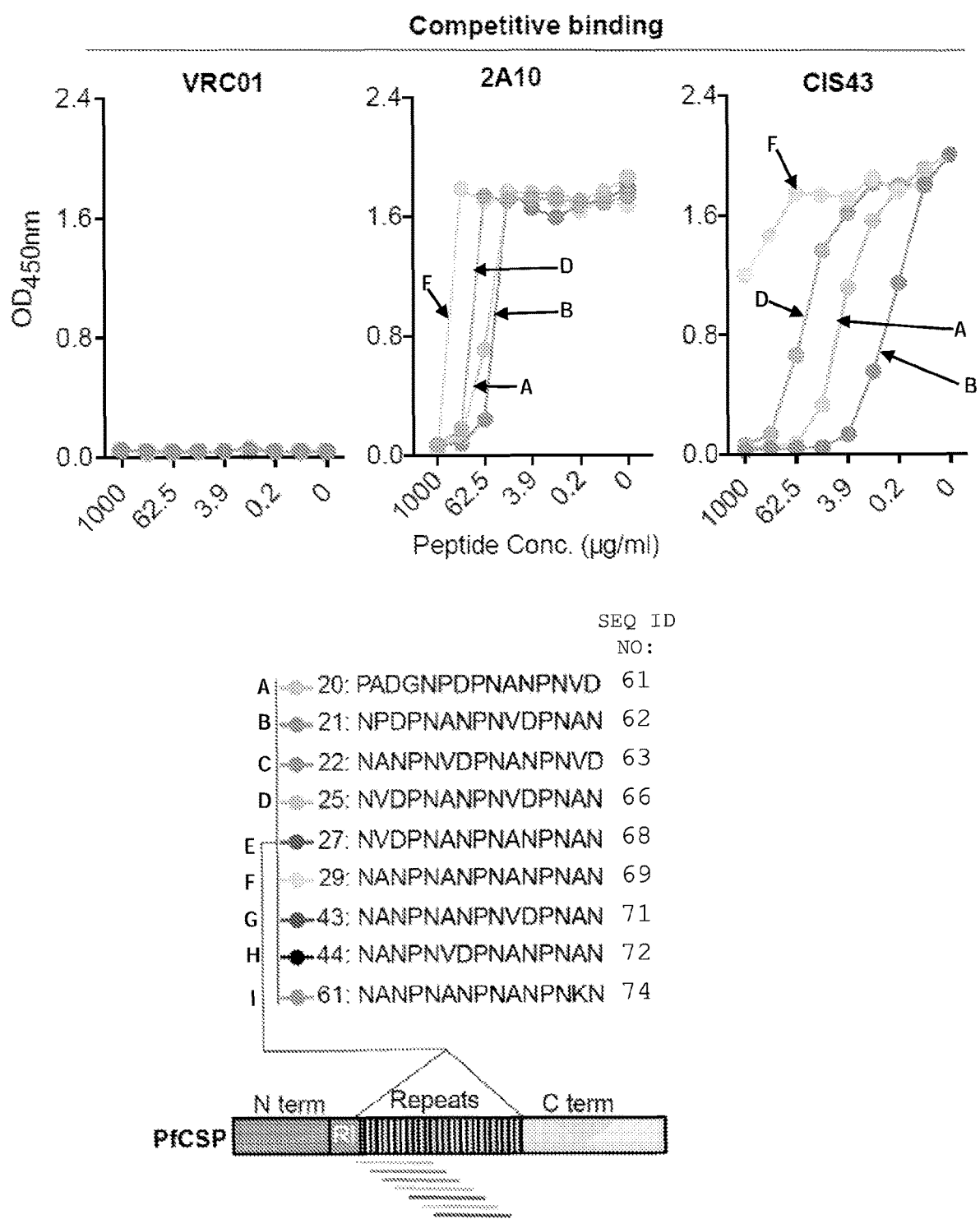
Figure 5C:
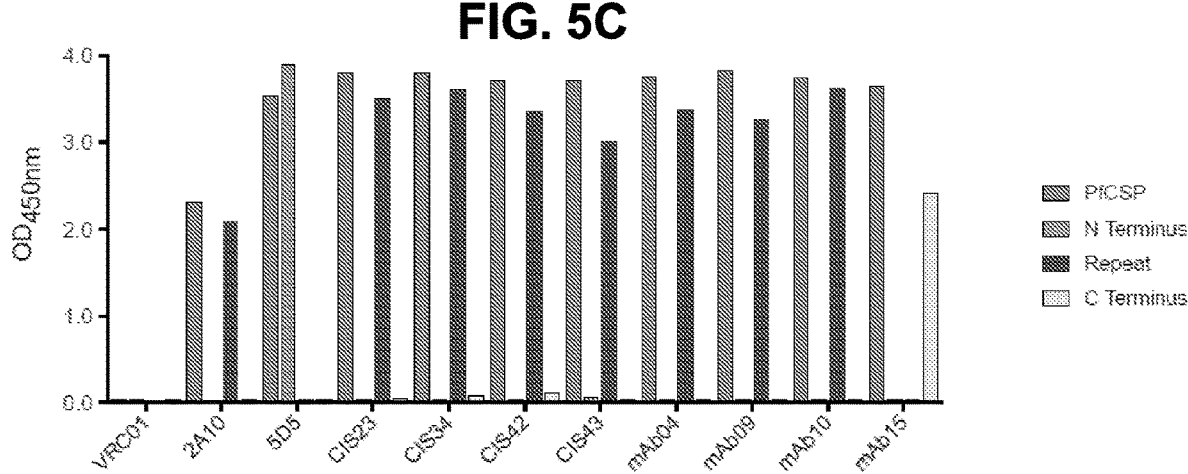
Figure 5D:
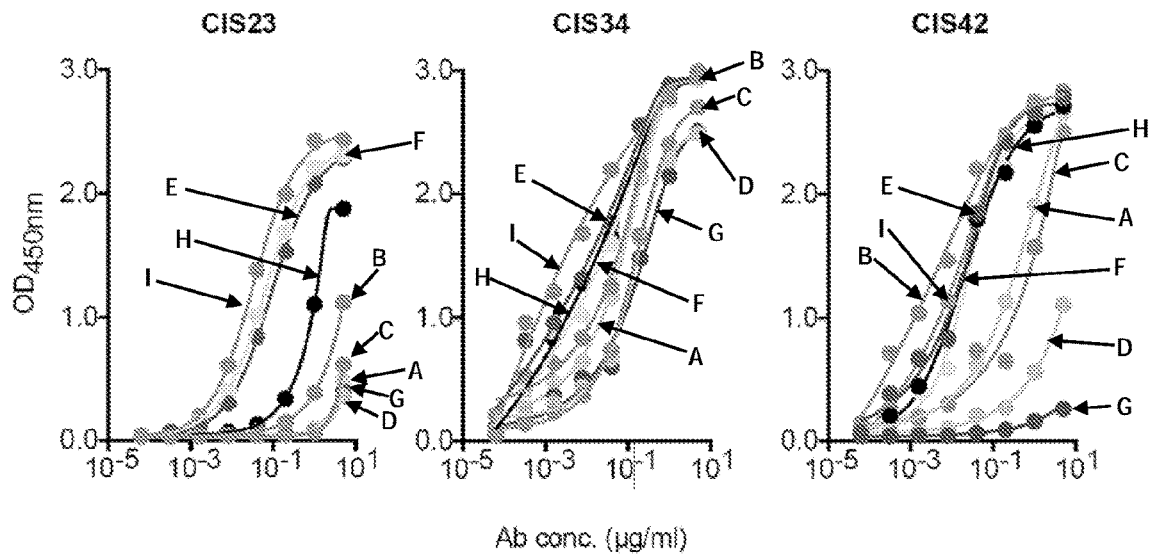
Figure 5E:
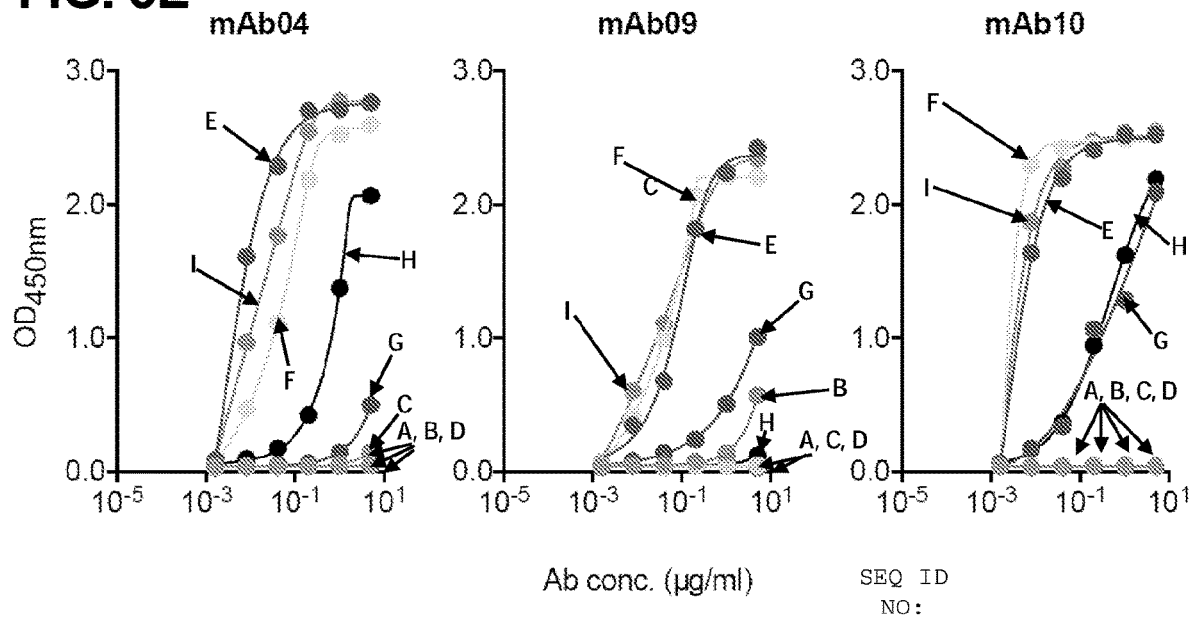
Figure 5F:
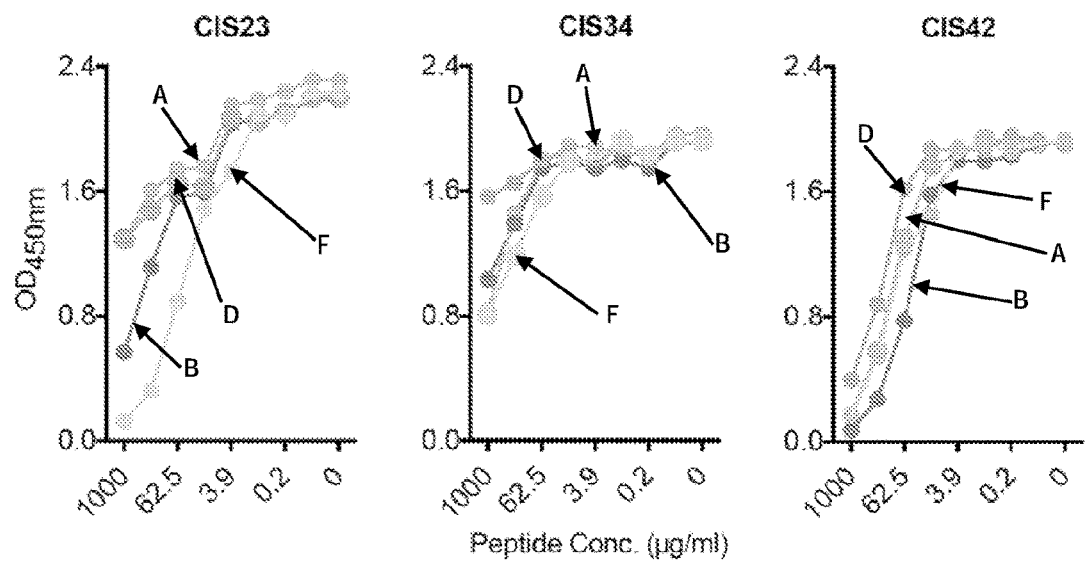
Figure 5G:
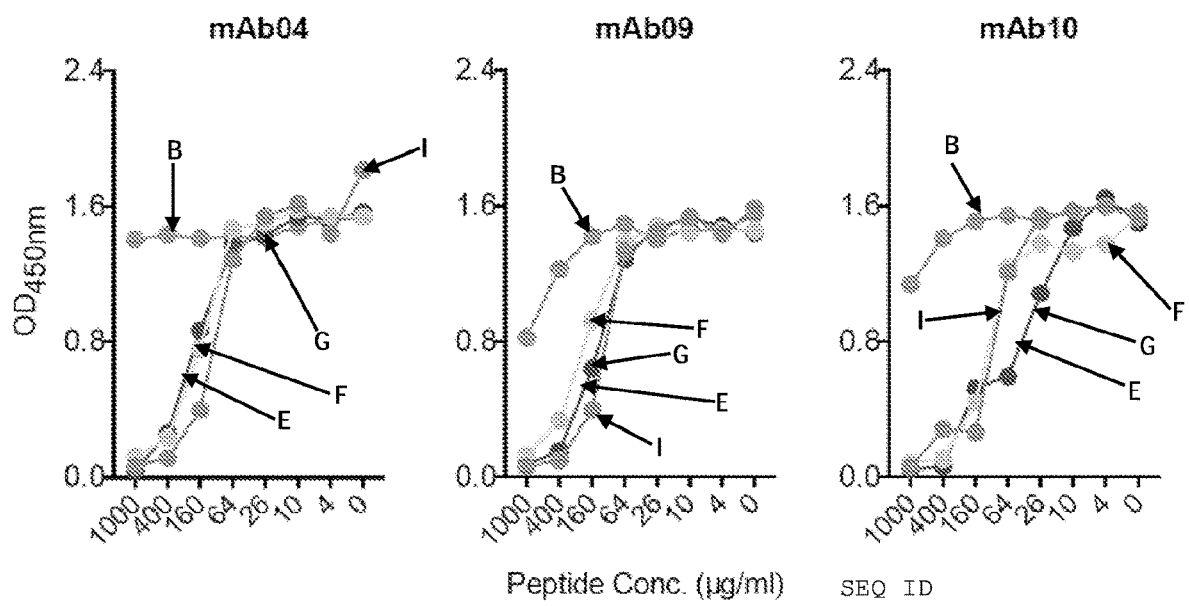

To understand the mechanisms for the differential in vivo potency of the PfCSP mAbs, binding analysis by mapping to PfCSP and structural studies were performed. Binding specificity was first assessed against polypeptides representing the N-terminal, central repeat and C-terminal regions. All PfCSP mAbs tested for in vivo function bound only within the central repeats highlighting the immunodominance of this region by the PfSPZ Vaccine (FIG. 5C). Finer mapping using a series of 15-mer linear peptides overlapping by 11 amino acids encompassing the central repeat region (peptides 20-61, residues 97-276) (FIG. 3A, FIG. 5D,E) showed that PfCSP mAbs isolated from plasmablasts bound only NVDP and NANP repeats (FIG. 5E). In striking contrast, mAb CIS43 showed the highest binding to peptide 20 ($P_{97}$ADGNPDPNANPNVD$_{111}$) and peptide 21 ($N_{101}$PDPNANPNVDPNAN$_{115}$) with an $EC_{50}<0.0001$ µg/ml, and reduced binding to the representative NANP-repeat peptide 29 ($N_{132}$ANPNANPNANPNAN$_{147}$) with an $EC_{50}>5.0$ µg/ml (FIG. 3A, FIG. 5D). Furthermore, preincubation of mAb CIS43 with peptides 20 or 21 significantly inhibited binding to rPfCSP in a dose-dependent manner (FIG. 3B) with IC$_{50}$ values of 4.4 µg/ml or 0.29 µg/ml, respectively. This striking inhibitory capacity of peptide 21 for mAb CIS43 binding to rPfCSP was not observed with the other PfCSP mAbs (FIG. 3B and FIG. 5E, 5G).

Figure 3C:
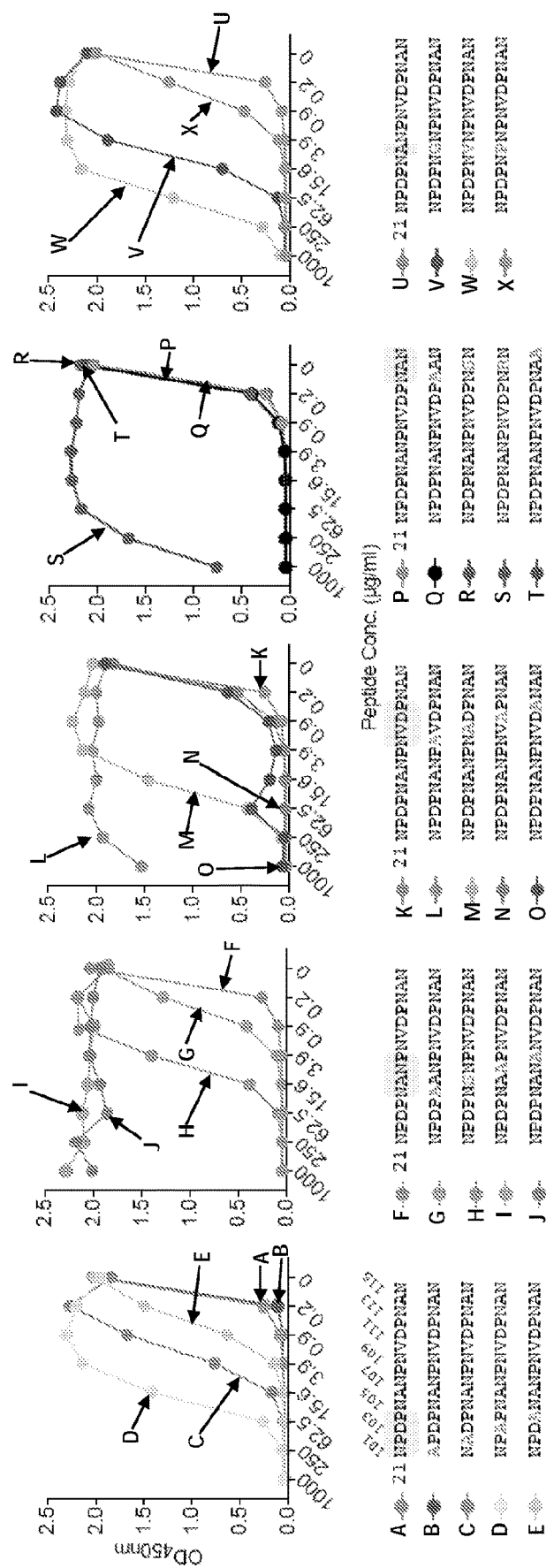

Alanine scanning mutagenesis of peptide 21 was done to define the critical residues for mAb CIS43 binding to rPfCSP. If an alanine occurred in the original sequence, it was substituted with either an arginine, glycine, proline, serine, or valine (FIG. 3C). Alanine substitutions at Asn$_{107}$, Pro$_{108}$, or Asn$_{109}$, abrogated the capacity of peptide 21 to compete for mAb CIS43 binding to rPfCSP and immobilized PfSPZ (FIGS. 3C and 3D). Mutating Pro$_{102}$, Asp$_{103}$, Ala$_{106}$, Val$_{110}$ also affected binding. Moreover, peptide 25, which is identical to peptide 21, except for the substitution of a single residue at position 102 (from Pro to Val), limited the inhibitory capacity of peptide 21, suggesting a key role for Pro$_{102}$ interacting with mAb CIS43 (FIGS. 3B and 3C).

Consistent with the epitope mapping data, mAb CIS43 had the highest apparent affinity (<0.001 nM) to peptide 21 compared to the other PfCSP mAbs (range<0.001-6.06 nM) as assessed by biolayer inferometry (see the following Table).

induce conformational changes of rPfCSP, which influence the stoichiometry of the binding events of mAb CIS43.

To determine the molecular interactions of epitope binding by mAb CIS43, CIS43 Fab was co-crystallized with peptides 20, 21, 25 and 29 since these peptides differentially competed with binding to rPfCSP (FIG. 3B). Attempts to co-crytallize rPfCSP with mAb CIS43 were unsuccessful likely due to the multivalent stoichiometry of antibody binding to rPfCSP and the flexibility of this protein. Crystals were obtained that diffracted X-rays to 2.4 Å, 1.8 Å, 2.0 Å and 2.2 Å, respectively. These peptides inserted into a hydrophobic groove formed at the interface of the heavy and light chains, which is positively charged, tyrosine-rich and involved all the CDRs (FIGS. 4A, 4D, FIG. 10, FIG. 11). Some conformational changes were observed: residues Trp47$_{HC}$, Arg58$_{HC}$ and Pro100$_{HC}$ of the heavy chain and residues Tyr27$_{LC}$, Asn28$_{LC}$, Trp50$_{LC}$, Tyr91$_{LC}$ and Tyr92$_{LC}$ of the light chain showed movements when bound to different peptides. While peptides 20, 21 and 25 adopted a similar overall conformation (except at the N-terminus of peptide 25 and at all the C-termini), peptide 29 adopted a clearly different conformation. The β-1 turn conformation

TABLE 2

K$_D$ of antibody binding to CSP and peptides 21 and 29 determined by biolayer inferometry.

| | Apparent K$_D$ of mAb binding | | | | | | |
|---|---|---|---|---|---|---|---|
| | VRC01 | 2A10 | CIS06 | CIS23 | CIS34 | CIS42 | CIS43 |
| CSP on sensor | N/A | 0.15 nM | N/A | 1.55 nM | 1.50 nM | 0.76 nM | 0.91 nM |
| Peptide 21 on sensor | N/A | 0.06 nM | N/A | 6.06 nM | 0.09 nM | 1.69 nM | <0.001 nM |
| Peptide 29 on sensor | N/A | 1.77 nM | N/A | 2.18 nM | 1.03 nM | 2.21 nM | 4.66 nM |

Figure 4A:
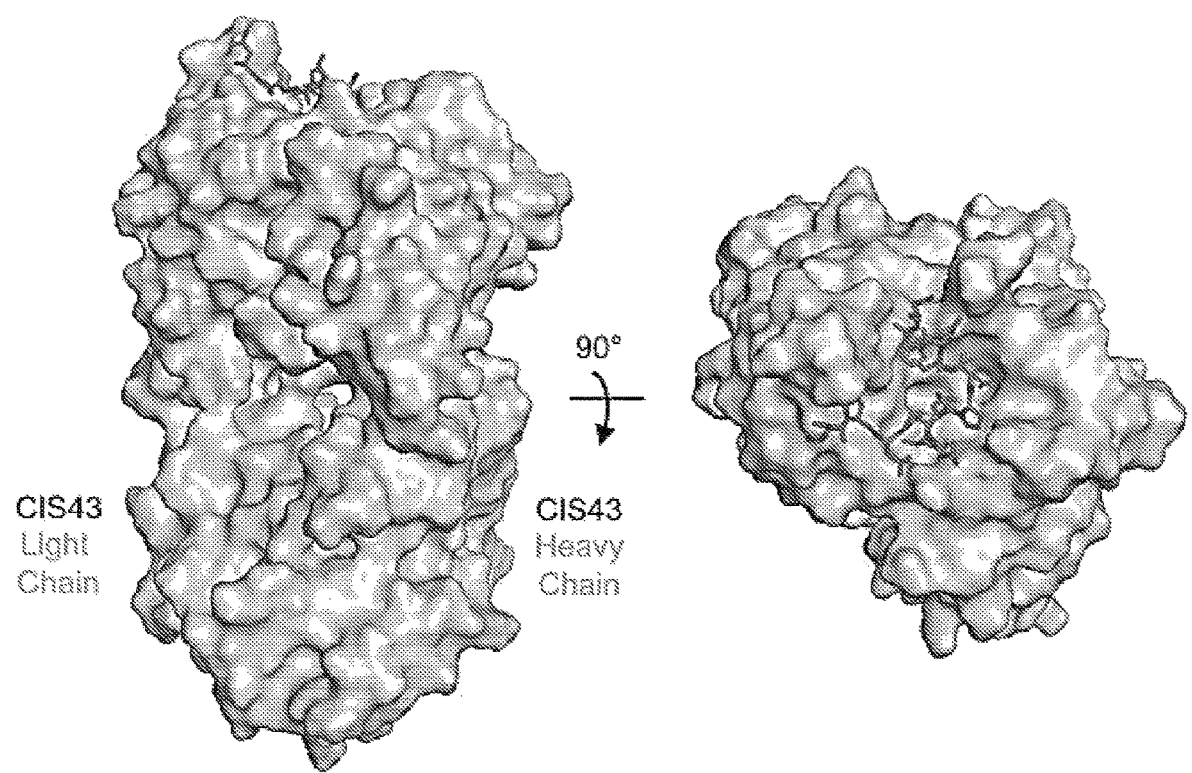
Figure 4C:
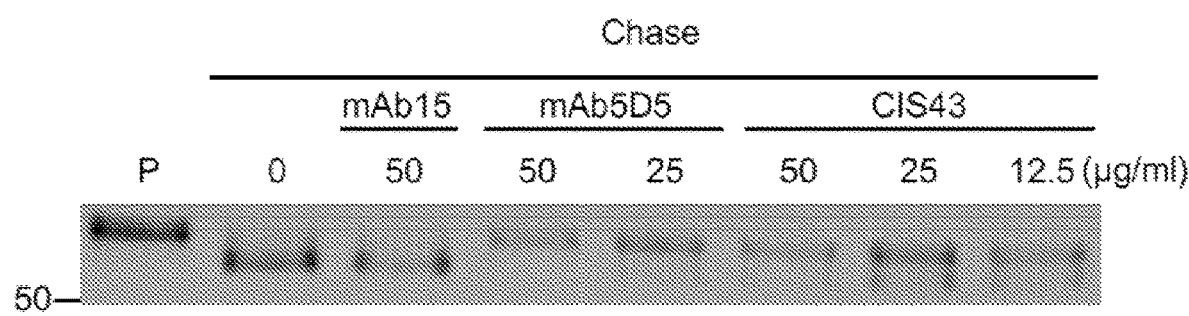
Figure 4D:
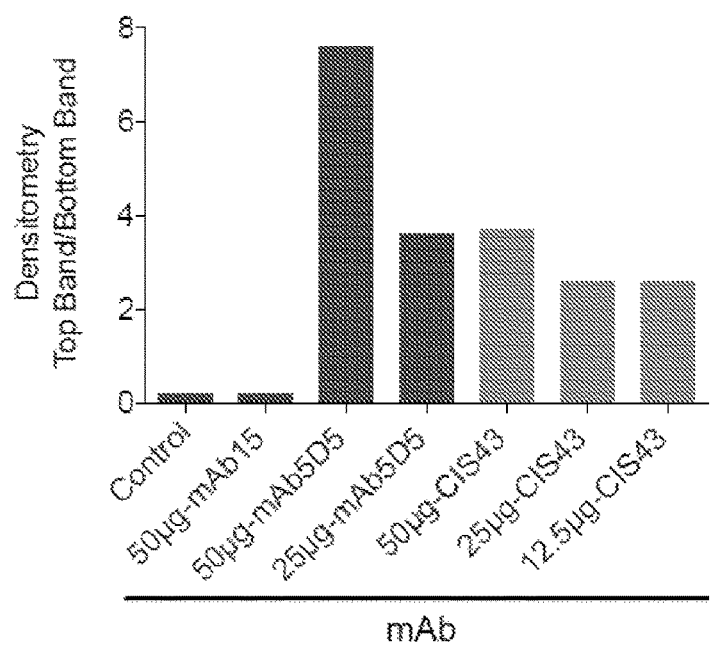
Figure 6A:
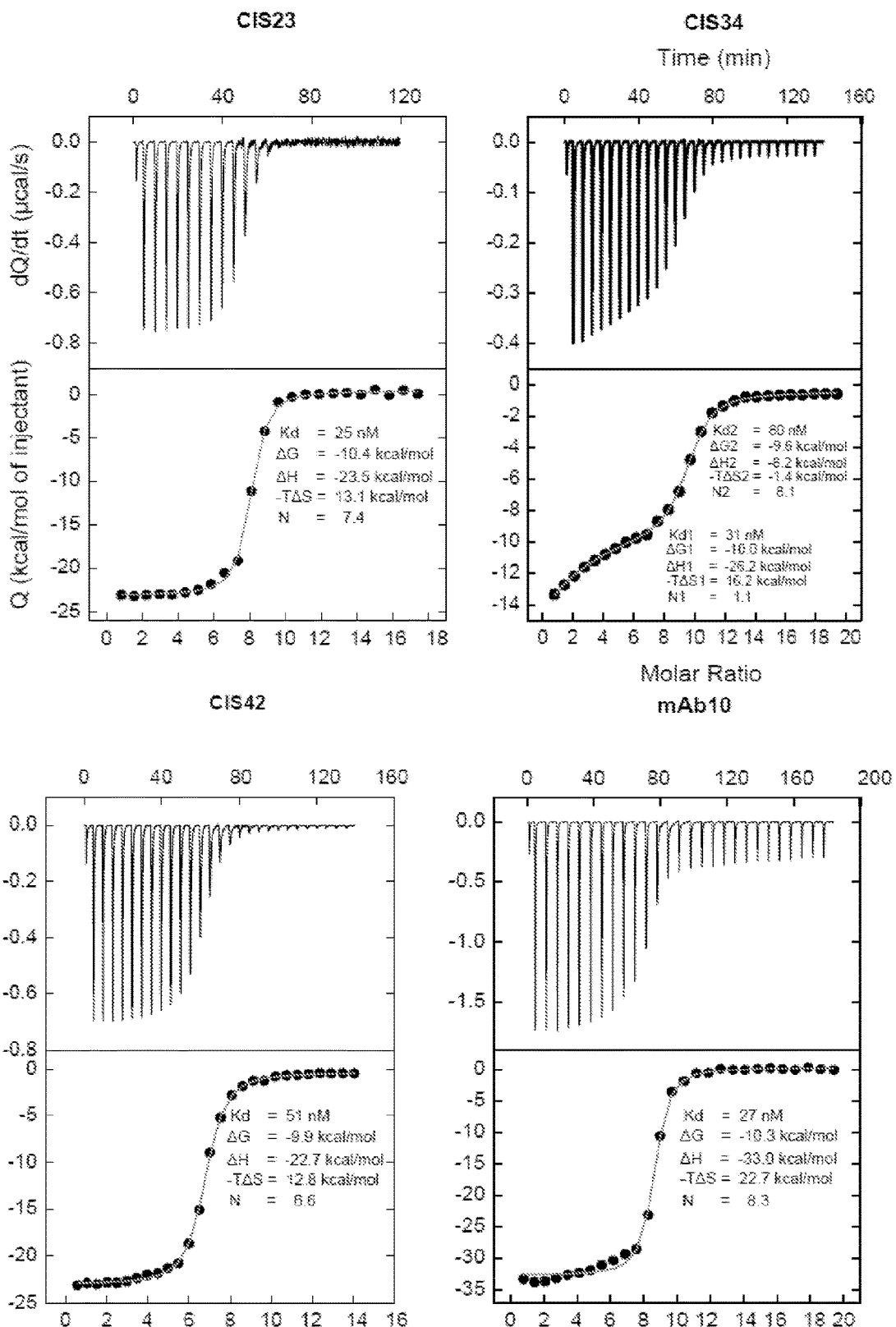
FIGS. 6A-6C. ITC analysis of PfCSP mAbs. Binding of PfCSP mAbs to rPfCSP or peptides.
Figures 6B, 6C:
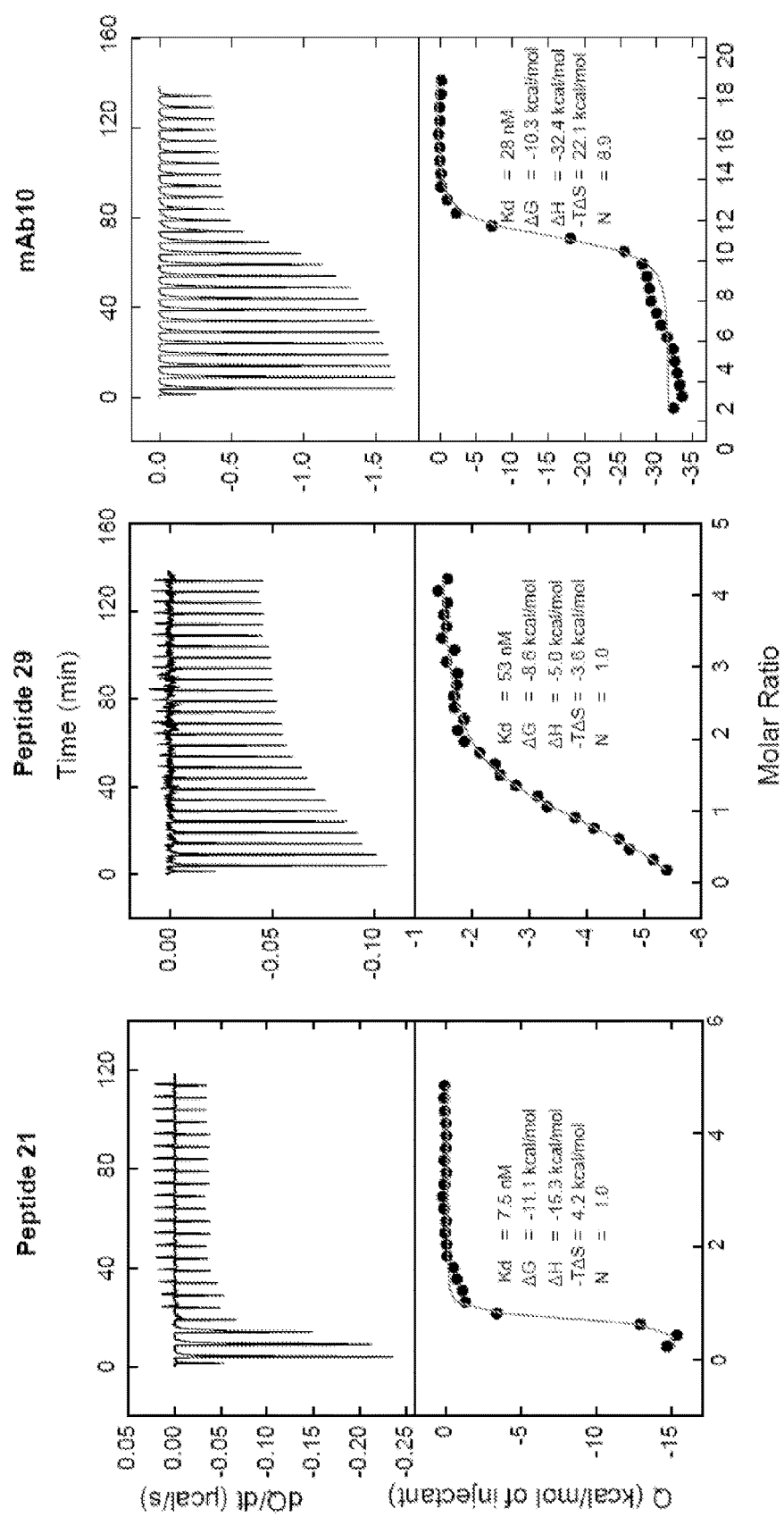
Figure 7D:
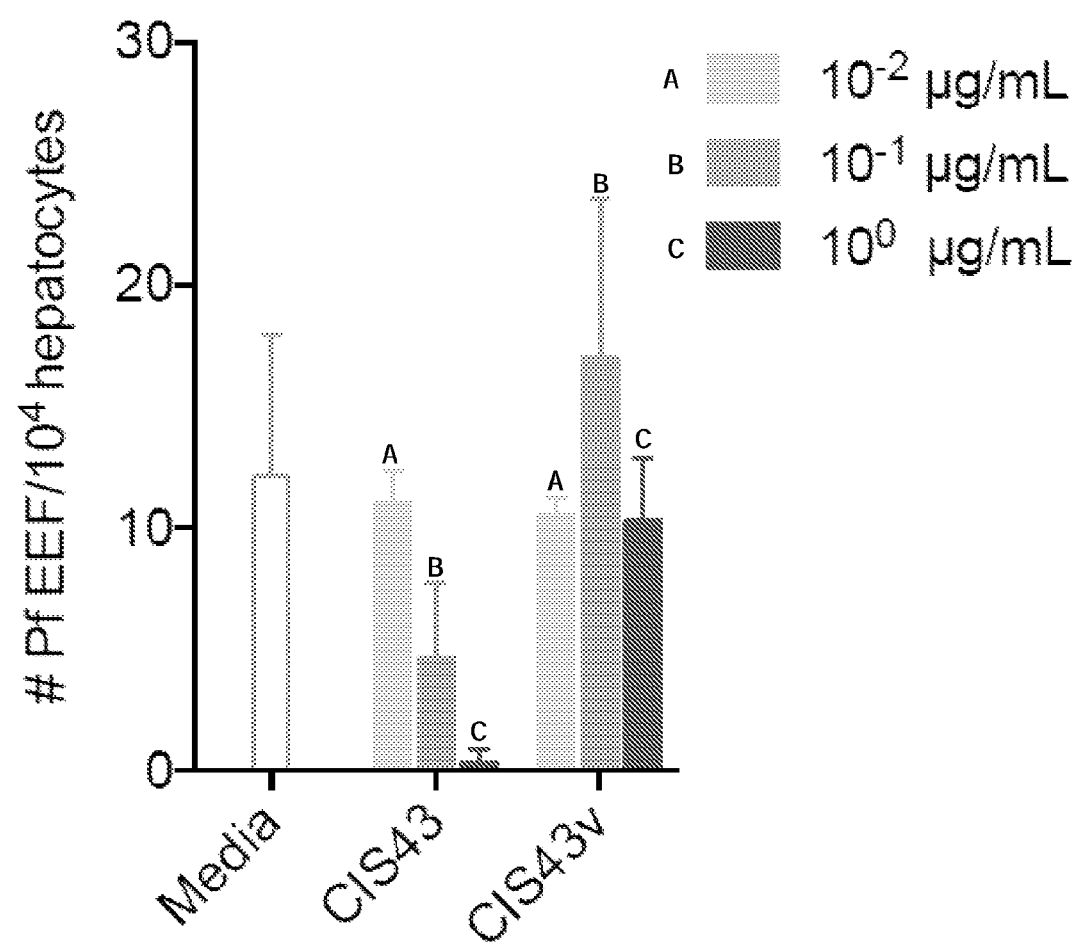

Thermodynamic parameters and stoichiometry of binding of mAbs CIS43, CIS42, CIS23, CIS34 and mAb10 to rPfCSP were then determined by isothermal titration calorimetry (ITC). Remarkably, mAb CIS43 showed two sequential binding events, the first with a single binding site per antibody with an affinity of 7.9 nM, and the second with 5 binding sites with 42 nM affinity (FIG. 3E). Similarly, mAb CIS34 also had two binding events with one site bound at 31 nM, and 8 other sites bound at 80 nM affinity (FIG. 6). In contrast, mAbs CIS23, CIS42 and mAb10, had only one binding event with 6, 7 or ~9 binding sites at 25 nM, 51 nM or 27 nM respectively (FIG. 6), consistent with recent reports using other mouse and human mAbs against the NANP repeat epitopes (Ogen et al., Proc Natl Acad Sci USA, 114, E10438-E10445, 2017; Fisher et al., PLoS Pathog, 13, e1006469, 2017). To further understand the sequential binding event observed for mAb CIS43, ITC analysis of mAb CIS43 with peptide 21, peptide 29 and a mutant of rPfCSP was performed. mAb CIS43 binding to peptides 21 and 29 had affinities of 7.5 nM and 53 nM, respectively (FIG. 6B) which were similar to values obtained with rPfCSP suggesting that the first binding event is to peptide 21. ITC analysis with a mutant PfCSP in which Pro$_{102}$ was changed to Ala and Asp$_{103}$ to Asn, indicated that only one multivalent binding event occurred with a reduced affinity of 140 nM and stoichiometry of 3 binding sites (FIG. 3F). As a control, the binding affinity and stoichiometry of mAb10, which does not bind peptide 21 was not affected with the mutant PfCSP compared to rPfCSP (FIG. 6C). These data confirm that the first high affinity binding event of mAb CIS43 to rPfCSP is to the junctional epitope and suggest such binding may defined previously for the ANPNA peptide (Ghasparian et al., Chem Commun (Camb), 174-176, 2006) was observed in the peptide-antibody bound structures and three β-1 turns could be aligned consecutively to peptide 21. Peptide 21 showed the most contacts with the CIS43 Fab compared to other peptides (FIG. 4D, FIG. 10). To confirm the role of mAb CIS43 residues that mediate binding to peptide 21, variants of this antibody were generated. One variant (Asn56Gly, Thr57Gly, Arg58Gly, Glu61Gly in the heavy chain) (FIG. 7A) abrogated binding to peptide 21 (FIG. 7B). Of note, Arg58$_{HC}$ on mAb CIS43 had been shown to be a key contact residue by structural analysis for binding to peptide 21 (FIG. 4). Moreover, computational free energy calculations revealed Arg58Gly to be the most critical for binding of all four mutations (FIG. 7C). Importantly, this antibody variant had minimal binding to rPfCSP and no functional inhibition of PfSPZ invasion in vitro (FIGS. 7B, 7D).

Figure 8B:
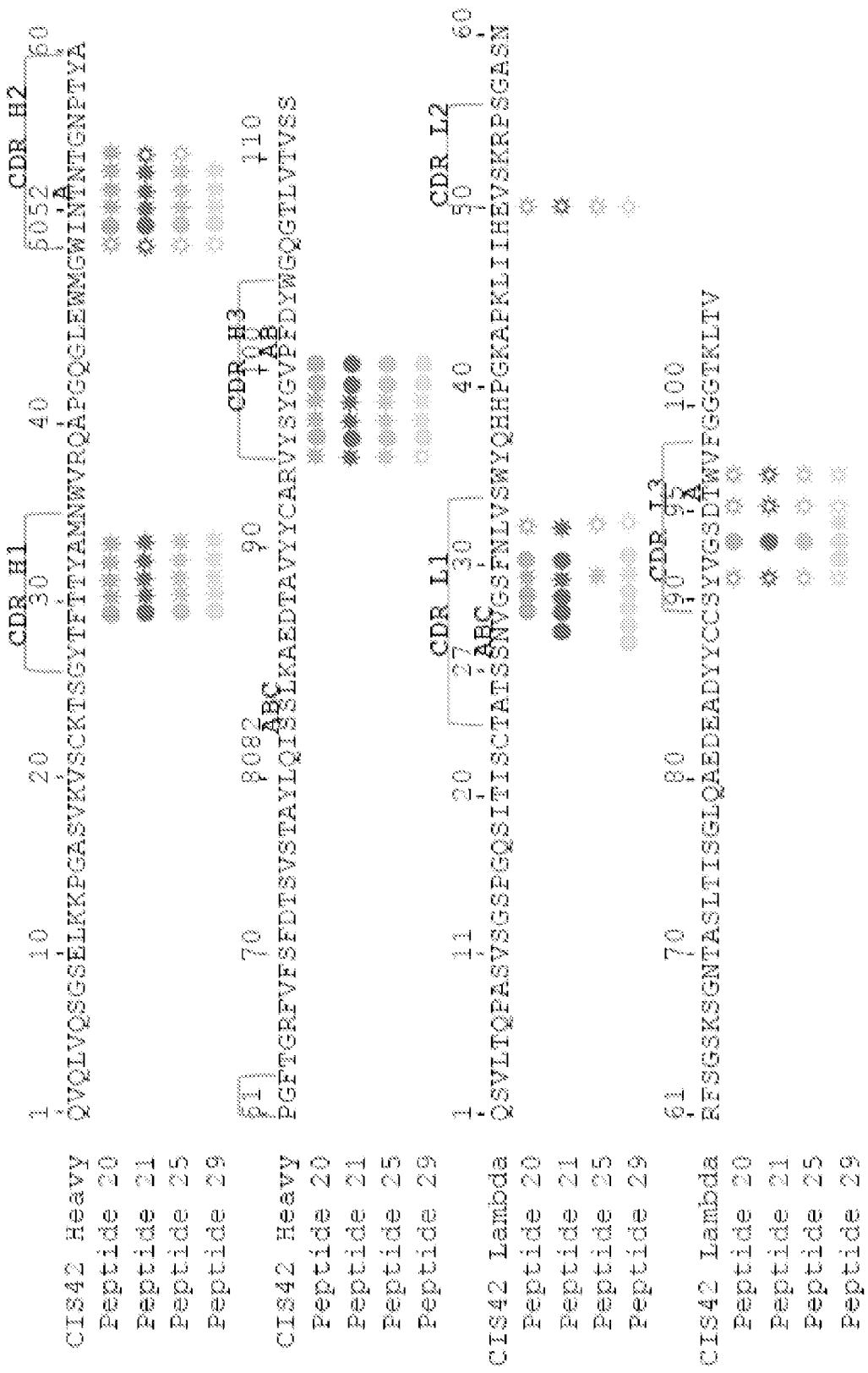
Figure 11A:
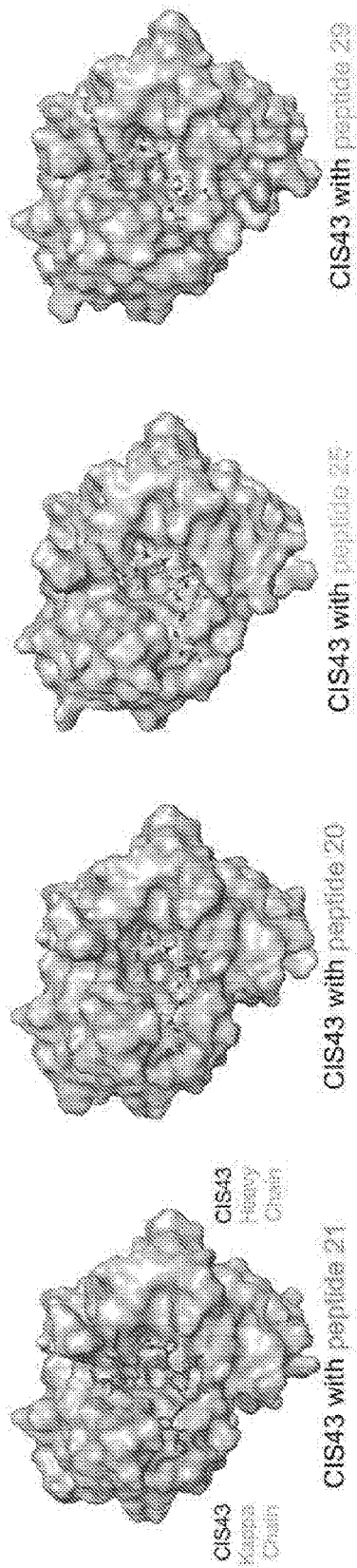
Figure 11B:
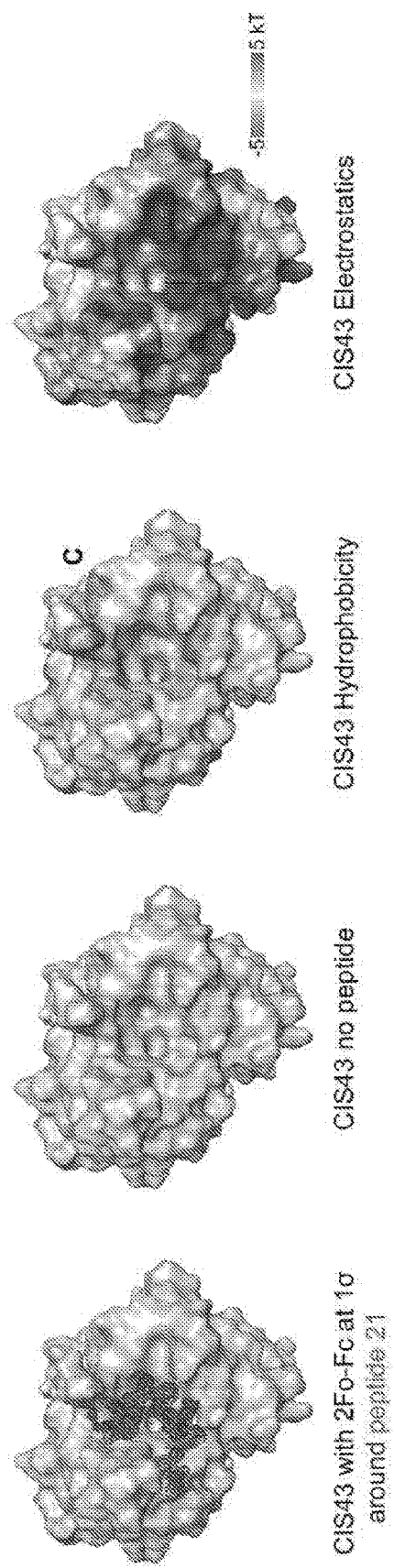
Figure 11D:
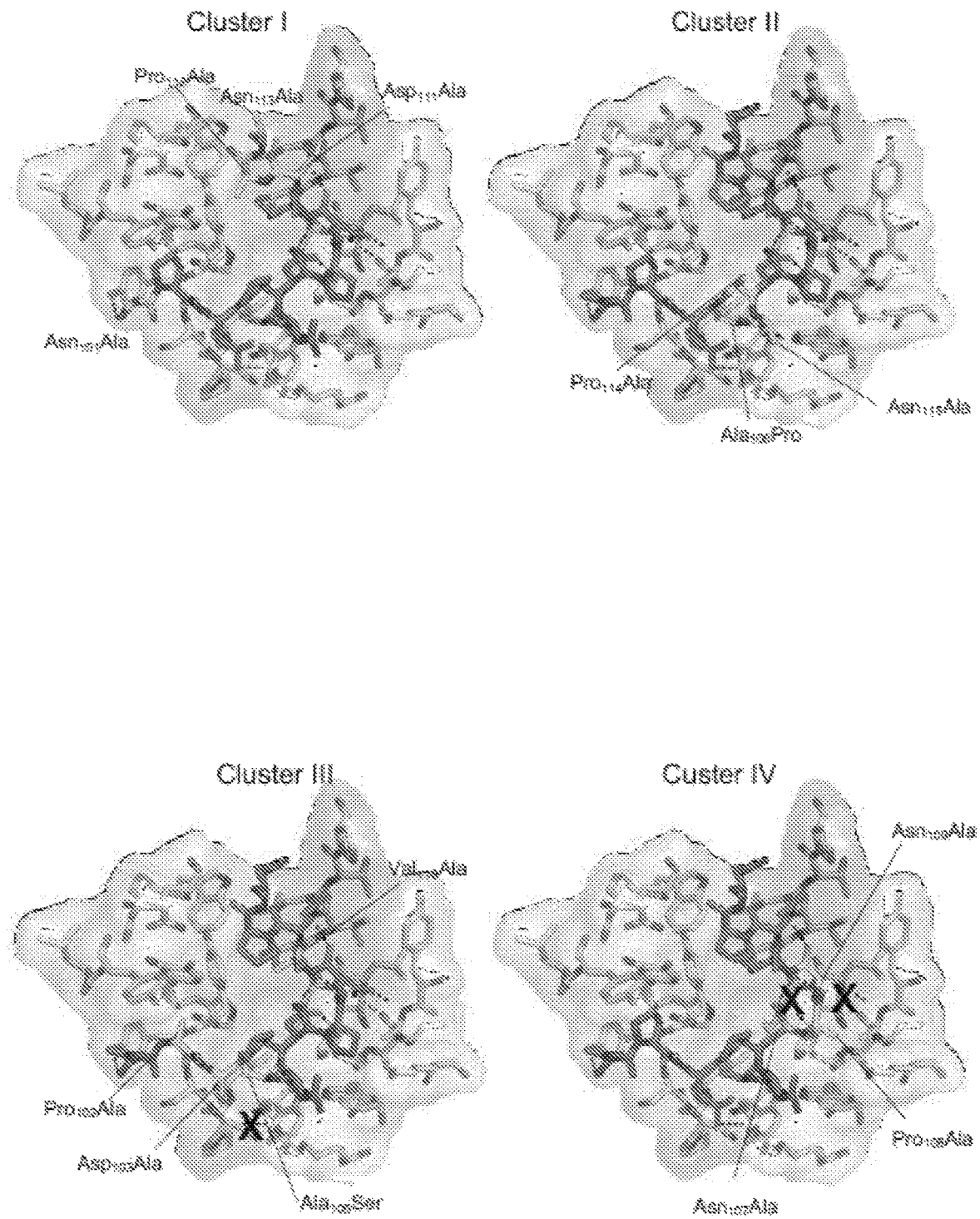

To further understand the relative functional potency of mAb CIS43, the Fab of mAb CIS42, which has limited in vivo function (FIGS. 2A and 2C), was co-crystallized with the same peptides (20, 21, 25 and 29). Crystals were obtained that diffracted X-rays to 2.4 Å, 1.8 Å, 2.0 Å and 2.2 Å, respectively (FIG. 8). The structures show that, unlike with CIS43 Fab, all four peptides adopted an almost identical conformation when bound to CIS42 Fab, with peptide 29 exhibiting the most contacts with CIS42 Fab (FIG. 8). These data are consistent with the peptide competition analysis of mAb CIS42 (FIG. 5C). Additionally, the conformation of peptide 21 differed when bound to CIS42 and CIS43 Fabs as well as the angles of approach of the antibodies. Molecular dynamics (MD) simulations were then used to further analyze the physical movements and stability of mAbs CIS43 and CIS42 bound to peptide 21. After 500 ns, peptide 21 remained buried in the hydrophobic groove of the mAb CIS43 CDR while it detached from its initial binding pocket of mAb CIS42, losing most of its electrostatic interactions and confirming the clear preference of mAb CIS43 for this epitope. Principal component analysis (PCA) of peptide 21 MD simulation showed that mAb CIS43 binds to a rare conformation of peptide 21. Lastly, since this is the first time structures of multiple PfCSP motifs are reported, it was sought to define the PfCSP repeat structure. The analysis showed Ramachandran angles with antibody-bound repeat peptides had similar phi-psi angles every four residues with a few notable outliers. These data substantiated that NPN is the structural repeat that defines PfCSP sequences that contain NANP.

To gain additional insight into the mechanism for how mAb CIS43 mediates protection, a key requirement for sporozoite infection of hepatocytes is the proteolytic cleavage of PfCSP at the putative processing site, RI, which is only 3 amino acids upstream of the junctional epitope. Metabolically labeled PfSPZ were chased in the presence of mAb CIS43, mAb5D5, a known cleavage blocking mAb, and mAb15 which is specific for the C-terminus (FIG. 4) as a negative control. Indeed, mAb CIS43 inhibited cleavage of PfCSP (FIGS. 4C-4D).

Figure 12:
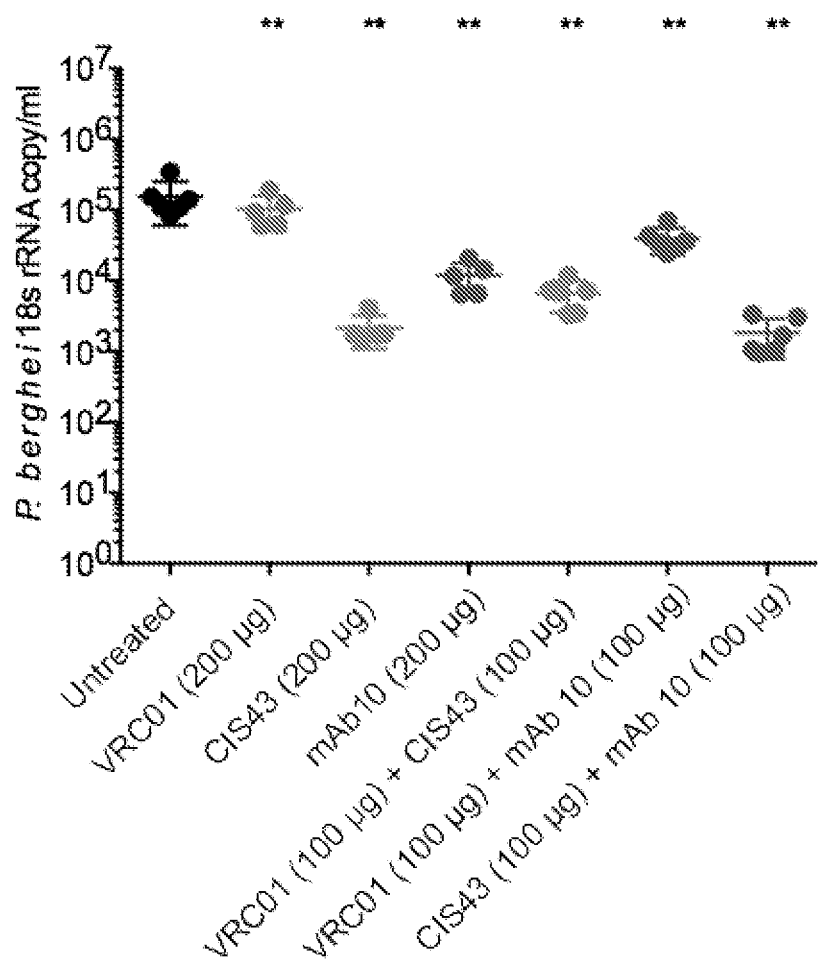
FIG. 12. Following passive transfer of the indicated mAbs, C57BL/6 mice (n=5) were challenged intravenously with 2000 *P. berghei* chimeric sporozoites expressing PfCSP. Liver burden, expressed as Pb 18s rRNA, was determined 40-42 hrs later. VRC01, an HIV mAb was used as an isotype negative control. **p=0.008

Finally, to assess the effect of combining identified mAbs to different regions against PfCSP for inhibiting infection, a protection study using a combination of CIS43 (which binds preferentially to the junctional epitope) and mAb10 (which binds primarily to the repetitive NANP repeats) was performed. Antibodies VRC01, CIS43, mAb10 (alone or in combination) were passively transferred to C57BL/6 mice (n=5), after which the mice were challenged intravenously with 2000 P. berghei chimeric sporozoites expressing PfCSP. Liver burden, expressed as Pb 18s rRNA, was determined 40-42 hrs later. VRC01 is an HIV mAb that was used as an isotype negative control. As shown in FIG. 12, the combination of 100 µg of CIS43 and 100 µg of mAb10 substantially reduced liver burden compared to 100 µg of either antibody in combination with 100 µg of VRC01, or to 200 µg of mAb10. The combination of the two antibodies was roughly equivalent to 200 µg of mAb CIS43 alone. However, by targeting multiple PfCSP epitopes the combination may lead to superior breadth of neutralization relative to use of a sing antibody (which targets a single epitope).

In summary, the human mAb CIS43 directed against a structurally defined junctional epitope confers high-level sterile protection in vivo. Biophysical and structural analyses showing sequential and multivalent, high affinity binding of mAb CIS43 to rPfCSP demonstrates a unique mechanism for neutralization. Moreover, binding of mAb CIS43 at a specific angle and rare conformation of the junctional epitope highlights how the immunodominant NANP sequence, now structurally defined as NPN, may potentially shield the "NPDP" junctional site from recognition and divert the immune response away from this or other sites of vulnerability. Indeed, it is shown that the unique NPDP sequence is critical for the high affinity binding of mAb CIS43 to the junctional epitope and that it may play a role in the overall conformation of rPfCSP for mAbCIS43 binding. A non-limiting explanation for the mechanism of mAb CIS43 mediated protection in vivo is that mAb CIS43 binds PfCSP in the skin and interferes with cleavage of PfCSP to limit invasion of hepatocytes by sporozoites.

For clinical application, the junctional epitope sequence of mAb CIS43 (NPDPNANPNVDPNAN, SEQ ID NO: 62, Peptide 21) occurs only once in PfCSP and is highly conserved amongst thousands of P. falciparum strains recovered globally (See Aurrecoechea et al., PlasmoDB: a functional genomic database for malaria parasites. Nucleic Acids Res 37, D539-543, 2009; and The Pf3K Project: pilot data release 5, malariagen.net/data/pf3k-5, 2016). Indeed, among 6574 analyzed isolates, only 0.12% (8 of 6574) contained a sequence variation in the Peptide 21 epitope. The ability of mAb CIS43 to protect mice in vivo at ~10 µg/ml, an achievable concentration by current human mAb administration, suggests it could be used alone or in combination with other antibodies for passive prevention in humans in which high-level protection would be required for up to 6 months. Such indications would be used by travelers, military personal and elimination campaigns in combination with mass drug administration. Finally, this junctional epitope provides a new site of vulnerability, allowing the design of next-generation subunit vaccines that increase the breadth and potency of humoral immunity to improve protective efficacy against malaria.

Methods:

Data deposition. The structure factors and coordinates of CIS43 and CIS42 bound to peptide 20, 21, 25 and 29 have been deposited in the Protein Data Bank (PDB) with accession codes 6B5L, 6B5M, 6B5N, 6B5O, 6B5P, 6B5R, 6B5S and 6B5T, respectively.

Study subjects and clinical specimens. Sera from protected volunteers in the previously described VRC 312 clinical trial (clinicaltrials.gov; NCT01441167) were screened for Plasmodium falciparum (Pf) circumsporozoite protein (CSP) antibodies and functional capacity for inhibition of sporozoite invasion of hepatocytes in vitro (Hoffman et al., Hum Vaccine, 6, 97-106, 2010; Epstein et al., Science, 334, 475-480, 2011; Seder et al., Science, 341, 1359-1365, 2013; and Ishizuka et al., Nat Med, 22, 614-623, 2016). Briefly, this was a phase 1, open-label, dose-escalation study investigating safety, immunogenicity, and protective efficacy of the radiation-attenuated aseptic, purified, cryopreserved Pf (NF54 strain) sporozoites (PfSPZ) vaccine, SANARIA® PfSPZ Vaccine. Memory B cell PfCSP monoclonal antibodies (mAbs) were isolated from peripheral blood mononuclear cells (PBMCs) taken two weeks after the last dose in a protected donor (VRC312-402) who received 5 doses of $1.35 \times 10^5$ PfSPZ. Plasmablast PfCSP mAbs were isolated from 2 volunteers in the VRC 314 clinical trial (clinicaltrials.gov No. NCT02015091). These subjects received a total of 4 doses of PfSPZ vaccine intravenously at 0, 4, 12 and 20 weeks (first 2 doses at $2.7 \times 10^5$ and 2 doses at $4.5 \times 10^5$). Plasmablasts were isolated from PBMCs, 7 days after the $3^{rd}$ immunization.

PfCSP probes generation. The amino acid sequence of PfCSP of 3D7 (Plasmodb ID PF3D7_0304600.1), a clone of the NF54 strain, was used to generate a codon optimized synthetic gene for expression in mammalian cells (GENSCRIPT®). The DNA construct corresponding to the full length PfCSP, replacing the leader residues 1-20 with a mammalian secretion signal sequence derived from the modified bovine prolactin (MDSKGSSQKGSRLLLLL-VVSNLLLPQGVLA, SEQ ID NO: 118) and excluding the GPI anchor residues 376-397, was cloned into a CMV/R-expression vector along with the C-terminal Avi-tag, HRV3C-processing tag, and the His-purification tag. The resulting construct encodes for the native N-terminal domain, the central domain consisting of $(NANP)_{38}$ tandem repeats with 4 interspersed NVDP, as well as the C-terminal domain PfCSP mutants were generated by site-directed mutagenesis (GENSCRIPT®). Recombinant wild type PfCSP (rPfCSP) or PfCSP mutants were expressed by transient transfection in Expi293 cells (Life Technologies), according to the manufacturer's instructions, and purified from culture supernatants by polyhistidine-tag affinity chromatography (GE Healthcare), followed by gel-filtration. Fractions containing monomers were pooled, concentrated and frozen at −80° C. For tetramer probe generation, peptides/proteins were first biotinylated and then conjugated to fluorophore. rPfCSP was biotinylated using ligase Bir A (Avidity) at 30° C. for 4 h and buffer exchanged with PBS (pH 7.4) over a 30-kDa Centricon plus filter (Millipore) to remove excess free biotin. The repeat peptide $(NANP)_9$ (SEQ ID NO: 79) was synthetically made and N-terminally biotinylated through the lysine analog Ahx linker (GENSCRIPT®). Biotinylated rPfCSP and $(NANP)_9$ (SEQ ID NO: 79) peptide were fluorescently labeled by sequential addition of streptavidin conjugated to allophycocyanin (SA-APC) or phycoerythrin (SA-PE) (Life Technologies) in a 4:1 molar ratio.

Isolation of PfCSP-specific memory B cells. PBMCs ($10^6$) were stained for viability using the amine-reactive dye Aqua LIVE/DEAD (Invitrogen) followed by staining for surface markers. In addition to the tetramer probes rPfCSP-APC, $(NANP)_9$-PE (SEQ ID NO: 79-PE) generated above, the staining panels included: anti-CD3-BV510 (BIOLEGEND®), CD8-BV510 (BIOLEGEND®), CD14-BV510 (BIOLEGEND®), CD56-BV510 (BIOLEGEND®), CD19-ECD (Beckman), CD27-QD605 (Invitrogen), CD21-Cy5PE (Becton Dickenson), CD38-Alexa Fluor 680 (Becton Dickenson), IgD-Cy7PE (Becton Dickenson), IgM-Cy5.5-PerCP (Becton Dickenson), and IgG-Cy7PE (Becton Dickenson). Cells were acquired and sorted using a BD FACS Aria II instrument (BD Immunocytometry Systems), and fluorescence-activated cell sorting (FACS) data was analyzed using FlowJo software (Tree Star). Gating strategy is shown in FIG. 1. PfCSP-reactive (rPfCSP$^+$ and/or $(NANP)_9^+$ (SEQ ID NO: 79) CD19$^+$CD27$^+$IgG$^+$IgD$^-$IgM$^-$ memory B cells were single cell, dry-sorted into 96-well PCR plates, rapidly frozen on dry ice and stored at −80° C. until processing.

Production of recombinant immunoglobulins (IgG). Following single rPfCSP-specific memory B cell sort, lysis buffer was added to the plate, and the variable region of the heavy and light chains of the IgG genes were amplified by RT-PCR and re-expressed as described previously (Tiller et al., J Immunol Methods, 329, 112-124, 2008). Briefly, amplification of rearranged IgG VH and Vκ or Vλ genes was performed using a cocktail of primers followed by sequencing and cloning into expression vectors containing the relevant constant region. Matched heavy and light chain constructs derived from each sorted cell were coexpressed using Expi293 cells, and 28 full-length IgG were purified using a recombinant protein-A column (GE Healthcare). Sequence analysis was performed using IMGT (igmt.org).

Isolation of plasmablasts. PBMCs were freshly isolated from blood samples collected 7 days after PfSPZ immunization and stained for viability with Aqua Live/Dead dye (Invitrogen) followed by surface-staining for the following markers: CD20-Cy7APC (BD Bioscience), CD19-FITC (BD Bioscience), CD3-Cy7PE (BD Bioscience), CD38-PE (BD Bioscience), and CD27-APC (ThermoFisher). Plasmablasts were gated as live, CD3−CD20−CD19+ CD27+CD38+ and were sorted as single cells into 96-well PCR plates containing 20 μl/well of RT reaction buffer that included 5 μl of 5× First strand cDNA buffer, 0.5 μl of RNAseOut (Invitrogen), 1.25 μl of DTT, 0.0625 μl of Igepal and 13.25 μl of dH2O (Invitrogen) as previously described (Liao et al., J Virol Methods, 158, 171-179, 2009).

Antibody production from plasmablasts. Immunoglobulin genes were amplified by RT and nested PCR without cloning from RNA of single sorted cells as previously described (Liao et al., J Virol Methods, 158, 171-179, 2009; Bonsignori et al., J Virol 85, 9998-10009, 2011). Isolated Ig V(D)J gene pairs were assembled by PCR into linear full-length Ig heavy- and light-chain gene expression cassettes as previously described (Liao et al., J Virol Methods, 158, 171-179, 2009; Bonsignori et al., J Virol 85, 9998-10009, 2011). Heavy and light chain linear cassettes were co-transfected in 293T cells using Effectene with enhancer (Qiagen). Transfected cultures were incubated at 37° C. 5% $CO_2$ for 3 days. Supernatants were harvested, concentrated and purified using HiTrap Protein A pre-packed high performance plates (GE Healthcare) for 20 min at RT on a shaker. Following PBS/NaCl wash, eluates were neutralized with trizma hydrochloride and buffer exchanged with PBS before determining antibody concentration by Nanodrop.

ELISA. MaxiSorp ELISA plates (Thermo Scientific Nunc) were coated with 100 μL of rPfCSP (1 μg/ml) per well for one hour at room temperature (RT) according to the manufacturer instructions (KPL). Coated plates were blocked with 100 μl of 1× blocking solution for one hour at RT, followed by incubation with 100 μl of PfCSP mAbs or controls at varying concentrations (0.00006-5.0 μg/ml). After one hour, plates were incubated with 100 μl/well of 1.0 μg/ml peroxidase-labeled goat anti-human IgG antibody. Plates were washed six times with PBS-Tween between each step. After a final wash, samples were incubated for about 15 min with the ABTS peroxidase substrate. The optical density was read at 450 nm after addition of stopping solution (100 μl/well).

For the PfSPZ ELISA, serially diluted (0.06-1.0 μg/ml) PfCSP mAbs or controls were added to the PfSPZ-coated plates and incubated for one hour and binding was assessed in a similar manner as for the rPfCSP ELISA described above. The mouse mAb2A10 (Nardin et al., J Exp Med, 156, 20-30, 1982; Zavala et al., J Immunol, 134, 1202-1205, 1985), which is specific for the NANP repeat region of PfCSP was used as a positive control and VRC01, a human anti-HIV-1 IgG1, as an isotype matched negative control. To determine the inhibitory effect of PfCSP peptides on binding of mAb CIS43 to PfSPZ, MaxiSorp ELISA plates (Thermo Scientific NUNC-IMMUNO™) pre-coated with $5 \times 10^3$ PfSPZ were blocked with PBS-BSA (2% BSA-SIGMA) for one hour at RT and washed with PBS prior to adding mAb CIS 43 (10 ng/ml), preincubated overnight with varying concentrations (0-1000 μg/ml) of the PfCSP peptides. ELISA was performed as described above.

Epitope mapping of PfCSP mAbs. Mapping of the PfCSP mAb epitopes was performed as previously described (Douglas et al., J Immunol, 192, 245-258, 2014) using linear PfCSP 15-mer peptides (GENSCRIPT®) overlapping by 11 residues spanning the full length of PfCSP. MaxiSorp ELISA plates (Thermo Scientific Nunc) were coated with 100 μl of peptides (10 μg/ml). Following overnight incubation, plates were blocked with PBS+0.05% Tween-20 and 1% BSA (Sigma-Aldrich) for one hour. Plates were incubated with 100 μl of PfCSP mAbs or controls at varying concentrations (0.00006-5.0 μg/mL). After one hour, plates were incubated with 100 μl/well of peroxidase-labeled goat anti-human or goat anti-mouse (IgG H+L) secondary antibody (Thermo Fisher Scientific) at 1:20,000 dilution in PBST-1% BSA. All the incubation steps were done at RT. Plates were washed six times with PBS-Tween between each step. After a final wash, samples were incubated for about 15 min with the TMB Plus Reagent (Thermo Fisher Scientific) according to the manufacturer's instructions. The optical density was read at 450 nm after addition of stopping solution (100 µl/well).

Competitive ELISA was performed as previously reported (Espinosa et al., *J Infect Dis*, 212, 1111-1119, 2015) using selected peptides. Briefly, ELISA plates were coated with 100 µL of rPfCSP (200 ng/ml) overnight. After blocking plates with PBS-1% BSA for one hour, PfCSP mAbs (10 ng/ml), preincubated overnight with varying concentrations (0-1000 µg/ml) of selected PfCSP peptides in PBS-1% BSA, were added to the rPfCSP-coated plates and ELISA proceeded as described above. For the alanine scanning mutagenesis experiments, competitive ELISA was performed as described above using peptide 21 variants (GENSCRIPT®).

Indirect fluorescence assay (IFA). Freshly isolated PfSPZ ($3 \times 10^3$) were air-dried on poly-L-lysine-coverslips (Tekdon Inc.) and incubated for half an hour at RT with varying concentrations (0.0002-1.0 µg/ml) of PfCSP mAbs or controls. After washing with PBS-1% BSA, slides were incubated with FITC-labeled goat anti-Human IgG (Fcγ) and green-fluorescent sporozoites were visualized using an upright Nikon Eclipse 90i fluorescence microscope.

Kinetic binding assay by biolayer interferometry. Antibody binding kinetics were measured using biolayer interferometry on an Octet Red384 instrument (FORTÉBIO®) using streptavidin capture biosensors (FORTÉBIO®). PfCSP mAb solutions were plated in solid black tilt-well 96-well plates (Geiger Bio-One); assays were performed with agitation at 30° C. Loading of biotinylated rPfCSP or peptides 21 and 29 was performed for 300s, followed by a 60s baseline in buffer (PBS+1% BSA). Association with whole IgG (serially diluted from 267 to 33 µM) was done for 300s, followed by a dissociation step in buffer for 600s. Background subtraction of non-specific binding was performed by measuring association in buffer alone. Data analysis and curve fitting were performed using Octet software, version 7.0. Experimental data were fitted with the binding equations describing a 1:1 heterologous ligand interaction. Global analyses of the complete data sets, assuming binding was reversible (full dissociation), were carried out using nonlinear least-squares fitting allowing a single set of binding parameters to be obtained simultaneously for all concentrations of a given mAb dilution series.

In vitro functional inhibition assay of PfSPZ invasion of hepatocytes. Micropatterned co-culture (MPCC) preparation and Pf infection were carried out as described previously (March et al., *Cell Host Microbe*, 14, 104-115, 2013; March et al., *Nat Protoc*, 10, 2027-2053, 2015). Briefly, glass-bottom 96-well plates were coated homogenously with rat tail type I collagen (50 µg/ml) and subjected to soft-lithographic techniques to pattern the collagen into microdomains of 500 µm islands that mediate selective hepatocyte adhesion. To create MPCCs, cryopreserved primary human hepatocytes (BioreclamationIVT) were pelleted by centrifugation at 100 g for 6 min at 4° C., assessed for viability using trypan blue exclusion (typically, 70 to 90% excluded the dye), and seeded on collagen-micropatterned plates. Each well contained approximately 10,000 hepatocytes organized in colonies of 500 µm in serum-free DMEM with 1% PenStrep. Two to three hours later, cells were washed with serum-free DMEM-1% PenStrep, and the medium was switched to human hepatocyte culture medium. One day after seeding, PfCSP mAbs were added, in triplicate, at four concentrations (10, 1.0, 0.1 and 0.01 µg/ml) to the MPCCs, 30-45 minutes prior to infection with $7.5 \times 10^4$ fresh PfSPZ per well. After 3 hours, cultures were washed with hepatocyte culture medium with 3% PenStrep and 0.1% Fungizone, and 7,000 3T3-J2 fibroblasts were added to create the co-culture. Medium was replaced daily. Samples were fixed on day 3.5 post infection. The impact of the antibodies on hepatocyte infection was assessed by calculating the number of liver-stage parasites or exoerythrocytic forms (EEFs) present at day 3.5 of infection. EEFs were determined by staining for PfHSP70 and visualized with a Nikon Eclipse Ti fluorescence microscope.

In vivo protection in C57BL/6 mice with chimeric Pb-PfCSP SPZ. For intravenous (IV) challenge, 6-8 week old C57BL/6 mice (5/group) were IV injected with controls or varying concentrations of PfCSP mAbs diluted in PBS (pH 7.4) in a total volume of 200 µL per mouse, and immediately challenged with 2000 *P. berghei* chimeric SPZ expressing PfCSP (Pb-PfCSP SPZ). Forty hours later, livers were harvested and RNA was isolated to quantify the Pb-specific 18s rRNA levels by quantitative real-time PCR (RT-qPCR).

For mosquito bite challenge, *Anopheles stephensi* female mosquitoes were allowed to feed on 8 weeks old Swiss webster infected mice with blood stages Pb-PfCSP. Eighteen days after blood feeding on infected mice, the proportion of infected mosquitoes was 9 out of 12 (75%) as determined by salivary gland dissection. Based on this calculation, 6-7 mosquitoes were needed to challenge mice with the equivalent of ~5 infected mosquitoes. Mice (up to 7 per group) were intravenously injected with PfCSP mAbs (300 µg/mAb) as described above. Ten minutes later, mice were anesthetized with 2% Avertin (Alfa Aesar) and mosquitoes were allowed to feed on mice for ~10 minutes, after which mosquito abdomens were visually inspected for positive blood meal. Mouse parasitemia was assessed daily by Giemsa staining of blood smears from day 4 through day 12 post-infection.

In vivo protection in FRG-huHep mice. Passive transfer of controls and PfCSP mAbs, and infectious challenge in human hepatocyte donor-matched (FRG-huHep) mice was done as previously described (Sack et al., *Infect Immun*, 82, 808-817, 2014). Briefly, FRG-huHep mice, purchased from Yecuris, Inc, were given 30-150 µg of PfCSP mAbs or controls intraperitoneally (IP) 16-24 hours prior to infection. Fifty *Anopheles* mosquitos infected with Pf expressing GFP-luciferase were allowed to feed for ten minutes on FRG-huHep mice. Six days post challenge, mice were imaged following IP-administration of 100 µl of Rediject D-luciferin (Perkin Elmer) using bioluminescence and IVIS imaging to determine the parasite liver burden as previously described (Sack et al., *Infect Immun*, 82, 808-817, 2014; Miller et al., *PLoS One* 8, e60820, 2013). Total flux (pixels/second) was measured after choosing an equivalent region of interest around each mouse liver. Parasite liver burden was normalized using the average of the negative control group that received the isotype species-matched IgG.

For sterile protection, FRG-huHep mice were IP-injected with controls or PfCSP mAb (50 µg/mouse) as described above. The following day, mice were challenged by the bite of 5 Pf-infected mosquitoes/mouse by aliquoting 5 infected mosquitos per mouse into a single cage based on mosquito midgut oocyst infection quantification. At approximately day 6.5, all mice were injected with 400 µl of packed human red blood cells at 70% hematocrit in RPMI. On day 7 and day 9, mice were bled via the retroorbital plexus and 50 µl was mixed into 1 ml of NucliSens EasyMag buffer (BioMerieux) and placed at −80° C. until extraction. Total RNA extraction and qPCR for number of Pf 18s rRNA copies was performed as previously published (Murphy et al., *Am J*

Trop Med Hyg, 86, 383-394, 2012) Animals were considered positive if any parasite RNA above background was detected in blood.

ELISA quantitation of mAb serum concentration. To assess circulating levels of passively transferred PfCSP mAbs, FRG-huHep mice were bled via the retroorbital plexus immediately prior to infectious mosquito bite challenge. ELISA was performed from serum as previously described using of rPfCSP-coated plates (2 µg/ml). A standard curve for each mAb was generated by applying 8 two-fold dilutions of mAb in dilution/blocking buffer starting at 625 ng/ml. Serum samples were applied at a 1:160 and 1:320 dilution in dilution/blocking buffer. The average of the 1:160 and 1:320 calculated concentration values was used for each individual sample.

Fab expression and purification. Antibodies heavy and light chains were cotransfected into GnTI-cells (ATCC). Six days following transfection, supernatant was harvested and antibodies were purified over protein A resin column, washed with 5 column volumes of PBS, and eluted with IgG Elution buffer (Pierce). Tris (1M) was added immediately to neutralize the pH to ~7.4. IgGs were then digested with Lys C overnight at 37° C. (1 µg for 10 mg of IgG) and the antigen-binding fragments (Fab) was purified further by collecting the flow through of Protein A column and by size exclusion chromatography in 5 mM Hepes, 150 mM NaCl. For Fab-peptide preparations, peptides were dissolved in DMSO and added to the Fabs at a 50% molar excess.

Isothermal titration calorimetry (ITC). ITC was carried out using VP-ITC microcalorimeters from MicroCal/Malvern Instruments. In all titration experiments, rPfCSP, PfCSP mutants and PfCSP mAbs (whole IgG or Fab) were prepared in PBS, pH 7.4. Each antibody solution, prepared at a concentration of ~100 µM (expressed per site or Fab fragment), was injected in 10 µl aliquots into the calorimetric cell containing rPfCSP at a concentration of ~1 µM. Peptides 21 or 29 and mAb CIS43 were prepared in PBS, pH 7.4, with 2% DMSO. mAb CIS43 solution, prepared at a concentration of 50 µM (expressed per Fab site), was injected in 10 µl aliquots into the calorimetric cell containing the peptide at a concentration of 2 µM. All titrations were performed at 25° C. The exact concentrations of the reactants in each experiment were determined from the absorbance at 280 nm. The heat evolved upon each injection of antibody was obtained from the integral of the calorimetric signal. The heat associated with binding to rPfCSP or the peptide in the cell was obtained by subtracting the heat of dilution from the heat of reaction. The individual heats were plotted against the molar ratio, and the enthalpy change, $\Delta H$, the association constant, $K_a$ (the dissocation constant, $K_d = 1/K_a$) and the stoichiometry, N, were obtained by nonlinear regression of the data to a model that takes into account the binding to two sets of sites with different binding energetics for rPfCSP or to a single-binding-site model for the peptides. Gibbs energy, $\Delta G$, was calculated from the relation $\Delta G = -RT\ln K_a$, where R is the is the universal gas constant, (1.987 cal/(K×mol)) and T the absolute temperature in kelvin. The entropy contribution to Gibbs energy, $-T\Delta S$, was calculated from the known relation $\Delta G = \Delta H - T\Delta S$.

Crystallization and data collection. Crystals of CIS43 Fab with peptide 20, 21, 25 and 29, respectively, were obtained using a mosquito and NT8 dispensing robots and screening was done with Rigaku Wizard Precipitant Synergy block #2, Molecular Dimensions Proplex screen HT-96, Hampton Research Crystal Screen HT by the vapor diffusion method. Crystals used for diffraction data were grown in the following conditions; CIS43 Fab with peptide 20: 0.2M Ammonium Sulfate, 0.1M Sodium Acetate Trihydrate pH 4.6, 30% PEG MME 2000; CIS43 Fab with peptide 21: 0.1M Sodium Acetate Trihydrate pH 4.6, 2M Ammonium Sulfate; CIS43 Fab with peptide 25: 0.1M Sodium Hepes pH 7.5, 1.4M Sodium Citrate Tribasic Dihydrate; CIS43 Fab with peptide 29: 1.6M Sodium Citrate Tribasic Dihydrate pH 6.5, using the vapor diffusion method. Crystals were cryo-protected in solutions containing 30% molar excess of their original reagents and 20% Ethylene Glycol. Crystal diffracted to 2.4 angstroms (Å), 1.8 Å, 2.0 Å and 2.2 Å, respectively.

Crystals of CIS42 Fab with peptide 20, 21, 25 and 29 were obtained following the same procedure described above. Crystals used for diffraction data were all grown in 15% PEG3350, 9% Isopropanol, 0.12M Ammonium Citrate pH 8.5. Crystals were cryo-protected in solutions containing 30% molar excess of their original reagents and 20% Ethylene Glycol. Crystals of CIS42 Fab with peptide 20, peptide 21, peptide 25 and peptide 29 diffracted to 2.3 Å, 1.8 Å, 2.0 Å and 2.2 Å, respectively. Data were collected at ALS 5.1 and 5.2 on the Fred Hutchinson Cancer Research Center home source (Rigaku) and processed using HKL2000.

Structure solution and refinement. The structures of CIS43 Fab and CIS42 Fab with peptides were solved by molecular replacement using Phaser in CCP4 (Collaborative Computational Project, N. The CCP4 suite: programs for protein crystallography. *Acta Crystallogr D Biol Crystallogr* 50, 760-763 (1994). The peptides were manually fitted using COOT (Emsley & Cowtan, *Acta Crystallogr D Biol Crystallogr*, 60, 2126-2132, 2004) and refinement of the structures was done in Phenix (Adams et al., *Acta Crystallogr D Biol Crystallogr*, 66, 213-221, 2010). Structural figures were made with Pymol.

Molecular dynamic simulations. Four protein systems were created based on the crystal structures: CIS43 Fab in complex with peptide 21, CIS42 Fab in complex with peptide 21, free peptide 21 in CIS43 Fab-bound conformation, and free peptide 21 in CIS42 Fab-bound conformation. All protein models were immersed in a water box neutralized to 0.15M with sodium chloride ions. The water box was built using VMD's Solvate plugin and the ions were added with VMD's Autoionize plugin (Visual Molecular Dynamics) (Humphrey et al., *J Mol Graph*, 14, 33-38, 27-38, 1996). Protein structure files were created using VMD's psfgen function.

The four protein systems were then configured to run with NAMD2.12 (Scalable Molecular Dynamics) (Phillips et al., *J Comput Chem*, 26, 1781-1802, 2005) with the CHARMM36 force field (Huang et al., *Nat Protoc*, 8, 1907-1915, 2013). TIP3P water parameterization was used to describe the water molecules. All systems were fully minimized with 20,000 conjugate gradient steps before proceeding with equilibration runs. Equilibration began with a slow heating starting at 100 K until reaching a final temperature of 310 K. Simulations were performed with a 1 fs timestep for all equilibration and production runs. The periodic electrostatic interactions were computed using particle-mesh Ewald (PME) summation with a grid spacing smaller than 1 Å. Constant temperature was imposed by using Langevin dynamics with a damping coefficient of 1.0 ps. Constant pressure of 1 atm was maintained with Langevin piston dynamics, a 200 fs decay period and a 50 fs time constant. 500 ns of molecular dynamics simulation was achieved for all four protein systems on the NIH High-Performance Computing Cluster (hpc.nih.gov).

Peptide 21 was assessed with root mean square deviation (RMSD) and root mean square fluctuation (RMSF). RMSD was calculated using VMD's Trajectory Tool plugin, while RMSF was calculated with Gromacs (Páll et al., Tackling Exascale Software Challenges in Molecular Dynamics Simulations with GROMACS. 8759, 3-27, 2015). Both were calculated in angstroms over the full 500 ns trajectory and were compared side-by-side. For RMSD and RMSF, the antibodies were aligned to frame 1 of the respective trajectories in order to compare conformation changes and movement of peptide 21. Additionally, principal component analysis (PCA) was performed using mdtraj, scikit, and graphed with matplotlib to visualize the distribution of structural conformations of free peptide 21. Peptide 21 in its conformations bound to CIS43 Fab and CIS42 Fab were plotted on the PCA density heatmap. Eigenvalues are listed to show principal component 1 and principal component 2 as the dominant components. Hydrogen bond analysis was performed with UCSF Chimera on peptide 21 for both the CIS43 Fab and CIS42 Fab simulations and number of hydrogen bonds are shown over the 500 ns trajectory. Lastly, the crystal structures of CIS43 Fab and CIS42 Fab were aligned to their 500 ns frames and RMSD was calculated to compare movement and flexibility of the antibody CDR loops. Free energy calculations of the CIS43 variant mutations were performed computationally using FoldX. CIS43 Fab bound to peptide 21 was used as input. The protein structure was first repaired, then mutated, then analyzed for interaction binding energy between the mutants and wild-type.

Pulse-Chase Metabolic Labeling Assay. Pulse-chase metabolic labeling of *Plasmodium* sporozoites has been previously described (Coppi et al., *J Exp Med*, 201, 27-33, 2005; Espinosa et al., *J Infect Dis*, 212, 1111-1119, 2015). Briefly, freshly dissected *P. falciparum* sporozoites were incubated in Dulbecco's modified Eagle's medium (DMEM) without Cys/Met, 1% BSA and 400 µCi/mL L-[35S]-Cys/Met for 45 min at 28° C. and then kept on ice or chased at 28° C. for 1.5 hours in DMEM with Cys/Met and 1% BSA in the absence or presence of the indicated concentrations of antibodies: mAb15 (isotype control human mAb specific for PfCSP C terminus), mAb5D5 (positive control mouse mAb specific for PfCSP N terminus), and mAb CIS43. Following the lysis of chased sporozoites, labeled PfCSP was immunoprecipitated with mAb2A10 (mouse mAb specific for PfCSP repeats) conjugated to sepharose. Labeled PfCSP was eluted from the beads and analyzed by sodium dodecyl sulfate polyacrylamide gel electrophoresis (SDS-PAGE) and autoradiography. Densitometry of the high and low molecular weight bands was performed using Image J software. The ratio of the density, or area under the curve, of the top band to the bottom band was calculated.

Statistics. For liver parasite burden in C57BL/6 mice, data were compared for significance using a Mann-Whitney test, whereas in FRG-huHep mice the Kruskal-Wallis test, with Dunn's correction for multiple comparisons, was used. Kaplan-Meier parasitemia curves were analyzed by the log rank test. For measurement of PfCSP mAbs in mouse serum, standard curves were fitted with a hyperbolic parameter curve and concentration values were interpolated. For the stoichiometry data, errors with 95% confidence were estimated from the fits of the data. Unless otherwise indicated, all data were plotted and graphed using GraphPad Prism 7.0. p value<0.05 indicated statistically significant differences.

It will be apparent that the precise details of the embodiments described may be varied or modified without departing from the spirit of the described embodiments. We claim all such modifications and variations that fall within the scope and spirit of the claims below.

It is claimed:

1. An isolated monoclonal antibody, comprising:
a heavy chain variable region (V$_H$) comprising a heavy chain complementarity determining region (HCDR)1, a HCDR2, and a HCDR3 comprising the amino acid sequences set forth as SEQ ID NOs: 15, 45, 17, respectively, and a light chain variable region (V$_L$) comprising a light chain complementarity determining region (LCDR)1, a LCDR2, and a LCDR3 comprising the amino acid sequences set forth as SEQ ID NOs: 18, 46, and 20, respectively.

2. The isolated monoclonal antibody of claim 1, wherein the V$_H$ and the V$_L$ comprise amino acid sequences at least 90% identical to the amino acid sequences set forth as:

SEQ ID NOs: 11 and 12, respectively.

3. The isolated monoclonal antibody of claim 1, comprising human framework regions.

4. The isolated monoclonal antibody of claim 1, wherein the $V_H$ and the $V_L$ comprise the amino acid sequences set forth as SEQ ID NOs: 11 and 12, respectively.

5. The isolated monoclonal antibody of claim 1, wherein the antibody comprises a human constant domain.

6. The isolated monoclonal antibody of claim 1, wherein the antibody is a human antibody.

7. The isolated monoclonal antibody of claim 1, wherein the antibody is an IgG.

8. The isolated monoclonal antibody of claim 7, comprising heavy and light chains comprising the amino acid sequences set forth as SEQ ID NOs: 13 and 14, respectively.

9. The isolated monoclonal antibody of claim 1, comprising a recombinant constant domain comprising a modification that increases the half-life of the antibody.

10. The isolated monoclonal antibody of claim 9, wherein the modification increases binding to the neonatal Fc receptor.

11. The isolated monoclonal antibody of claim 10, wherein the recombinant constant domain is an IgG1 constant domain comprising M428L and N434S mutations.

12. An isolated antigen binding fragment of the isolated monoclonal antibody of claim 1, wherein the antigen binding fragment comprises the $V_H$ and the $V_H$ of the monoclonal antibody.

13. The antigen binding fragment of claim 12, wherein the antigen binding fragment is a Fv, Fab, F(ab')$_2$, scFV or a scFV$_2$ fragment.

14. The isolated monoclonal antibody of claim 1 conjugated to an effector molecule or a detectable marker.

15. A composition comprising an effective amount of the isolated monoclonal antibody of claim 1, or the antigen binding fragment of claim 12, and a pharmaceutically acceptable carrier.

16. A method of producing an antibody comprising expressing one or more nucleic acid molecules encoding the antibody of claim 1 in a host cell; and purifying the antibody.

17. A method of detecting the presence of *Plasmodium falciparum* in a biological sample from a human subject, comprising: contacting the biological sample with an effective amount of the antibody of claim 8 under conditions sufficient to form an immune complex; and detecting the presence of the immune complex in the biological sample, wherein the presence of the immune complex in the biological sample indicates the presence of the *P. falciparum* in the sample.

18. A method of inhibiting a *P. falciparum* infection in a subject, comprising administering an effective amount of the antibody of claim 1 to the subject, wherein the subject has a *P. falciparum* infection.

* * * * *

SEQUENCE LISTING

```
<160> NUMBER OF SEQ ID NOS: 124

<210> SEQ ID NO 1
<211> LENGTH: 121
<212> TYPE: PRT
<213> ORGANISM: homo sapiens

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile His Trp Val Arg Gln Ala Pro Gly Gln Arg Leu Glu Trp Met
        35                  40                  45

Gly Trp Ile Lys Ala Gly Asn Gly Asp Thr Arg Tyr Ser Gln Lys Phe
    50                  55                  60

Gln Gly Arg Val Thr Ile Thr Arg Asp Thr Ser Ala Thr Thr Ala Tyr
65                  70                  75                  80

Met Glu Leu Ser Ser Leu Arg Ser Glu Asp Thr Ala Val Tyr Tyr Cys
                85                  90                  95

Gly Leu Leu Thr Val Leu Thr Pro Asp Asp Ala Phe Asp Ile Trp Gly
            100                 105                 110

Gln Gly Thr Met Val Thr Val Ser Ser
        115                 120

<210> SEQ ID NO 2
```

```
<211> LENGTH: 113
<212> TYPE: PRT
<213> ORGANISM: homo sapiens

<400> SEQUENCE: 2

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Ile Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Ser Ser Pro Leu Thr Phe Gly Gly Gly Thr Lys Val Glu Ile
            100                 105                 110

Lys

<210> SEQ ID NO 3
<211> LENGTH: 121
<212> TYPE: PRT
<213> ORGANISM: homo sapiens

<400> SEQUENCE: 3

Gln Val Gln Leu Val Gln Ser Gly Pro Glu Val Lys Lys Pro Gly Thr
1               5                   10                  15

Ser Val Lys Val Ser Cys Lys Ala Ser Gly Phe Thr Phe Ser Ser Ser
            20                  25                  30

Ala Val Gln Trp Val Arg Gln Ala Arg Gly Gln Arg Leu Glu Trp Ile
        35                  40                  45

Gly Trp Ile Val Val Gly Ser Gly Lys Thr Lys Tyr Ala Gln Asn Phe
    50                  55                  60

Gln Gln Arg Val Thr Ile Thr Arg Asp Met Ser Thr Ser Thr Ala Tyr
65                  70                  75                  80

Leu Glu Leu Ser Thr Leu Arg Ser Glu Asp Thr Ala Val Tyr Tyr Cys
                85                  90                  95

Ala Ala Val Val Asn Trp Asn Asp Glu Ser Gly Phe Asp Pro Trp Gly
            100                 105                 110

Gln Gly Thr Leu Val Thr Val Ser Ser
        115                 120

<210> SEQ ID NO 4
<211> LENGTH: 106
<212> TYPE: PRT
<213> ORGANISM: homo sapiens

<400> SEQUENCE: 4

Asp Ile Gln Met Thr Gln Ser Pro Ser Ser Leu Ser Ala Phe Val Gly
1               5                   10                  15

Asp Arg Val Thr Ile Thr Cys Arg Ala Ser Gln Ser Ile Gly Thr Tyr
            20                  25                  30

Leu Asn Trp Tyr Gln Gln Lys Val Gly Gln Ala Pro Lys Leu Leu Ile
        35                  40                  45

Tyr Thr Ala Ser Ser Leu Arg Ser Gly Val Pro Ser Arg Phe Ser Gly
```

```
                50              55                 60
Ser Gly Ser Gly Thr Asp Phe Thr Leu Thr Ile Ser Leu Gln Pro
 65              70                 75                 80

Glu Asp Phe Ala Thr Tyr Tyr Cys Gln Gln Ser Tyr Ser Thr Tyr Thr
                    85                 90                 95

Phe Gly Gln Gly Thr Lys Leu Glu Ile Lys
                100                105

<210> SEQ ID NO 5
<211> LENGTH: 122
<212> TYPE: PRT
<213> ORGANISM: homo sapiens

<400> SEQUENCE: 5

Glu Val Gln Leu Val Glu Ser Gly Gly Val Val Gln Pro Gly Arg
 1               5                  10                 15

Ser Leu Arg Leu Ser Cys Ala Ala Ser Gly Phe Thr Phe Ser Ser Tyr
                20                 25                 30

Gly Met Tyr Trp Val Arg Gln Ala Pro Gly Lys Gly Leu Glu Trp Val
                35                 40                 45

Ala Leu Ile Ser His Asp Gly Ser Asn Lys Phe Tyr Ala Asp Ser Val
 50                 55                 60

Lys Gly Arg Phe Thr Ile Ser Arg Asp Asn Ser Lys Asn Thr Leu Tyr
 65                 70                 75                 80

Leu Gln Met Asn Ser Leu Arg Ala Glu Asp Thr Ala Val Tyr Tyr Cys
                85                 90                 95

Ala Lys Asp Leu Gly Tyr Ser Ser Ser Trp Gly Tyr Phe Asp Tyr Trp
                100                105                110

Gly Gln Gly Thr Leu Val Thr Val Ser Ser
        115                120

<210> SEQ ID NO 6
<211> LENGTH: 106
<212> TYPE: PRT
<213> ORGANISM: homo sapiens

<400> SEQUENCE: 6

Glu Ile Val Leu Thr Gln Ser Pro Ala Thr Leu Ser Leu Ser Pro Gly
 1               5                  10                 15

Glu Arg Ala Thr Leu Ser Cys Arg Ala Ser Gln Ser Val Ser Ser Tyr
                20                 25                 30

Leu Ala Trp Tyr Gln Gln Lys Pro Gly Gln Ala Pro Arg Leu Leu Ile
                35                 40                 45

Tyr Asp Ala Ser Asn Arg Ala Thr Gly Ile Pro Ala Arg Phe Ser Gly
 50                 55                 60

Ser Gly Ser Gly Thr Asp Phe Thr Leu Thr Ile Ser Ser Leu Glu Pro
 65                 70                 75                 80

Glu Asp Phe Ala Val Tyr Tyr Cys Gln Gln Arg Ser Asn Trp Tyr Thr
                85                 90                 95

Phe Gly Gln Gly Thr Lys Leu Glu Ile Lys
                100                105

<210> SEQ ID NO 7
<211> LENGTH: 124
<212> TYPE: PRT
<213> ORGANISM: homo sapiens

<400> SEQUENCE: 7
```

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Ile His Trp Val Arg Gln Ala Pro Gly Lys Gly Leu Glu Trp Val
            35                  40                  45

Ala Val Ile Trp Tyr Asp Gly Ser Lys Lys Tyr Tyr Gly Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Ala Val Ile Ala Ala Thr Gly Thr Arg Gly Tyr Trp Phe Asp
            100                 105                 110

Pro Trp Gly Gln Gly Thr Leu Val Thr Val Ser Ser
            115                 120
```

```
<210> SEQ ID NO 8
<211> LENGTH: 106
<212> TYPE: PRT
<213> ORGANISM: homo sapiens

<400> SEQUENCE: 8
```

```
Asp Ile Ile Met Thr Gln Ser Pro Val Ser Leu Ser Ala Ser Val Gly
1               5                   10                  15

Asp Arg Val Thr Ile Thr Cys Arg Ala Ser Gln Ser Ile Ser Ser His
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Ser Cys Gln Gln Thr Tyr Arg Gly Phe Thr
                85                  90                  95

Phe Ala Pro Gly Thr Lys Val Asp Ile Lys
            100                 105
```

```
<210> SEQ ID NO 9
<211> LENGTH: 119
<212> TYPE: PRT
<213> ORGANISM: homo sapiens

<400> SEQUENCE: 9
```

```
Gln Val Gln Leu Val Gln Ser Gly Ser Glu Leu Lys Lys Pro Gly Ala
1               5                   10                  15

Ser Val Lys Val Ser Cys Lys Thr Ser Gly Tyr Thr Phe Thr Thr Tyr
            20                  25                  30

Ala Met Asn Trp Val Arg Gln Ala Pro Gly Gln Gly Leu Glu Trp Met
            35                  40                  45

Gly Trp Ile Asn Thr Asn Thr Gly Asn Pro Thr Tyr Ala Pro Gly Phe
50                  55                  60

Thr Gly Arg Phe Val Phe Ser Phe Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95
```

```
Ala Arg Val Tyr Ser Tyr Gly Val Pro Phe Asp Tyr Trp Gly Gln Gly
            100                 105                 110

Thr Leu Val Thr Val Ser Ser
        115

<210> SEQ ID NO 10
<211> LENGTH: 110
<212> TYPE: PRT
<213> ORGANISM: homo sapiens

<400> SEQUENCE: 10

Gln Ser Val Leu Thr Gln Pro Ala Ser Val Ser Gly Ser Pro Gly Gln
1               5                   10                  15

Ser Ile Thr Ile Ser Cys Thr Ala Thr Ser Ser Asn Val Gly Ser Phe
            20                  25                  30

Asn Leu Val Ser Trp Tyr Gln His Pro Gly Lys Ala Pro Lys Leu
        35                  40                  45

Ile Ile His Glu Val Ser Lys Arg Pro Ser Gly Ala Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Val Gly Ser
                85                  90                  95

Asp Thr Trp Val Phe Gly Gly Gly Thr Lys Leu Thr Val Leu
            100                 105                 110

<210> SEQ ID NO 11
<211> LENGTH: 121
<212> TYPE: PRT
<213> ORGANISM: homo sapiens

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile His Trp Val Arg Gln Ala Pro Gly Gln Arg Leu Glu Trp Met
        35                  40                  45

Gly Trp Ile Lys Ala Gly Asn Gly Asn Thr Arg Tyr Ser Gln Lys Phe
    50                  55                  60

Gln Asp Arg Val Thr Ile Thr Arg Asp Thr Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Ala Leu Leu Thr Val Leu Thr Pro Asp Asp Ala Phe Asp Ile Trp Gly
            100                 105                 110

Gln Gly Thr Met Val Thr Val Ser Ser
        115                 120

<210> SEQ ID NO 12
<211> LENGTH: 113
<212> TYPE: PRT
<213> ORGANISM: homo sapiens

<400> SEQUENCE: 12

Asp Ile Val Met Thr Gln Ser Pro Asp Ser Leu Ala Val Ser Leu Gly
1               5                   10                  15
```

```
Glu Arg Ala Thr Ile Asn Cys Lys Ser Ser Gln Ser Val Leu Tyr Ser
                 20                  25                  30

Ser Asn Asn Lys Asn Tyr Leu Ala Trp Tyr Gln Gln Lys Pro Gly Gln
         35                  40                  45

Pro Pro Asn Leu Leu Ile Tyr Trp Ala Ser Thr Arg Gln Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                 85                  90                  95

Tyr Tyr Ser Ser Pro Leu Thr Phe Gly Gly Gly Thr Lys Val Glu Ile
            100                 105                 110

Lys

<210> SEQ ID NO 13
<211> LENGTH: 451
<212> TYPE: PRT
<213> ORGANISM: homo sapiens

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Ile His Trp Val Arg Gln Ala Pro Gly Gln Arg Leu Glu Trp Met
            35                  40                  45

Gly Trp Ile Lys Ala Gly Asn Gly Asn Thr Arg Tyr Ser Gln Lys Phe
        50                  55                  60

Gln Asp Arg Val Thr Ile Thr Arg Asp Thr Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Ala Leu Leu Thr Val Leu Thr Pro Asp Asp Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270
```

```
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
            355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 14
<211> LENGTH: 220
<212> TYPE: PRT
<213> ORGANISM: homo sapiens

<400> SEQUENCE: 14

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
            20                  25                  30
Ser Asn Asn Lys Asn Tyr Leu Ala Trp Tyr Gln Gln Lys Pro Gly Gln
        35                  40                  45
Pro Pro Asn Leu Leu Ile Tyr Trp Ala Ser Thr Arg Gln Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys His Gln
                85                  90                  95
Tyr Tyr Ser Ser Pro Leu Thr Phe Gly Gly Gly Thr Lys Val Glu Ile
            100                 105                 110
Lys Arg Thr Val Ala Ala Pro Ser Val Phe Ile Phe Pro Pro Ser Asp
        115                 120                 125
Glu Gln Leu Lys Ser Gly Thr Ala Ser Val Val Cys Leu Leu Asn Asn
    130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
            180                 185                 190
```

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 15
<211> LENGTH: 4
<212> TYPE: PRT
<213> ORGANISM: homo sapiens

<400> SEQUENCE: 15

Tyr Ala Ile His
1

<210> SEQ ID NO 16
<211> LENGTH: 17
<212> TYPE: PRT
<213> ORGANISM: homo sapiens

<400> SEQUENCE: 16

Trp Ile Lys Ala Gly Asn Gly Asp Thr Arg Tyr Ser Gln Lys Phe Gln
1               5                   10                  15

Gly

<210> SEQ ID NO 17
<211> LENGTH: 13
<212> TYPE: PRT
<213> ORGANISM: homo sapiens

<400> SEQUENCE: 17

Leu Leu Thr Val Leu Thr Pro Asp Asp Ala Phe Asp Ile
1               5                   10

<210> SEQ ID NO 18
<211> LENGTH: 17
<212> TYPE: PRT
<213> ORGANISM: homo sapiens

<400> SEQUENCE: 18

Lys Ser Ser Gln Ser Val Leu Tyr Ser Asn Asn Lys Asn Tyr Leu
1               5                   10                  15

Ala

<210> SEQ ID NO 19
<211> LENGTH: 7
<212> TYPE: PRT
<213> ORGANISM: homo sapiens

<400> SEQUENCE: 19

Trp Ala Ser Ile Arg Glu Ser
1               5

<210> SEQ ID NO 20
<211> LENGTH: 9
<212> TYPE: PRT
<213> ORGANISM: homo sapiens

<400> SEQUENCE: 20

His Gln Tyr Tyr Ser Ser Pro Leu Thr
1               5

<210> SEQ ID NO 21

```
<211> LENGTH: 4
<212> TYPE: PRT
<213> ORGANISM: homo sapiens

<400> SEQUENCE: 21

Ser Ala Val Gln
1

<210> SEQ ID NO 22
<211> LENGTH: 17
<212> TYPE: PRT
<213> ORGANISM: homo sapiens

<400> SEQUENCE: 22

Trp Ile Val Val Gly Ser Gly Lys Thr Lys Tyr Ala Gln Asn Phe Gln
1               5                   10                  15

Gln

<210> SEQ ID NO 23
<211> LENGTH: 13
<212> TYPE: PRT
<213> ORGANISM: homo sapiens

<400> SEQUENCE: 23

Ala Val Val Asn Trp Asn Asp Glu Ser Gly Phe Asp Pro
1               5                   10

<210> SEQ ID NO 24
<211> LENGTH: 11
<212> TYPE: PRT
<213> ORGANISM: homo sapiens

<400> SEQUENCE: 24

Arg Ala Ser Gln Ser Ile Gly Thr Tyr Leu Asn
1               5                   10

<210> SEQ ID NO 25
<211> LENGTH: 7
<212> TYPE: PRT
<213> ORGANISM: homo sapiens

<400> SEQUENCE: 25

Thr Ala Ser Ser Leu Arg Ser
1               5

<210> SEQ ID NO 26
<211> LENGTH: 8
<212> TYPE: PRT
<213> ORGANISM: homo sapiens

<400> SEQUENCE: 26

Gln Gln Ser Tyr Ser Thr Tyr Thr
1               5

<210> SEQ ID NO 27
<211> LENGTH: 4
<212> TYPE: PRT
<213> ORGANISM: homo sapiens

<400> SEQUENCE: 27

Tyr Gly Met Tyr
1

<210> SEQ ID NO 28
```

```
<211> LENGTH: 17
<212> TYPE: PRT
<213> ORGANISM: homo sapiens

<400> SEQUENCE: 28

Leu Ile Ser His Asp Gly Ser Asn Lys Phe Tyr Ala Asp Ser Val Lys
1               5                   10                  15
Gly

<210> SEQ ID NO 29
<211> LENGTH: 14
<212> TYPE: PRT
<213> ORGANISM: homo sapiens

<400> SEQUENCE: 29

Lys Asp Leu Gly Tyr Ser Ser Ser Trp Gly Tyr Phe Asp Tyr
1               5                   10

<210> SEQ ID NO 30
<211> LENGTH: 11
<212> TYPE: PRT
<213> ORGANISM: homo sapiens

<400> SEQUENCE: 30

Arg Ala Ser Gln Ser Val Ser Ser Tyr Leu Ala
1               5                   10

<210> SEQ ID NO 31
<211> LENGTH: 7
<212> TYPE: PRT
<213> ORGANISM: homo sapiens

<400> SEQUENCE: 31

Asp Ala Ser Asn Arg Ala Thr
1               5

<210> SEQ ID NO 32
<211> LENGTH: 8
<212> TYPE: PRT
<213> ORGANISM: homo sapiens

<400> SEQUENCE: 32

Gln Gln Arg Ser Asn Trp Tyr Thr
1               5

<210> SEQ ID NO 33
<211> LENGTH: 4
<212> TYPE: PRT
<213> ORGANISM: homo sapiens

<400> SEQUENCE: 33

Tyr Gly Ile His
1

<210> SEQ ID NO 34
<211> LENGTH: 17
<212> TYPE: PRT
<213> ORGANISM: homo sapiens

<400> SEQUENCE: 34

Val Ile Trp Tyr Asp Gly Ser Lys Lys Tyr Tyr Gly Asp Ser Val Lys
1               5                   10                  15
Gly
```

<210> SEQ ID NO 35
<211> LENGTH: 16
<212> TYPE: PRT
<213> ORGANISM: homo sapiens

<400> SEQUENCE: 35

Arg Ala Val Ile Ala Ala Thr Gly Thr Arg Gly Tyr Trp Phe Asp Pro
1               5                   10                  15

<210> SEQ ID NO 36
<211> LENGTH: 11
<212> TYPE: PRT
<213> ORGANISM: homo sapiens

<400> SEQUENCE: 36

Arg Ala Ser Gln Ser Ile Ser Ser His Leu Asn
1               5                   10

<210> SEQ ID NO 37
<211> LENGTH: 7
<212> TYPE: PRT
<213> ORGANISM: homo sapiens

<400> SEQUENCE: 37

Ala Ala Ser Ser Leu Gln Ser
1               5

<210> SEQ ID NO 38
<211> LENGTH: 8
<212> TYPE: PRT
<213> ORGANISM: homo sapiens

<400> SEQUENCE: 38

Gln Gln Thr Tyr Arg Gly Phe Thr
1               5

<210> SEQ ID NO 39
<211> LENGTH: 4
<212> TYPE: PRT
<213> ORGANISM: homo sapiens

<400> SEQUENCE: 39

Tyr Ala Met Asn
1

<210> SEQ ID NO 40
<211> LENGTH: 17
<212> TYPE: PRT
<213> ORGANISM: homo sapiens

<400> SEQUENCE: 40

Trp Ile Asn Thr Asn Thr Gly Asn Pro Thr Tyr Ala Pro Gly Phe Thr
1               5                   10                  15

Gly

<210> SEQ ID NO 41
<211> LENGTH: 11
<212> TYPE: PRT
<213> ORGANISM: homo sapiens

<400> SEQUENCE: 41

Arg Val Tyr Ser Tyr Gly Val Pro Phe Asp Tyr
1               5                   10

```
<210> SEQ ID NO 42
<211> LENGTH: 14
<212> TYPE: PRT
<213> ORGANISM: homo sapiens

<400> SEQUENCE: 42

Thr Ala Thr Ser Ser Asn Val Gly Ser Phe Asn Leu Val Ser
1               5                   10

<210> SEQ ID NO 43
<211> LENGTH: 7
<212> TYPE: PRT
<213> ORGANISM: homo sapiens

<400> SEQUENCE: 43

Glu Val Ser Lys Arg Pro Ser
1               5

<210> SEQ ID NO 44
<211> LENGTH: 10
<212> TYPE: PRT
<213> ORGANISM: homo sapiens

<400> SEQUENCE: 44

Cys Ser Tyr Val Gly Ser Asp Thr Trp Val
1               5                   10

<210> SEQ ID NO 45
<211> LENGTH: 17
<212> TYPE: PRT
<213> ORGANISM: homo sapiens

<400> SEQUENCE: 45

Trp Ile Lys Ala Gly Asn Gly Asn Thr Arg Tyr Ser Gln Lys Phe Gln
1               5                   10                  15

Asp

<210> SEQ ID NO 46
<211> LENGTH: 7
<212> TYPE: PRT
<213> ORGANISM: homo sapiens

<400> SEQUENCE: 46

Trp Ala Ser Thr Arg Gln Ser
1               5

<210> SEQ ID NO 47
<211> LENGTH: 363
<212> TYPE: DNA
<213> ORGANISM: homo sapiens

<400> SEQUENCE: 47
caggtgcagc ttgtgcagtc tggggctgag gtgaagaagc ctggggcctc agtgaaggtt      60
tcctgcaagg cctctggata caccttcact agttatgcta tacattgggt gcgccaggcc     120
cccggacaaa ggcttgagtg gatgggatgg atcaaggctg gcaatggtga tacaagatat     180
tcacagaagt tccagggcag agtcaccatt accagggaca catccgcgac acagcctac     240 atggagctga gcagcctgag atctgaagac acggctgtat attactgtgg cctacttacg     300
gtgctaactc ctgatgatgc atttgatatc tggggccaag ggacaatggt caccgtctct     360
tca                                                                    363
```

<210> SEQ ID NO 48
<211> LENGTH: 339
<212> TYPE: DNA
<213> ORGANISM: homo sapiens

<400> SEQUENCE: 48

```
gacatcgtga tgacccagtc tccagactcc ctggctgtgt ctctgggcga gagggccacc    60
atcaactgca gtccagcca gagtgtttta tacagctcca acaataagaa ctacttagct   120
tggtaccagc agaaaccagg acagcctcct aagctgctca tttattgggc atctatccgg   180
gaatccgggg tccctgaccg attcagtggc agcgggtctg ggacagattt cactctcacc   240
atcagcagcc tgcaggctga agatgtggca gtttattact gtcaccagta ttatagtagt   300
cctctcactt tcggcggagg gaccaaggtg gaaatcaaa                          339
```

<210> SEQ ID NO 49
<211> LENGTH: 363
<212> TYPE: DNA
<213> ORGANISM: homo sapiens

<400> SEQUENCE: 49

```
caggtgcagc tggtgcagtc tgggcctgag gtgaagaagc ctgggacctc agtgaaggtc    60
tcctgcaagg cttctggatt caccttagt agctctgctg tgcagtgggt gcgacaggct   120
cgtggacaac gccttgagtg gataggatgg atcgtcgttg cagtggtaa gacaaagtac   180 gcacagaact ccaacaaag agtcaccatt accagggaca tgtccacaag tacagcctat   240
ctggagctga gcaccctgag atccgaggac acggccgtgt attactgtgc ggcagttgtc   300
aactggaacg acgaaagcgg gttcgacccc tggggccagg gaaccctggt caccgtctcc   360
tca                                                                363
```

<210> SEQ ID NO 50
<211> LENGTH: 318
<212> TYPE: DNA
<213> ORGANISM: homo sapiens

<400> SEQUENCE: 50

```
gacatccaga tgacccagtc tccatcgtcc ctgtctgcat ttgtgggaga cagagtcacc    60
atcacttgcc gggcaagtca gagcattggc acctatttaa attggtatca gcagaaagta   120
ggtcaagccc ctaagctcct gatatatact gcatccagtc tgcgaagtgg ggtcccatca   180
aggttcagtg gcagtggatc tgggacagat ttcactctca ccatcaccag tctgcaacct   240
gaagattttg caacttacta ctgtcaacag agttacagta cctacacttt tggccagggg   300
accaagctgg agatcaaa                                                 318
```

<210> SEQ ID NO 51
<211> LENGTH: 366
<212> TYPE: DNA
<213> ORGANISM: homo sapiens

<400> SEQUENCE: 51

```
gaggtgcagt tggtggagtc tgggggaggc gtggtccagc ctgggaggtc cctgagactc    60
tcctgtgcag cctctggatt caccttcagt agctatggca tgtactgggt ccgccaggct   120
ccaggcaagg ggctggagtg gtggcactt atatcacatg atggaagtaa taaattctat   180
gcagactccg tgaagggccg attcaccatc tccagagaca attccaagaa cacgctgtat   240
ctgcaaatga acagcctgag agctgaggac acggctgtgt attactgtgc gaaagacttg   300
```

```
ggttatagca gcagctgggg gtactttgac tactggggcc agggaaccct ggtcaccgtc    360
tcctca                                                               366

<210> SEQ ID NO 52
<211> LENGTH: 318
<212> TYPE: DNA
<213> ORGANISM: homo sapiens

<400> SEQUENCE: 52
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggtacacttt tggccagggg   300
accaagctgg agatcaaa                                                 318

<210> SEQ ID NO 53
<211> LENGTH: 372
<212> TYPE: DNA
<213> ORGANISM: homo sapiens

<400> SEQUENCE: 53
caggtgcagc tggtggagtc tgggggaggc gtggtccagc ctgggaggtc cctgagactc    60
tcctgtgcag cgtctggatt caccttcagt agctatggca tacactgggt ccgccaggct   120
ccaggcaagg ggctggagtg ggtggcagtt atatggtatg atggaagtaa gaaatattat   180
ggagactctg tgaagggccg attcaccatc tccagagaca attccaagaa cacgctgtat   240
ctgcaaatga acagcctgag agtcgaggac acggctgtgt attactgtgc gagggctgtt   300
atagcagcaa ctggtacgcg aggttactgg ttcgacccct ggggccaggg aaccctggtc   360
accgtctcct ca                                                       372

<210> SEQ ID NO 54
<211> LENGTH: 318
<212> TYPE: DNA
<213> ORGANISM: homo sapiens

<400> SEQUENCE: 54
gacatcatta tgacccagtc tccagtctcc ctgtctgcat ctgtaggaga cagagtcacc    60
atcacttgcc gggcaagtca gagcattagc agccatttaa attggtatca gcagaaacca   120
gggaaagccc ctaagctcct gatctatgct gcatccagtt tgcaaagtgg gtcccatca    180 aggttcagtg gcagtggatc tgggacagat ttcactctca ccatcagcag tctgcaacct   240
gaagattttg caacttactc ctgtcaacag acttacaggg ggttcacttt cgcccctggg   300
accaaagtgg atatcaaa                                                 318

<210> SEQ ID NO 55
<211> LENGTH: 357
<212> TYPE: DNA
<213> ORGANISM: homo sapiens

<400> SEQUENCE: 55
caggtgcagc tggtgcaatc tgggtctgag ttgaagaagc ctggggcctc agtgaaggtt    60
tcctgcaaga cttctggata caccttcact acctatgcta tgaattgggt gcgacaggcc   120
```

| | |
|---|---|
| cctggacaag ggcttgagtg gatgggatgg atcaacacca acactggaaa cccaacgtac | 180 |
| gccccgggct tcacagggcg gtttgtcttc tccttcgaca cctctgtcag cacggcatat | 240 |
| ctgcagatca gcagcctgaa ggctgaggac actgccgttt attactgtgc gagagtctac | 300 |
| agctatgggg tcccatttga ctactggggc cagggaaccc tggtcaccgt ctcctca | 357 |

<210> SEQ ID NO 56
<211> LENGTH: 371
<212> TYPE: DNA
<213> ORGANISM: homo sapiens

<400> SEQUENCE: 56

| | |
|---|---|
| cagtctgtgc tgactcagcc tgcctccgtg tctgggtctc ctggacagtc gatcaccatc | 60 |
| tcctgcactg caaccagcag taatgttggg agttttaacc ttgtctcctg gtaccaacat | 120 |
| cacccaggca aagcccccaa actcatcatt catgaggtca gtaagcggcc ctcagggact | 180 |
| tctaatcgct tctctggctc caagtctggc aacacggcct ccctgacaat ctctgggctc | 240 |
| caggctgagg acgaggctga ttattactgc tgctcatatg taggcagtga cacttgggtg | 300 |
| ttcggcggag ggaccaagct gaccgtcctg ggtcagccca aggctgcccc ctcggtcact | 360 |
| ctgttcccgc c | 371 |

<210> SEQ ID NO 57
<211> LENGTH: 363
<212> TYPE: DNA
<213> ORGANISM: homo sapiens

<400> SEQUENCE: 57

| | |
|---|---|
| caggtgcagc ttgtgcagtc tggggctgag gtgaagaagc ctggggcctc agtgaaggtt | 60 |
| tcctgcaagg cctctggata caccttcact agttatgcta tcattgggt gcgccaggcc | 120 |
| cccggacaaa ggcttgagtg gatggggtgg atcaaggctg caatggtaa tacaagatat | 180 |
| tcacagaagt tccaggacag agtcaccatt accagggaca catccacgac cacagcctac | 240 |
| atggagctga gcagcctgag atctgaagac acggctgtgt attactgtgc cctacttacg | 300 |
| gtgctaactc ctgatgatgc ttttgatatc tggggccagg ggaccatggt caccgtctct | 360 |
| tca | 363 |

<210> SEQ ID NO 58
<211> LENGTH: 339
<212> TYPE: DNA
<213> ORGANISM: homo sapiens

<400> SEQUENCE: 58

| | |
|---|---|
| gacatcgtga tgacccagtc tccagactcc ctggctgtgt ctctgggcga gagggccacc | 60 |
| atcaactgca agtccagcca gagtgttcta tacagctcca acaataagaa ctacttagct | 120 |
| tggtaccagc agaaaccagg acagcctcct aacctgctca tttactgggc atctacccgg | 180 |
| caatccgggg tccctgaccg attcagtggc agcgggtctg ggacagattt cactctcacc | 240 |
| atcagcagcc tgcaggctga agatgtggca gtttattact gtcaccagta ttatagtagt | 300 |
| cctctcactt tcggcggagg gaccaaggtg gaaatcaaa | 339 |

<210> SEQ ID NO 59
<211> LENGTH: 1353
<212> TYPE: DNA
<213> ORGANISM: homo sapiens

<400> SEQUENCE: 59

| | |
|---|---|
| caggtgcagc ttgtgcagtc tggggctgag gtgaagaagc ctggggcctc agtgaaggtt | 60 |
| tcctgcaagg cctctggata caccttcact agttatgcta tacattgggt gcgccaggcc | 120 |
| cccggacaaa ggcttgagtg gatggggtgg atcaaggctg gcaatggtaa tacaagatat | 180 |
| tcacagaagt tccaggacag agtcaccatt accagggaca catccacgac cacagcctac | 240 |
| atggagctga gcagcctgag atctgaagac acggctgtgt attactgtgc cctacttacg | 300 |
| gtgctaactc ctgatgatgc ttttgatatc tggggccagg ggaccatggt caccgtctct | 360 |
| tcagcgtcga ccaagggccc atcggtcttc cccctggcac cctcctccaa gagcacctct | 420 |
| gggggcacag cggccctggg ctgcctggtc aaggactact ccccgaacc cgtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gaaagttgag | 660 |
| cccaaatctt gtgacaaaac tcacacatgc ccaccgtgcc cagcacctga actcctgggg | 720 |
| ggaccgtcag tcttcctctt ccccccaaaa cccaaggaca ccctcatgat ctcccggacc | 780 |
| cctgaggtca catgcgtggt ggtggacgtg agccacgaag accctgaggt caagttcaac | 840 |
| tggtacgtgg acggcgtgga ggtgcataat gccaagacaa agccgcggga ggagcagtac | 900 |
| aacagcacgt accgtgtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca aagggcagcc ccgagaacca caggtgtaca ccctgccccc atcccgggat | 1080 |
| gagctgacca agaaccaggt cagcctgacc tgcctggtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc tacagcaagc tcaccgtgga caagagcagg | 1260 |
| tggcagcagg ggaacgtctt ctcatgctcc gtgatgcatg aggctctgca caaccactac | 1320 |
| acgcagaaga gcctctccct gtctccgggt aaa | 1353 |

<210> SEQ ID NO 60
<211> LENGTH: 660
<212> TYPE: DNA
<213> ORGANISM: homo sapiens

<400> SEQUENCE: 60

| | |
|---|---|
| gacatcgtga tgacccagtc tccagactcc ctggctgtgt ctctgggcga gagggccacc | 60 |
| atcaactgca agtccagcca gagtgttcta tacagctcca acaataagaa ctacttagct | 120 |
| tggtaccagc agaaaccagg acagcctcct aacctgctca tttactgggc atctacccgg | 180 |
| caatccgggg tccctgaccg attcagtggc agcgggtctg ggacagattt cactctcacc | 240 |
| atcagcagcc tgcaggctga agatgtggca gtttattact gtcaccagta ttatagtagt | 300 |
| cctctcactt tcggcggagg gaccaaggtg gaaatcaaac gtacggtggc tgcaccatct | 360 |
| gtcttcatct tcccgccatc tgatgagcag ttgaaatctg gaactgcctc tgttgtgtgc | 420 |
| ctgctgaata acttctaccc cagagaagcc aaagtgcagt ggaaggtgga caacgccctg | 480 |
| cagagcggaa acagccagga aagcgtgaca gagcaggatt ccaaggattc acatacagc | 540 |
| ctgagcagca cactgacact gtccaaggcc gactacgaga agcacaaggt gtacgcctgc | 600 |
| gaagtgacac accagggact gtcctcccct gtgacaaaga gcttcaacag aggagaatgc | 660 |

<210> SEQ ID NO 61

```
<211> LENGTH: 15
<212> TYPE: PRT
<213> ORGANISM: Artificial Sequence
<220> FEATURE:
<223> OTHER INFORMATION: Synthetic peptide

<400> SEQUENCE: 61

Pro Ala Asp Gly Asn Pro Asp Pro Asn Ala Asn Pro Asn Val Asp
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Synthetic peptide

<400> SEQUENCE: 62

Asn Pro Asp Pro Asn Ala Asn Pro Asn Val Asp Pro Asn Ala Asn
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic peptide

<400> SEQUENCE: 63

Asn Ala Asn Pro Asn Val Asp Pro Asn Ala Asn Pro Asn Val Asp
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Synthetic peptide

<400> SEQUENCE: 64

Asn Val Asp Pro Asn Ala Asn Pro Asn Val Asp Pro Asn Ala Asn
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic peptide

<400> SEQUENCE: 65

Asn Ala Asn Pro Asn Val Asp Pro Asn Ala Asn Pro Asn Val Asp
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Synthetic peptide

<400> SEQUENCE: 66

Asn Val Asp Pro Asn Ala Asn Pro Asn Val Asp Pro Asn Ala Asn
1               5                   10                  15

<210> SEQ ID NO 67
<211> LENGTH: 15
```

```
<212> TYPE: PRT
<213> ORGANISM: Artificial Sequence
<220> FEATURE:
<223> OTHER INFORMATION: Synthetic peptide

<400> SEQUENCE: 67

Asn Ala Asn Pro Asn Val Asp Pro Asn Ala Asn Pro Asn Ala Asn
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic peptide

<400> SEQUENCE: 68

Asn Val Asp Pro Asn Ala Asn Pro Asn Ala Asn Pro Asn Ala Asn
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Synthetic peptide

<400> SEQUENCE: 69

Asn Ala Asn Pro Asn Ala Asn Pro Asn Ala Asn Pro Asn Ala Asn
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Synthetic peptide

<400> SEQUENCE: 70

Asn Ala Asn Pro Asn Ala Asn Pro Asn Ala Asn Pro Asn Val Asp
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Synthetic peptide

<400> SEQUENCE: 71

Asn Ala Asn Pro Asn Ala Asn Pro Asn Val Asp Pro Asn Ala Asn
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Synthetic peptide

<400> SEQUENCE: 72

Asn Ala Asn Pro Asn Val Asp Pro Asn Ala Asn Pro Asn Ala Asn
1               5                   10                  15

<210> SEQ ID NO 73
<211> LENGTH: 15
<212> TYPE: PRT
```

```
<213> ORGANISM: Artificial Sequence
<220> FEATURE:
<223> OTHER INFORMATION: Synthetic peptide

<400> SEQUENCE: 73

Asn Val Asp Pro Asn Ala Asn Pro Asn Ala Asn Pro Asn Ala Asn
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Synthetic peptide

<400> SEQUENCE: 74

Asn Ala Asn Pro Asn Ala Asn Pro Asn Ala Asn Pro Asn Lys Asn
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Synthetic peptide

<400> SEQUENCE: 75

Asn Ala Asn Pro Asn Ala Asn Pro Asn Lys Asn Gln Gly Asn
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Synthetic peptide

<400> SEQUENCE: 76

Asn Ala Asn Pro Asn Lys Asn Asn Gln Gly Asn Gly Gln Gly His
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Synthetic peptide

<400> SEQUENCE: 77

Gln Glu Tyr Gln Cys Tyr Gly Ser Ser Ser Asn Thr Arg Val Leu
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Synthetic peptide

<400> SEQUENCE: 78

Lys Leu Lys Gln Pro Ala Asp Gly Asn Pro Asp Pro Asn Ala Asn
1               5                   10                  15

<210> SEQ ID NO 79
<211> LENGTH: 36
<212> TYPE: PRT
<213> ORGANISM: Artificial Sequence
```

<220> FEATURE:
<223> OTHER INFORMATION: Synthetic peptide

<400> SEQUENCE: 79

Asn Ala Asn Pro Asn Ala Asn Pro Asn Ala Asn Pro Asn Ala Asn Pro
1               5                   10                  15

Asn Ala Asn Pro Asn Ala Asn Pro Asn Ala Asn Pro Asn Ala Asn Pro
            20                  25                  30

Asn Ala Asn Pro
        35

<210> SEQ ID NO 80
<211> LENGTH: 397
<212> TYPE: PRT
<213> ORGANISM: plasmodium falciparum

<400> SEQUENCE: 80

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
50                  55                  60

Leu Lys Lys Asn Ser Arg Ser Leu Gly Glu Asn Asp Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
            100                 105                 110

Asn Ala Asn Pro Asn Val Asp Pro Asn Ala Asn Pro Asn Val Asp Pro
        115                 120                 125

Asn Ala Asn Pro Asn Ala Asn Pro Asn Ala Asn Pro Asn Ala Asn Pro
    130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
            180                 185                 190

Asn Ala Asn Pro Asn Val Asp Pro Asn Ala Asn Pro Asn Ala Asn Pro
        195                 200                 205

Asn Ala Asn Pro Asn Ala Asn Pro Asn Ala Asn Pro Asn Ala Asn Pro
    210                 215                 220

Asn Ala Asn Pro Asn Ala Asn Pro Asn Ala Asn Pro Asn Ala Asn Pro
225                 230                 235                 240

Asn Ala Asn Pro Asn Ala Asn Pro Asn Ala Asn Pro Asn Ala Asn Pro
                245                 250                 255

Asn Ala Asn Pro Asn Ala Asn Pro Asn Ala Asn Pro Asn Ala Asn Pro
            260                 265                 270

Asn Lys Asn Asn Gln Gly Asn Gly Gln Gly His Asn Met Pro Asn Asp
        275                 280                 285

Pro Asn Arg Asn Val Asp Glu Asn Ala Asn Ala Asn Ser Ala Val Lys
    290                 295                 300

Asn Asn Asn Asn Glu Glu Pro Ser Asp Lys His Ile Lys Glu Tyr Leu
305                 310                 315                 320

Asn Lys Ile Gln Asn Ser Leu Ser Thr Glu Trp Ser Pro Cys Ser Val
            325                 330                 335

Thr Cys Gly Asn Gly Ile Gln Val Arg Ile Lys Pro Gly Ser Ala Asn
            340                 345                 350

Lys Pro Lys Asp Glu Leu Asp Tyr Ala Asn Asp Ile Glu Lys Lys Ile
        355                 360                 365

Cys Lys Met Glu Lys Cys Ser Ser Val Phe Asn Val Asn Ser Ser
    370                 375                 380

Ile Gly Leu Ile Met Val Leu Ser Phe Leu Phe Leu Asn
385                 390                 395

<210> SEQ ID NO 81
<211> LENGTH: 123
<212> TYPE: PRT
<213> ORGANISM: homo sapiens

<400> SEQUENCE: 81

Glu Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Ile Ile Trp His Asp Gly Ser Lys Lys Tyr His Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Val Gly Asn Tyr Gly Gly Asp Trp Gly Ala Gly Phe Asp Tyr
            100                 105                 110

Trp Gly Gln Gly Thr Leu Val Thr Val Ser Ser
        115                 120

<210> SEQ ID NO 82
<211> LENGTH: 106
<212> TYPE: PRT
<213> ORGANISM: homo sapiens

<400> SEQUENCE: 82

Asp Ile Gln Met Thr Gln Ser Pro Ser Phe Leu Ser Ala Ser Val Gly
1               5                   10                  15

Asp Arg Val Thr Ile Ala Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr His Ala Ser Ser Leu Glu Ser Gly Val Pro Ser Arg Phe Ser Gly
    50                  55                  60

Ser Ala Ser Gly Thr Glu Phe Ala Leu Thr Ile Ser Ser Leu Gln Pro
65                  70                  75                  80

Asp Asp Phe Ala Thr Tyr Tyr Cys Gln Gln Tyr Ser Ser Tyr Trp Thr
                85                  90                  95

Phe Gly Gln Gly Thr Lys Val Glu Ile Lys
            100                 105

-continued

<210> SEQ ID NO 83
<211> LENGTH: 369
<212> TYPE: DNA
<213> ORGANISM: homo sapiens

<400> SEQUENCE: 83

| | |
|---|---|
| gaggtacagc tggtcgaaag cggagggggg gtcgtacaac cagggcgatc attgcggtta | 60 |
| agctgtgagg cctcgggatt cacattctca acctatggaa tgcactgggt gagacaggca | 120 |
| ccaggaaagg ggcttgagtg ggtggctatt atttggcacg atggaagcaa aaagtatcac | 180 |
| gctgacagcg tacgaggtcg ctttacaatc tcacgtgaca actccaaaaa cacgctatat | 240 |
| ttgcaaatga atagtctgcg tgcagaggat acagcagtct atttctgtgc acgagttggg | 300 |
| aactacggag gcgactgggg tgccgggttt gattactggg gcaagggac acttgttact | 360 |
| gttagctct | 369 |

<210> SEQ ID NO 84
<211> LENGTH: 318
<212> TYPE: DNA
<213> ORGANISM: homo sapiens

<400> SEQUENCE: 84

| | |
|---|---|
| gacatacaaa tgacccaatc gccctcgttc ctttcggcga gcgtcggtga tcgtgtcacc | 60 |
| atagcctgcc gggcaagtca atcgatctcg agttggttgg cgtggtatca gcagaaacct | 120 |
| gggaaggctc ccaaactatt aatttatcac gcctcatctt tagaatctgg ggtgccctca | 180 |
| cgattttctg gctcagcgag tggcactgag tttgccttaa caatcagctc attacaacct | 240 |
| gatgactttg caacatacta ctgtcaacag tacagctctt actggacatt tgggcagggg | 300 |
| accaaagtcg aaattaac | 318 |

<210> SEQ ID NO 85
<211> LENGTH: 453
<212> TYPE: PRT
<213> ORGANISM: homo sapiens

<400> SEQUENCE: 85

Glu Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Ile Ile Trp His Asp Gly Ser Lys Lys Tyr His Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Val Gly Asn Tyr Gly Gly Asp Trp Gly Ala Gly Phe Asp Tyr
            100                 105                 110

Trp Gly Gln Gly Thr Leu Val Thr Val Ser Ser Pro Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Asp Glu Leu Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Lys
    450

<210> SEQ ID NO 86
<211> LENGTH: 1359
<212> TYPE: DNA
<213> ORGANISM: homo sapiens

<400> SEQUENCE: 86
gaggtacagc tggtcgaaag cggagggggg gtcgtacaac cagggcgatc attgcggtta      60
agctgtgagg cctcgggatt cacattctca acctatggaa tgcactgggt gagacaggca     120
ccaggaaagg ggcttgagtg ggtggctatt atttggcacg atggaagcaa aaagtatcac     180
gctgacagcg tacgaggtcg ctttacaatc tcacgtgaca actccaaaaa cacgctatat     240
ttgcaaatga atagtctgcg tgcagaggat acagcagtct atttctgtgc acgagttggg     300
aactacggag cgactgggg tgccgggttt gattactggg ggcaagggac acttgttact     360
gttagctctc cgtcgaccaa gggcccatcg gtcttccccc tggcaccctc ctccaagagc     420

```
acctctgggg gcacagcggc cctgggctgc ctggtcaagg actacttccc cgaaccggtg      480
acggtgtcgt ggaactcagg cgccctgacc agcggcgtgc acaccttccc ggctgtccta      540
cagtcctcag gactctactc cctcagcagc gtggtgaccg tgccctccag cagcttgggc      600
acccagacct acatctgcaa cgtgaatcac aagcccagca acaccaaggt ggacaagaaa      660
gttgagccca atcttgtga caaaactcac acatgcccac cgtgcccagc acctgaactc       720
ctggggggac cgtcagtctt cctcttcccc ccaaaaccca aggacaccct catgatctcc      780
cggacccctg aggtcacatg cgtggtggtg gacgtgagcc acgaagaccc tgaggtcaag      840
ttcaactggt acgtggacgg cgtggaggtg cataatgcca agacaaagcc gcgggaggag      900
cagtacaaca gcacgtaccg tgtggtcagc gtcctcaccg tcctgcacca ggactggctg      960
aatggcaagg agtacaagtg caaggtctcc aacaaagccc tcccagcccc catcgagaaa     1020
accatctcca aagccaaagg gcagccccga gaaccacagg tgtacaccct gcccccatcc     1080
cgggatgagc tgaccaagaa ccaggtcagc ctgacctgcc tggtcaaagg cttctatccc     1140
agcgacatcg ccgtggagtg ggagagcaat gggcagccgg agaacaacta caagaccacg     1200
cctcccgtgc tggactccga cggctccttc ttcctctaca gcaagctcac cgtggacaag     1260
agcaggtggc agcaggggaa cgtcttctca tgctccgtga tgcatgaggc tctgcacaac     1320
cactacacgc agaagagcct ctccctgtct ccgggtaaa                            1359
```

<210> SEQ ID NO 87
<211> LENGTH: 213
<212> TYPE: PRT
<213> ORGANISM: homo sapiens

<400> SEQUENCE: 87

```
Asp Ile Gln Met Thr Gln Ser Pro Ser Phe Leu Ser Ala Ser Val Gly
1               5                   10                  15

Asp Arg Val Thr Ile Ala Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr His Ala Ser Ser Leu Glu Ser Gly Val Pro Ser Arg Phe Ser Gly
    50                  55                  60

Ser Ala Ser Gly Thr Glu Phe Ala Leu Thr Ile Ser Ser Leu Gln Pro
65                  70                  75                  80

Asp Asp Phe Ala Thr Tyr Tyr Cys Gln Gln Tyr Ser Ser Tyr Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205
```

Asn Arg Gly Glu Cys
    210

<210> SEQ ID NO 88
<211> LENGTH: 4
<212> TYPE: PRT
<213> ORGANISM: homo sapiens

<400> SEQUENCE: 88

Tyr Gly Met His
1

<210> SEQ ID NO 89
<211> LENGTH: 17
<212> TYPE: PRT
<213> ORGANISM: homo sapiens

<400> SEQUENCE: 89

Ile Ile Trp His Asp Gly Ser Lys Lys Tyr His Ala Asp Ser Val Arg
1               5                   10                  15

Gly

<210> SEQ ID NO 90
<211> LENGTH: 15
<212> TYPE: PRT
<213> ORGANISM: homo sapiens

<400> SEQUENCE: 90

Arg Val Gly Asn Tyr Gly Gly Asp Trp Gly Ala Gly Phe Asp Tyr
1               5                   10                  15

<210> SEQ ID NO 91
<211> LENGTH: 11
<212> TYPE: PRT
<213> ORGANISM: homo sapiens

<400> SEQUENCE: 91

Arg Ala Ser Gln Ser Ile Ser Ser Trp Leu Ala
1               5                   10

<210> SEQ ID NO 92
<211> LENGTH: 7
<212> TYPE: PRT
<213> ORGANISM: homo sapiens

<400> SEQUENCE: 92

His Ala Ser Ser Leu Glu Ser
1               5

<210> SEQ ID NO 93
<211> LENGTH: 8
<212> TYPE: PRT
<213> ORGANISM: homo sapiens

<400> SEQUENCE: 93

Gln Gln Tyr Ser Ser Tyr Trp Thr
1               5

<210> SEQ ID NO 94
<211> LENGTH: 15
<212> TYPE: PRT
<213> ORGANISM: Artificial Sequence
<220> FEATURE:
<223> OTHER INFORMATION: Synthetic peptide

<400> SEQUENCE: 94

Ala Pro Asp Pro Asn Ala Asn Pro Asn Val Asp Pro Asn Ala Asn
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Synthetic peptide

<400> SEQUENCE: 95

Asn Ala Asp Pro Asn Ala Asn Pro Asn Val Asp Pro Asn Ala Asn
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Synthetic peptide

<400> SEQUENCE: 96

Asn Pro Ala Pro Asn Ala Asn Pro Asn Val Asp Pro Asn Ala Asn
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Synthetic peptide

<400> SEQUENCE: 97

Asn Pro Asp Ala Asn Ala Asn Pro Asn Val Asp Pro Asn Ala Asn
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Synthetic peptide

<400> SEQUENCE: 98

Asn Pro Asp Pro Ala Ala Asn Pro Asn Val Asp Pro Asn Ala Asn
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Synthetic peptide

<400> SEQUENCE: 99

Asn Pro Asp Pro Asn Ser Asn Pro Asn Val Asp Pro Asn Ala Asn
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Synthetic peptide

```
<400> SEQUENCE: 100

Asn Pro Asp Pro Asn Ala Ala Pro Asn Val Asp Pro Asn Ala Asn
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Synthetic peptide

<400> SEQUENCE: 101

Asn Pro Asp Pro Asn Ala Asn Ala Asn Val Asp Pro Asn Ala Asn
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Synthetic peptide

<400> SEQUENCE: 102

Asn Pro Asp Pro Asn Ala Asn Pro Ala Val Asp Pro Asn Ala Asn
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Synthetic peptide

<400> SEQUENCE: 103

Asn Pro Asp Pro Asn Ala Asn Pro Asn Ala Asp Pro Asn Ala Asn
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Synthetic peptide

<400> SEQUENCE: 104

Asn Pro Asp Pro Asn Ala Asn Pro Asn Val Ala Pro Asn Ala Asn
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Synthetic peptide

<400> SEQUENCE: 105

Asn Pro Asp Pro Asn Ala Asn Pro Asn Val Asp Ala Asn Ala Asn
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Synthetic peptide

<400> SEQUENCE: 106
```

```
Asn Pro Asp Pro Asn Ala Asn Pro Asn Val Asp Pro Ala Ala Asn
1               5                   10                  15
```

<210> SEQ ID NO 107
<211> LENGTH: 15
<212> TYPE: PRT
<213> ORGANISM: Artificial Sequence
<220> FEATURE:
<223> OTHER INFORMATION: Synthetic peptide

<400> SEQUENCE: 107

```
Asn Pro Asp Pro Asn Ala Asn Pro Asn Val Asp Pro Asn Ser Asn
1               5                   10                  15
```

<210> SEQ ID NO 108
<211> LENGTH: 15
<212> TYPE: PRT
<213> ORGANISM: Artificial Sequence
<220> FEATURE:
<223> OTHER INFORMATION: Synthetic peptide

<400> SEQUENCE: 108

```
Asn Pro Asp Pro Asn Ala Asn Pro Asn Val Asp Pro Asn Arg Asn
1               5                   10                  15
```

<210> SEQ ID NO 109
<211> LENGTH: 15
<212> TYPE: PRT
<213> ORGANISM: Artificial Sequence
<220> FEATURE:
<223> OTHER INFORMATION: Synthetic peptide

<400> SEQUENCE: 109

```
Asn Pro Asp Pro Asn Ala Asn Pro Asn Val Asp Pro Asn Ala Ala
1               5                   10                  15
```

<210> SEQ ID NO 110
<211> LENGTH: 15
<212> TYPE: PRT
<213> ORGANISM: Artificial Sequence
<220> FEATURE:
<223> OTHER INFORMATION: Synthetic peptide

<400> SEQUENCE: 110

```
Asn Pro Asp Pro Asn Gly Asn Pro Asn Val Asp Pro Asn Ala Asn
1               5                   10                  15
```

<210> SEQ ID NO 111
<211> LENGTH: 15
<212> TYPE: PRT
<213> ORGANISM: Artificial Sequence
<220> FEATURE:
<223> OTHER INFORMATION: Synthetic peptide

<400> SEQUENCE: 111

```
Asn Pro Asp Pro Asn Val Asn Pro Asn Val Asp Pro Asn Ala Asn
1               5                   10                  15
```

<210> SEQ ID NO 112
<211> LENGTH: 15
<212> TYPE: PRT
<213> ORGANISM: Artificial Sequence
<220> FEATURE:
<223> OTHER INFORMATION: Synthetic peptide

<400> SEQUENCE: 112

Asn Pro Asp Pro Asn Pro Asn Pro Asn Val Asp Pro Asn Ala Asn
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Synthetic peptide

<400> SEQUENCE: 113

Asn Pro Asp Pro Asn Ala Ala Pro Asn Val Asp Pro Asn Ala Asn
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Synthetic peptide

<400> SEQUENCE: 114

Asn Pro Asp Pro Asn Ala Asn Ala Asn Val Asp Pro Asn Ala Asn
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Synthetic peptide

<400> SEQUENCE: 115

Asn Pro Asp Pro Asn Ala Asn Pro Ala Val Asp Pro Asn Ala Asn
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Synthetic peptide

<400> SEQUENCE: 116

Asn Pro Asp Pro Asn Ala Asn Pro Ala Val Asp Pro Ala Ala Asn
1               5                   10                  15

<210> SEQ ID NO 117
<211> LENGTH: 121
<212> TYPE: PRT
<213> ORGANISM: Artificial Sequence
<220> FEATURE:
<223> OTHER INFORMATION: Synthetic peptide

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Ile His Trp Val Arg Gln Ala Pro Gly Gln Arg Leu Glu Trp Met
            35                  40                  45

Gly Trp Ile Lys Ala Gly Asn Gly Gly Gly Tyr Ser Gly Lys Phe
        50                  55                  60

Gln Asp Arg Val Thr Ile Thr Arg Asp Thr Ser Thr Thr Thr Ala Tyr
65                  70                  75                  80

```
Met Glu Leu Ser Ser Leu Arg Ser Glu Asp Thr Ala Val Tyr Tyr Cys
                85                  90                  95

Ala Leu Leu Thr Val Leu Thr Pro Asp Asp Ala Phe Asp Ile Trp Gly
            100                 105                 110

Gln Gly Thr Met Val Thr Val Ser Ser
        115                 120

<210> SEQ ID NO 118
<211> LENGTH: 19
<212> TYPE: PRT
<213> ORGANISM: Artificial Sequence
<220> FEATURE:
<223> OTHER INFORMATION: Synthetic peptide

<400> SEQUENCE: 118

Met Gly Trp Ser Cys Ile Ile Leu Phe Leu Val Ala Thr Ala Thr Gly
1               5                   10                  15

Val His Ser

<210> SEQ ID NO 119
<211> LENGTH: 454
<212> TYPE: PRT
<213> ORGANISM: homo sapiens

<400> SEQUENCE: 119

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Val Ile Trp Tyr Asp Gly Ser Lys Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Ala Val Ile Ala Ala Thr Gly Thr Arg Gly Tyr Trp Phe Asp
            100                 105                 110

Pro Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
```

```
                        245                 250                 255
Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
            450

<210> SEQ ID NO 120
<211> LENGTH: 213
<212> TYPE: PRT
<213> ORGANISM: homo sapiens

<400> SEQUENCE: 120

Asp Ile Ile Met Thr Gln Ser Pro Val Ser Leu Ser Ala Ser Val Gly
1               5                   10                  15

Asp Arg Val Thr Ile Thr Cys Arg Ala Ser Gln Ser Ile Ser Ser His
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Ser Cys Gln Gln Thr Tyr Arg Gly Phe Thr
                85                  90                  95

Phe Ala Pro Gly Thr Lys Val Asp Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160
```

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu His Lys Val Tyr Ala
        180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 121
<211> LENGTH: 1362
<212> TYPE: DNA
<213> ORGANISM: Artificial sequence
<220> FEATURE:
<223> OTHER INFORMATION: anitbody heavy chain

<400> SEQUENCE: 121

```
caggtgcagc tggtggagtc tgggggaggc gtggtccagc ctggagggtc cctgagactc      60
tcctgtgcag cgtctggatt caccttcagt agctatggca tacactgggt ccgccaggct     120
ccaggcaagg ggctggagtg ggtggcagtt atatggtatg atggaagtaa aaatattat     180 ggagactctg tgaagggccg attcaccatc tccagagaca attccaagaa cacgctgtat     240
ctgcaaatga acagcctgag agtcgaggac acggctgtgt attactgtgc gagggctgtt     300
atagcagcaa ctggtacgcg aggttactgg ttcgacccct ggggccaggg aaccctggtc     360
accgtctcct cagcgtcgac caagggccca tcggtcttcc ccctggcacc ctcctccaag     420
agcacctctg ggggcacagc ggccctgggc tgcctggtca aggactactt ccccgaaccc     480
gtgacggtgt cgtggaactc aggcgccctg accagcggcg tgcacacctt cccggctgtc     540
ctacagtcct caggactcta ctccctcagc agcgtggtga ccgtgccctc cagcagcttg     600
ggcacccaga cctacatctg caacgtgaat cacaagccca gcaacaccaa ggtggacaag     660
aaagttgagc ccaaatcttg tgacaaaact cacacatgcc caccgtgccc agcacctgaa     720
ctcctggggg gaccgtcagt cttcctcttc cccccaaaac ccaaggacac cctcatgatc     780
tcccggaccc ctgaggtcac atgcgtggtg gtggacgtga gccacgaaga ccctgaggtc     840
aagttcaact ggtacgtgga cggcgtggag gtgcataatg ccaagacaaa gccgcgggag     900
gagcagtaca acagcacgta ccgtgtggtc agcgtcctca ccgtcctgca ccaggactgg     960
ctgaatggca aggagtacaa gtgcaaggtc tccaacaaag ccctcccagc ccccatcgag    1020
aaaaccatct ccaaagccaa agggcagccc cgagaaccac aggtgtacac cctgcccca    1080 tcccgggatg agctgaccaa gaaccaggtc agcctgacct gcctggtcaa aggcttctat    1140
cccagcgaca tcgccgtgga gtgggagagc aatgggcagc cggagaacaa ctacaagacc    1200
acgcctcccg tgctggactc cgacggctcc ttcttcctct acagcaagct caccgtggac    1260
aagagcaggt ggcagcaggg gaacgtcttc tcatgctccg tgatgcatga ggctctgcac    1320
aaccactaca cgcagaagag cctctccctg tctccgggta aa                       1362
```

<210> SEQ ID NO 122
<211> LENGTH: 639
<212> TYPE: DNA
<213> ORGANISM: artificial sequence
<220> FEATURE:
<223> OTHER INFORMATION: antibody light chain

<400> SEQUENCE: 122

```
gacatcatta tgacccagtc tccagtctcc ctgtctgcat ctgtaggaga cagagtcacc      60
```

```
atcacttgcc gggcaagtca gagcattagc agccatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttactc ctgtcaacag acttacaggg ggttcacttt cgcccctggg    300
accaaagtgg atatcaaacg tacggtggct gcaccatctg tcttcatctt cccgccatct    360
gatgagcagt tgaaatctgg aactgcctct gttgtgtgcc tgctgaataa cttctacccc    420
agagaagcca aagtgcagtg gaaggtggac aacgccctgc agagcggaaa cagccaggaa    480
agcgtgacag agcaggattc caaggattcc acatacagcc tgagcagcac actgacactg    540
tccaaggccg actacgagaa gcacaaggtg tacgcctgcg aagtgacaca ccagggactg    600
tcctcccctg tgacaaagag cttcaacaga ggagaatgc                          639

<210> SEQ ID NO 123
<211> LENGTH: 369
<212> TYPE: DNA
<213> ORGANISM: artificial sequence
<220> FEATURE:
<223> OTHER INFORMATION: codon-optimized antibody heavy chain

<400> SEQUENCE: 123
gaggtgcagc tggtggaaag cggcggaggc gtggtgcagc ctggcagatc tctgagactg     60
agctgcgagg ccagcggctt caccttcagc acctacggca tgcactgggt gcgccaggcc    120
cctggaaaag gcctggaatg ggtggccatc atctggcacg acggcagcaa gaagtaccac    180
gccgatagcg tgcggggcag attcaccatc agccgggaca cagcaagaa caccctgtac    240 ctgcagatga acagcctgcg ggccgaggat accgccgtgt acttctgtgc cagagtgggc    300
aactacggcg gcgattgggg agccggcttt gactattggg gccagggcac actcgtgacc    360
gtgtcctct                                                           369

<210> SEQ ID NO 124
<211> LENGTH: 318
<212> TYPE: DNA
<213> ORGANISM: artificial sequence
<220> FEATURE:
<223> OTHER INFORMATION: codon-optimized antibody light chain

<400> SEQUENCE: 124
gacatccaga tgacccagag cccccagctt ctgagcgcca gcgtgggcga cagagtgaca     60
atcgcctgta gagccagcca gagcatcagc agctggctgg cctggtatca gcagaagcct    120
ggcaaggccc ccaaactgct gatctaccac gccagcagcc tggaaagcgg cgtgcccagc    180 agatttctg gcagcgcctc cggcaccgag ttcgccctga caatcagctc cctgcagccc    240
gacgacttcg ccacctacta ctgccagcag tacagcagct actggacctt cggccagggc    300
accaaggtgg aaatcaag                                                 318
```

UNITED STATES PATENT AND TRADEMARK OFFICE
CERTIFICATE OF CORRECTION

PATENT NO. : 11,021,535 B2
APPLICATION NO. : 16/485354
DATED : June 1, 2021
INVENTOR(S) : Seder et al.

It is certified that error appears in the above-identified patent and that said Letters Patent is hereby corrected as shown below:

In the Claims

Claim 12, Column 145, beginning at Line 24, "ing fragment comprises the $V_H$ and the $V_H$ of the monoclonal antibody," should read --ing fragment comprises the $V_H$ and the $V_L$ of the monoclonal antibody.--

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*